(12) United States Patent
McManus et al.

(10) Patent No.: US 9,433,684 B2
(45) Date of Patent: Sep. 6, 2016

(54) CONJUGATES OF SMALL-INTERFERING NUCLEIC ACIDS

(75) Inventors: Samuel P. McManus, Huntsville, AL (US); Timothy A. Riley, Huntsville, AL (US); Sean M. Culbertson, Gurley, AL (US); Antoni Kozlowski, Huntsville, AL (US); Dennis G. Fry, Huntsville, AL (US); Xuejun Yuan, Huntsville, AL (US); Dawei Sheng, Madison, AL (US); Vidula R. Dixit, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 219 days.

(21) Appl. No.: 12/737,833

(22) PCT Filed: Aug. 19, 2009

(86) PCT No.: PCT/US2009/004747
§ 371 (c)(1),
(2), (4) Date: Sep. 8, 2011

(87) PCT Pub. No.: WO2010/021720
PCT Pub. Date: Feb. 25, 2010

(65) Prior Publication Data
US 2012/0100096 A1   Apr. 26, 2012

Related U.S. Application Data

(60) Provisional application No. 61/153,636, filed on Feb. 18, 2009, provisional application No. 61/198,935, filed on Nov. 12, 2008, provisional application No. 61/189,528, filed on Aug. 19, 2008.

(51) Int. Cl.
| | | |
|---|---|---|
| *C12Q 1/68* | (2006.01) | |
| *C12N 15/11* | (2006.01) | |
| *A61K 47/48* | (2006.01) | |
| *C08G 65/329* | (2006.01) | |

(52) U.S. Cl.
CPC ....... *A61K 47/48215* (2013.01); *C08G 65/329* (2013.01); *C08L 2203/02* (2013.01)

(58) Field of Classification Search
CPC .................. C12N 2310/321; C12N 2310/322; C12N 2310/14; C12N 15/111; C12N 2320/51; A61K 2300/00
See application file for complete search history.

(56) References Cited

U.S. PATENT DOCUMENTS

| | | |
|---|---|---|
| 4,810,646 A | 3/1989 | Jamas et al. |
| 4,992,540 A | 2/1991 | Jamas et al. |
| 5,028,703 A | 7/1991 | Jamas et al. |
| 5,607,677 A | 3/1997 | Jamas et al. |
| 5,741,495 A | 4/1998 | Jamas et al. |
| 5,898,031 A | 4/1999 | Crooke |
| 5,932,462 A | 8/1999 | Harris et al. |
| 6,107,094 A | 8/2000 | Crooke |
| 6,309,623 B1 | 10/2001 | Weers et al. |
| 6,433,040 B1 | 8/2002 | Dellamary et al. |
| 6,565,885 B1 | 5/2003 | Tarara et al. |
| 6,602,977 B1 | 8/2003 | Ljungqvist et al. |
| 6,673,901 B2 | 1/2004 | Koide |
| 6,703,199 B1 | 3/2004 | Koide |
| 6,740,734 B1 | 5/2004 | Nilsson et al. |
| 6,946,117 B1 | 9/2005 | Schutt et al. |
| 7,056,704 B2 | 6/2006 | Tuschl et al. |
| 7,078,196 B2 | 7/2006 | Tuschl et al. |
| 7,078,490 B2 | 7/2006 | Koide |
| 7,119,171 B2 | 10/2006 | Koide |
| 7,223,803 B2 | 5/2007 | Harris et al. |
| 7,452,987 B2 | 11/2008 | Giese et al. |
| 8,916,693 B2 | 12/2014 | McManus et al. |
| 2002/0086356 A1 | 7/2002 | Tuschl et al. |
| 2002/0193331 A1 | 12/2002 | Boussif et al. |
| 2003/0108923 A1 | 6/2003 | Tuschl et al. |
| 2003/0166783 A1* | 9/2003 | Davis et al. .................. 525/192 |
| 2003/0190654 A1 | 10/2003 | Heidenreich et al. |
| 2003/0206887 A1 | 11/2003 | Morrissey et al. |
| 2004/0001811 A1 | 1/2004 | Kreutzer et al. |
| 2004/0038921 A1 | 2/2004 | Kreutzer et al. |
| 2004/0053875 A1 | 3/2004 | Kreutzer et al. |
| 2004/0072779 A1 | 4/2004 | Kreutzer et al. |
| 2004/0091457 A1 | 5/2004 | John et al. |
| 2004/0102408 A1 | 5/2004 | Kreutzer et al. |
| 2004/0121348 A1 | 6/2004 | Kreutzer et al. |
| 2004/0126791 A1 | 7/2004 | Wajant et al. |
| 2004/0175703 A1 | 9/2004 | Kreutzer et al. |
| 2004/0180351 A1 | 9/2004 | Giese et al. |
| 2004/0249178 A1* | 12/2004 | Vargeese et al. ............. 552/506 |
| 2004/0259247 A1 | 12/2004 | Tuschl et al. |

(Continued)

FOREIGN PATENT DOCUMENTS

| | | |
|---|---|---|
| DE | 200 23 125 | 6/2003 |
| EP | 1 144 623 | 8/2002 |
| EP | 1 214 945 | 6/2005 |
| EP | 1 352 061 | 5/2006 |
| EP | 1 527 176 | 1/2007 |
| EP | 1 797 901 | 6/2007 |
| EP | 1 801 210 | 6/2007 |
| EP | 1 857 547 | 11/2007 |
| EP | 1 536 827 | 1/2009 |
| EP | 1 551 868 | 1/2009 |

(Continued)

OTHER PUBLICATIONS

Glen Research catalog, 2014, 5'-Amino-modifier C6, published by Glen Research, p. 1.*

(Continued)

*Primary Examiner* — Kate Poliakova-Georgantas
(74) *Attorney, Agent, or Firm* — Mark A. Wilson

(57) ABSTRACT

The present invention relates to conjugates of small-interfering nucleic acids (siNA). Compositions of siNA suited for administration to a patient are described. Methods for delivering the compositions are also described.

10 Claims, 19 Drawing Sheets

(56) References Cited

U.S. PATENT DOCUMENTS

| | | |
|---|---|---|
| 2004/0259248 A1 | 12/2004 | Tuschl et al. |
| 2005/0014903 A1 | 1/2005 | Kolowski et al. |
| 2005/0026278 A1 | 2/2005 | Tuschl et al. |
| 2005/0043263 A1 | 2/2005 | Giese et al. |
| 2005/0059005 A1 | 3/2005 | Tuschl et al. |
| 2005/0074757 A1 | 4/2005 | Kreutzer et al. |
| 2005/0100907 A1 | 5/2005 | Kreutzer et al. |
| 2005/0112187 A1 | 5/2005 | Meyer |
| 2005/0119470 A1* | 6/2005 | Manoharan et al. ........ 536/22.1 |
| 2005/0176667 A1 | 8/2005 | Vornlocher |
| 2005/0182005 A1 | 8/2005 | Tuschl et al. |
| 2005/0186591 A1 | 8/2005 | Bumcrot et al. |
| 2005/0202077 A1 | 9/2005 | Watson et al. |
| 2005/0227934 A1 | 10/2005 | Stoffel et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0277610 A1 | 12/2005 | Rossi et al. |
| 2005/0281781 A1 | 12/2005 | Ostroff |
| 2005/0288244 A1 | 12/2005 | Manoharan et al. |
| 2006/0008822 A1 | 1/2006 | Manoharan et al. |
| 2006/0014289 A1 | 1/2006 | Ahmadian et al. |
| 2006/0035254 A1 | 2/2006 | Manoharan et al. |
| 2006/0035815 A1 | 2/2006 | Chen et al. |
| 2006/0122137 A1 | 6/2006 | Quay et al. |
| 2006/0142230 A1 | 6/2006 | Quay |
| 2006/0160123 A1 | 7/2006 | Quay |
| 2006/0166910 A1 | 7/2006 | Tuschl et al. |
| 2006/0188472 A1 | 8/2006 | Sommermeyer et al. |
| 2006/0212950 A1 | 9/2006 | Tuschl et al. |
| 2006/0287260 A1 | 12/2006 | Manoharan et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0020308 A1 | 1/2007 | Richard et al. |
| 2007/0031371 A1 | 2/2007 | McManus et al. |
| 2007/0054279 A1 | 3/2007 | Manoharan et al. |
| 2007/0093445 A1 | 4/2007 | Tuschl et al. |
| 2007/0135372 A1 | 6/2007 | MacLachlan et al. |
| 2007/0155658 A1 | 7/2007 | Quay et al. |
| 2007/0160980 A1 | 7/2007 | Haeberli et al. |
| 2007/0161595 A1 | 7/2007 | Bumcrot et al. |
| 2007/0172430 A1 | 7/2007 | Brito et al. |
| 2007/0185050 A1 | 8/2007 | Heidenreich et al. |
| 2007/0197460 A1 | 8/2007 | De Fougerolles et al. |
| 2007/0213257 A1 | 9/2007 | Sweedler |
| 2007/0213292 A1 | 9/2007 | Stoffel et al. |
| 2007/0213293 A1 | 9/2007 | McSwiggen et al. |
| 2007/0229266 A1 | 10/2007 | Gibson |
| 2007/0254362 A1 | 11/2007 | Quay et al. |
| 2007/0265220 A1 | 11/2007 | Rossi et al. |
| 2007/0269892 A1 | 11/2007 | Adami et al. |
| 2007/0275465 A1 | 11/2007 | Woppmann et al. |
| 2007/0275923 A1 | 11/2007 | Chen et al. |
| 2007/0276134 A1 | 11/2007 | Sweedler et al. |
| 2007/0281900 A1 | 12/2007 | Cui et al. |
| 2007/0287179 A1 | 12/2007 | Tuschl et al. |
| 2007/0293449 A1 | 12/2007 | Cui et al. |
| 2007/0293657 A1 | 12/2007 | Adami et al. |
| 2007/0299043 A1 | 12/2007 | Hunter et al. |
| 2008/0039414 A1* | 2/2008 | McSwiggen et al. ........ 514/44 |
| 2008/0044438 A1 | 2/2008 | Ostroff et al. |
| 2008/0064863 A1 | 3/2008 | Nagasaki et al. |
| 2008/0070856 A1 | 3/2008 | Kreutzer et al. |
| 2008/0076701 A1 | 3/2008 | Quay et al. |
| 2008/0097087 A1 | 4/2008 | Nagasaki et al. |
| 2008/0131371 A1 | 6/2008 | Artursson et al. |
| 2008/0166800 A1 | 7/2008 | Kreutzer et al. |
| 2008/0194512 A1 | 8/2008 | John et al. |
| 2008/0233651 A1 | 9/2008 | Kreutzer et al. |
| 2008/0249049 A1 | 10/2008 | Kataoka et al. |
| 2008/0261303 A1 | 10/2008 | Kreutzer et al. |
| 2009/0082274 A1 | 3/2009 | Stumpp et al. |
| 2010/0092572 A1 | 4/2010 | Kaeuper et al. |
| 2010/0129460 A1 | 5/2010 | Adami et al. |
| 2010/0291205 A1 | 11/2010 | Downie et al. |
| 2010/0311654 A1 | 12/2010 | Roy et al. |
| 2011/0213013 A1 | 9/2011 | McManus et al. |
| 2011/0269916 A1 | 11/2011 | Chenault et al. |
| 2012/0189704 A1 | 7/2012 | Ben-Shalom et al. |
| 2013/0266650 A1 | 10/2013 | Jackson et al. |

FOREIGN PATENT DOCUMENTS

| | | |
|---|---|---|
| WO | WO 99/16873 | 4/1999 |
| WO | WO 00/63243 | 10/2000 |
| WO | WO 01/64942 | 9/2001 |
| WO | WO 02/20565 | 3/2002 |
| WO | WO 02/088171 | 11/2002 |
| WO | WO 2004/035615 | 4/2004 |
| WO | WO 2004/044011 | 5/2004 |
| WO | WO 2005/000320 | 1/2005 |
| WO | WO 2005/019254 | 3/2005 |
| WO | WO 2005/105152 | 11/2005 |
| WO | WO 2006/023544 | 3/2006 |
| WO | WO 2006/069782 | 7/2006 |
| WO | WO 2006/083275 | 8/2006 |
| WO | WO 2006138572 A2 * | 12/2006 |
| WO | WO 2007/021142 | 2/2007 |
| WO | WO 2007/084684 | 7/2007 |
| WO | WO 2007/121947 | 11/2007 |
| WO | WO 2007/121956 | 11/2007 |
| WO | WO 2008/031899 | 3/2008 |
| WO | WO 2008/082282 | 7/2008 |
| WO | WO 2008/109105 | 9/2008 |
| WO | WO 2009/040338 | 4/2009 |
| WO | WO 2010/021718 | 2/2010 |

OTHER PUBLICATIONS

Amarzguioui, et al., "Rational design and in vitro and in vivo delivery of Dicer substrate siRNA," Nature Protocols, vol. 1, No. 2, pp. 508-517, (2006).

Amstutz, et al., "Intracellular Kinase Inhibitors Selected from Combinatorial Libraries of Designed Ankyrin Repeat Proteins," The J. of Biol. Chem., vol. 280, No. 26, Issue of Jul. 1, pp. 24715-24722, (2005).

Binz, et al., "Engineering novel binding proteins from nonimmunoglobulin domains," Nature Biotechnology, vol. 23, No. 10, pp. 1257-1268, (Oct. 2005).

Binz, et al., "High-affinity binders selected from designed ankyrin repeat protein libraries," Nature Biotechnology, vol. 22, No. 5, pp. 575-582, (May 2004).

Bonora, et al., "Synthesis by High-Efficiency Liquid-Phase (HELP) Method of Oligonucleotides Conjugated with High-Molecular Weight Polyethylene Glycols (PEGs)", Biological Procedures Online, vol. 1, No. 1, pp. 59-69, (May 14, 1998).

De Fougerolles, et al., "Interfering with disease: a progress report on siRNA-based therapeutics," Nature Reviews, vol. 6, pp. 443-453, (Jun. 2007).

Duan, et al., "Cationic nano-copolymers mediated IKKβ targeting siRNA inhibit the proliferation of human Tenon's capsule fibrolasts in vitro," Molecular Vision, vol. 14, pp. 2616-2628, (2008).

Fukushima, et al., "PEGylated Polyplex Micelles from Triblock Catiomers with Spatially Ordered Layering of Condensed pDNA and Buffering Units for Enhanced Intracellular Gene Delivery", J. Am. Chem. Soc., vol. 127, pp. 2810-2811, (2005).

Hosseinkhani, et al., "Liver targeting of plasmid DNA by pullulan conjugation based on metal coordination," J. of Contr. Rel., vol. 83, pp. 287-302, (2002).

Howard, et al., "RNA Interference in Vitro and in Vivo Using a Chitosan/siRNA Nanoparticle System," Molecular Therapy, vol. 14, No. 4, pp. 476-484, (Oct. 2006).

Husseini, et al., "Ultrasonic release of doxorubicin from Pluronic P105 micelles stabilized with an interpenetrating network of N,N-diethylacrylamide," J. of Control Rel., vol. 83, pp. 303-305, (2002).

Jiang, et al., "Chitosan-graft-polyethylenimine as a gene carrier," J. of Contr. Rel., vol. 117, pp. 273-280, (2007).

(56) References Cited

OTHER PUBLICATIONS

Kataoka, et al., "Block copolymer micelles as vehicles for drug delivery," J. of Contr. Rel., vol. 24, pp. 119-132, (1993).

Katas, et al., "Development and characterisation of chitosan nanoparticles for siRNA delivery," J. of Contr. Rel., vol. 115, pp. 216-225, (2006).

Kim, et al., "Synthetic dsRNA Dicer substrates enhance RNAi potency and efficacy," Nature Biotechnology, vol. 23, No. 2, pp. 222-226, (Feb. 2005).

Kim, et al., "PEG conjugated VEGF siRNA for anti-angiogenic gene therapy", J. of Controlled Release, vol. 116, pp. 123-129, (2006).

Kim, et al., "LHRH Receptor-Mediated Delivery of siRNA Using Polyelectrolyte Complex Micelles Self-Assembled from siRNA-PEG-LHRH Conjugate and PEI", Bioconjugate Chemistry, vol. 19, pp. 2156-2162, (2008).

Krutzfeldt, et al., "Silencing of microRNAs in vivo with antagomirs," Nature, vol. 438, pp. 685-689, (Dec. 2005).

Oishi, et al., "Lactosylated Poly(ethylene glycol)-siRNA Conjugate through Acid-Labile β-Thiopropionate Linkage to Construct pH-Sensitive Polyion Complex . . . ", J. Am. Chem. Soc., vol. 127, pp. 1624-1625, (2005).

Ouchi, et al., "Design of Antitumor Agent-Terminated Poly(Ethylene Glycol) Conjugate as Macromolecular Prodrug," Polymer Preprints, vol. 38, No. 1, pp. 582-583, (1997).

Petrie, et al., "An Improved CPG Support for the Synthesis of 3'-Amine-Tailed Oligonucleotides", Bioconjugate Chem., vol. 3, pp. 85-87, (1992).

Rojanarata, et al., "Chitosan-Thiamine Pyrophosphate as a Novel Carrier for siRNA Delivery," Pharmaceutical Research, vol. 25, No. 12, pp. 2807-2814, (Dec. 2008).

Rose, et al., "Functional polarity is introduced by Dicer processing of short substrate RNAs," Nucleic Acids Research, vol. 33, No. 13, pp. 4140-4156, (2005).

Sims, et al., "A Method for the Estimation of Polyethylene Glycol in Plasma Protein Fractions", Analytical Biochemistry, vol. 107, pp. 60-63, (1980).

Stumpp, et al., "DARPins: A true alternative to antibodies," Current Opinion in Drug Discovery & Development, vol. 10, No. 2, pp. 153-159, (2007).

Zahnd, et al., "A Designed Ankyrin Repeat Protein Evolved to Picomolar Affinity to Her2," J. Mol. Biol., vol. 369, pp. 1015-1028, (2007).

Zalipsky, "Chemistry of polyethylene glycol conjugates with biologically active molecules," Advanced Drug Delivery Reviews, vol. 16, pp. 157-182, (1995).

PCT International Search Report and Written Opinion corresponding to PCT Application No. PCT/US2009/004747 date of mailing Feb. 8, 2010.

PCT International Preliminary Report on Patentability corresponding to PCT Application No. PCT/US2009/004747 date of mailing Mar. 3, 2011.

PCT International Search Report and Written Opinion corresponding to PCT Application No. PCT/US2009/004744 date of mailing Feb. 9, 2010.

PCT International Preliminary Report on Patentability corresponding to PCT Application No. PCT/US2009/004744 date of mailing Mar. 3, 2011.

European Examination Report corresponding to European Patent Application No. 09 789 178.2 dated Nov. 17, 2011.

European Examination Report corresponding to European Patent Application No. 09 789 176.6 dated Oct. 27, 2011.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Amiji, et al., "Surface Modification of Polymeric Biomaterials with Poly(ethylene oxide) in Polymers of Biological and Biomedical Significance", Shalaby, S., et al., ACS Symposium Series; ACS, Washington, DC, (1993).

Mao, et al., "Chitosan-DNA Nanoparticles as Gene Carriers: Synthesis, Characterization and Transfection Efficiency", J. Controlled Release, vol. 70, pp. 399-421, (2001).

Entry of Glen Research's Catalog No. "10-1039-xx," accessed from www.glenresearch.com on Jul. 12, 2013.

\* cited by examiner

SEQUENCE LISTING

```
<160> NUMBER OF SEQ ID NOS: 195

<210> SEQ ID NO 1
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1 cuccuuugu uucugcuaac gtt                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cguuagcaga aacaaaagga gtt                                             23

<210> SEQ ID NO 3
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified
```

```
<400> SEQUENCE: 3
cuccuuuugu uucugcuaac gtt                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 4
cguuagcaga aacaaaagga gtt                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
cuccuuuugu uucugcuaac gtt                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
cguuagcaga aacaaaagga gtt                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
cucauuuucu uugugcucac gtt                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
```

```
        Synthetic oligonucleotide
<220> FEATURE:
<223> OTHER INFORMATION: Description of Artificial Sequence: Synthetic
      oligonucleotide

<400> SEQUENCE: 8
cgugagcaca aagaaaauga gtt                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9 cuccuuugu uucugcuaac gtt                                               23

<210> SEQ ID NO 10
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
cguuagcaga aacaaaagga gtt                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
cucauuuucu uugugcucac gtt                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
cgugagcaca aagaaaauga gtt                                              23

<210> SEQ ID NO 13
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cuccuuuugu uucugcuaac g                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cguuagcaga acaaaagga g                                               21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cucauuuucu uugugcucac g                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cgugagcaca aagaaaauga g                                              21

<210> SEQ ID NO 17
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
ttcuccuuuu guuucugcua acg                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
```

-continued ttcguuagca gaaacaaaag gag    23

<210> SEQ ID NO 19
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ttcucauuuu cuuugugcuc acg    23

<210> SEQ ID NO 20
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ttcgugagca caaagaaaau gag    23

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ucuugaugua cuccccucgu u    21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cgaggggagu acaucaagau u    21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucuugaugua cuccccucgu u    21

<210> SEQ ID NO 24
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 24 cgagggagu acaucaagac c                                                  21

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cuugauguac uccccucgu                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gaggggagua caucaagac                                                    19

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
ucuugaugua cuccccucgt t                                                 21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28 cgagggagu acaucaagac c                                                  21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucuugaugua cuccccucgu u                                                 21
```

```
<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30 cgagggagu acaucaagau u                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
ucuugaugua cuccccucgt t                                             21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32 cgagggagu acaucaagat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
acuugaugua cuccccucct t                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34 ggagggagu acaucaagut t                                              21

<210> SEQ ID NO 35
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
aguugaugua cuccccugct t                                          21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
gcaggggagu acaucaacut t                                          21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ucuugaugua cuccccucgu u                                          21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cgaggggagu acaucaagau u                                          21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucuugaugua cuccccucgu u                                          21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
```
cgaggggagu acaucaagac c                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
ucuugaugua cuccccucgt t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
cgaggggagu acaucaagac c                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
ucuugaugua cuccccucgt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44 cgagggagu acaucaagat t                                               21

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cuugauguac uccccucgu                                                 19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46 gagggagua caucaagac                                                19

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
acuugaugua cuccccucct t                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48 ggagggagu acaucaagut t                                             21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
aguugaugua cuccccugct t                                            21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50 gcagggagu acaucaacut t                                             21

<210> SEQ ID NO 51

```
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
cuccuuuugu uucugcuaac gtt                                           23

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
cguuagcaga aacaaaagga gtt                                           23

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uccuuuuguu ucugcuaac                                                19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
guuagcagaa acaaaagga                                                19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uccuuuucuu ucugcuaac                                                19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
```

```
guuagcagaa agaaaagga                                              19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uccuuuucuu ugugcuaac                                              19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
guuagcacaa agaaaagga                                              19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uccuuuucuu ugugguaac                                              19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guuaccacaa agaaaagga                                              19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uccuauucuu ugugguaac                                              19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
```
guuaccacaa agaauagga                                               19

<210> SEQ ID NO 63
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
cuccuuuugu uucugcuaac gtt                                          23

<210> SEQ ID NO 64
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
cguuagcaga aacaaaagga gtt                                          23

<210> SEQ ID NO 65
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 65
cuccuuuugu uucugcuaac gtt                                          23

<210> SEQ ID NO 66
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 66
cguuagcaga aacaaaagga gtt                                            23

<210> SEQ ID NO 67
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 67
cuccuuuugu uucugcuaac gtt                                            23

<210> SEQ ID NO 68
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 68
cguuagcaga aacaaaagga gtt                                            23

<210> SEQ ID NO 69
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69
ttcguuagca gaaacaaaag gag                                            23

<210> SEQ ID NO 70
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 70
cuccuuuugu uucugcuaac gtt                                            23

```
<210> SEQ ID NO 71
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 71
cguuagcaga aacaaaagga gtt                                             23

<210> SEQ ID NO 72
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 72
cuccuuuugu uucugcuaac gtt                                             23

<210> SEQ ID NO 73
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
cuccuuuugu uucugcuaac gtt                                             23

<210> SEQ ID NO 74
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
cuccuuuugu uucugcuaac gtt                                             23

<210> SEQ ID NO 75
<211> LENGTH: 23
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 75
cuccuuuugu uucugcuaac gtt                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
ttcuccuuuu guuucugcua acg                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 77
cguuagcaga aacaaaagga gtt                                              23

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
cuccuuuugu uucugcuaac gtt                                              23

<210> SEQ ID NO 79
<211> LENGTH: 23
<212> TYPE: DNA
<213> ORGANISM: Artificial Sequence
<220> FEATURE:
```

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 79
cguuagcaga aacaaaagga gtt                                              23

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cuccuuuugu uucugcuaac g                                                21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cuccuuuucu uugugcuaac g                                                21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cguuagcaca aacaaaagga g                                                21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 83
cuccuuuugu uucugcuaac g                                                21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

```
<400> SEQUENCE: 84
cguuagcaga aacaaaagga g                                              21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 85
cuccuuuugu uucugcuaac g                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 86
cguuagcaga aacaaaagga g                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 87
cuccuuuugu uucugcuaac g                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 88
cguuagcaga aacaaaagga g                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
              oligonucleotide
<220> FEATURE:
<221> NAME/KEY: modified_base
<222> LOCATION: (1)..(21)
<223> OTHER INFORMATION: 2'-O-methyl modified

<400> SEQUENCE: 89
cuccuuuugu uucugcuaac g                                           21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 90
cguuagcaga aacaaaagga g                                           21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cuccuuuugu uucugcuaac g                                           21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cguuagcaga aacaaaagga g                                           21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 93
cuccuuuugu uucugcuaac g                                           21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(11)
<223> OTHER INFORMATION: 2'-O-methyl modified

<400> SEQUENCE: 94
cguuagcaga aacaaaagga g                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 95
cuccuuuugu uucugcuaac g                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 96
cguuagcaga aacaaaagga g                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: 2'-O-methyl modified

<400> SEQUENCE: 97
cuccuuuugu uucugcuaac g                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: 2'-O-methyl modified
<220> FEATURE:
<221> NAME/KEY: modified_base
<222> LOCATION: (16)..(21)
<223> OTHER INFORMATION: 2'-O-methyl modified

<400> SEQUENCE: 98
cuccuuuugu uucugcuaac g                                              21
```

```
<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: 2'-O-methyl modified
<220> FEATURE:
<221> NAME/KEY: modified_base
<222> LOCATION: (17)..(21)
<223> OTHER INFORMATION: 2'-O-methyl modified

<400> SEQUENCE: 99
cguuagcaga aacaaaagga g                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 100
cuccuuuugu uucugcuaac g                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cuccuuuugu uucugcuaac g                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
cguuagcaga aacaaaagga g                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 103
```
cuccuuuugu uucugcuaac g                                             21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 104
cguuagcaga aacaaaagga g                                             21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 105
cuccuuuugu uucugcuaac g                                             21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 106
cguuagcaga aacaaaagga g                                             21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 107
cuccuuuugu uucugcuaac g                                             21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (11)..(21)
<223> OTHER INFORMATION: 2'-O-methyl modified

<400> SEQUENCE: 108
cguuagcaga aacaaaagga g                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: 2'-O-methyl modified
<220> FEATURE:
<221> NAME/KEY: modified_base
<222> LOCATION: (16)..(21)
<223> OTHER INFORMATION: 2'-O-methyl modified

<400> SEQUENCE: 109
cuccuuuugu uucugcuaac g                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: 2'-O-methyl modified
<220> FEATURE:
<221> NAME/KEY: modified_base
<222> LOCATION: (18)..(21)
<223> OTHER INFORMATION: 2'-O-methyl modified

<400> SEQUENCE: 110
cguuagcaga aacaaaagga g                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
```

```
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 111 cuccuuugu uucugcuaac g                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 112
cguuagcaga aacaaaagga g                                             21
```

-continued

```
<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 113
cuccuuuugu uucugcuaac g                                              21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
```

<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 114
cguuagcaga aacaaaagga g                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:

```
<221> NAME/KEY: modified_base
<222> LOCATION: (21)..(21)
<223> OTHER INFORMATION: 2'-O-methyl modified

<400> SEQUENCE: 115
cuccuuuugu uucugcuaac g                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 116
cguuagcaga aacaaaagga g                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
```

```
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 117
cuccuuuugu uucugcuaac g                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
```

```
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 118
cguuagcaga aacaaaagga g                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cuccuuuugu uucugcuaac g                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cguuagcaga aacaaaagga g                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
cucauuuucu uugugcucac g                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cgugagcaca aagaaaauga g                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(21)
<223> OTHER INFORMATION: 2'-O-methyl modified

<400> SEQUENCE: 123
cuccuuuugu uucugcuaac g                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 124
cguuagcaga aacaaaagga g                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 125
cuccuuuugu uucugcuaac g                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 126
cguuagcaga aacaaaagga g                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 127
cuccuuuugu uucugcuaac g                                              21

<210> SEQ ID NO 128
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 128
cguuagcaga aacaaaagga g                                               21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 129
cuccuuuugu uucugcuaac g                                               21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 130
cguuagcaga aacaaaagga g                                               21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cuccuuuugu uucugcuaac g                                               21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 132
cguuagcaga aacaaaagga g                                               21

<210> SEQ ID NO 133
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 133
cuccuuuugu uucugcuaac g                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
cguuagcaga aacaaaagga g                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 135
cuccuuuugu uucugcuaac g                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 136
cguuagcaga aacaaaagga g                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 137
cuccuuuugu uucugcuaac g                                              21
```

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 138
cguuagcaga aacaaaagga g                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: 2'-O-methyl modified

<400> SEQUENCE: 139
cuccuuuugu uucugcuaac g                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 140
cguuagcaga aacaaaagga g                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: 2'-O-methyl modified
<220> FEATURE:
<221> NAME/KEY: modified_base
<222> LOCATION: (16)..(21)
<223> OTHER INFORMATION: 2'-O-methyl modified

<400> SEQUENCE: 141
cuccuuuugu uucugcuaac g                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic

```
            oligonucleotide
<220> FEATURE:
<221> NAME/KEY: modified_base
<222> LOCATION: (7)..(12)
<223> OTHER INFORMATION: 2'-O-methyl modified
<220> FEATURE:
<221> NAME/KEY: modified_base
<222> LOCATION: (17)..(21)
<223> OTHER INFORMATION: 2'-O-methyl modified

<400> SEQUENCE: 142
cguuagcaga aacaaaagga g                                           21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 143
cuccuuuugu uucugcuaac g                                           21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 144
cguuagcaga aacaaaagga g                                           21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
```

```
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 145
cuccuuuugu uucugcuaac g                                             21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
```

-continued

<400> SEQUENCE: 146
cguuagcaga aacaaaagga g                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 147
cuccuuuugu uucugcuaac g                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base

```
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 148
cguuagcaga aacaaaagga g                                               21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified
```

<400> SEQUENCE: 149
cuccuuuugu uucugcuaac g                                                21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 150
cguuagcaga aacaaaagga g                                                21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:

```
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 151
cuccuuuugu uucugcuaac g                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
```

```
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 152
cguuagcaga aacaaaagga g                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
ucuugaugua cuccccucgt t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154 cgagggagu acaucaagat t                                               21

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ucuugaugua cuccccucg                                                 19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156 cgagggagu acaucaaga                                                  19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
              oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 157
ucuugaugua cuccccucg                                              19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
```

```
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 158 cgagggagu acaucaaga                                                   19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 159
ucuugaugua cuccccucg                                                  19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
```

```
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 160
cgaggggagu acaucaaga                                                  19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
```

-continued

```
<220> FEATURE:
<221> NAME/KEY: modified_base
<222> LOCATION: (19)..(19)
<223> OTHER INFORMATION: 2'-O-methyl modified

<400> SEQUENCE: 161
ucuugaugua cuccccucg                                                        19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 162 cgagggagu acaucaaga                                                         19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
```

```
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 163
ucuugaugua cuccccucg                                                       19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
```

<223> OTHER INFORMATION: 2'-O-methyl modified

<400> SEQUENCE: 164 cgagggagu acaucaaga                                                      19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aauuccagug guucauucc                                                     19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ggaaugaacc acuggaauu                                                     19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 167
aauuccagug guucauucc                                                  19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 168
ggaaugaacc acuggaauu                                                  19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified

```
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 169
aauuccagug guucauucc                                               19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 170
ggaaugaacc acuggaauu                                               19

<210> SEQ ID NO 171
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 171
aauuccagug guucauucc                                                   19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)

```
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 172
ggaaugaacc acuggaauu                                                19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 173
aauuccagug guucauucc                                                19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 174
ggaaugaacc acuggaauu                                                19

<210> SEQ ID NO 175
<211> LENGTH: 12
<212> TYPE: DNA
<213> ORGANISM: Artificial Sequence
<220> FEATURE:
<223> OTHER INFORMATION: Description of Artificial Sequence: Synthetic
      pA-loop

<400> SEQUENCE: 175
aaaaaaaaaa aa                                                       12

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
caccgccaaa tttaactgca ga                                            22

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 177
aagggtttga taagttctag ctgt                                              24

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
tgcacagtat ccttttgaag accataaccc a                                      31

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gtttgagacc ttcaacaccc ca                                                22

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gaccagaggc atacagggac a                                                 21

<210> SEQ ID NO 181
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
ccatgtacgt agccatccag gctgtg                                            26

<210> SEQ ID NO 182
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 182
ucuccuuttg tttctgcuaa cga                                               23

<210> SEQ ID NO 183
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 183
acaacagacu uuaauguaa                                                19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
```

```
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-SH)(Cy5.5) modified

<400> SEQUENCE: 184
acaacagacu uuaauguaa                                                19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (cholesteryl-TEG) modified

<400> SEQUENCE: 185
```
acaacagacu uuaauguaa                                             19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-S-SC6) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 186
acaacagacu uuaauguaa                                             19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)

```
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH) modified

<400> SEQUENCE: 187
acaacagacu uuaauguaa                                              19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
```

<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH) (Cy5.5) modified

<400> SEQUENCE: 188
uuacauuaaa gucuguugu                                                   19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH2) modified

<400> SEQUENCE: 189
uuacauuaaa gucuguugu                                                   19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C3-S-S-C3) modified

<400> SEQUENCE: 190
uuacauuaaa gucuguugu                                              19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
```

```
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 191
acaacagacu uuaauguaa                                              19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 192
uuacauuaaa gucuguugu                                              19

<210> SEQ ID NO 193
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-fluoro-nucleotide
<220> FEATURE:
<221> NAME/KEY: modified_base
<222> LOCATION: (5)..(5)
<223> OTHER INFORMATION: 2'-fluoro-nucleotide
<220> FEATURE:
<221> NAME/KEY: modified_base
<222> LOCATION: (9)..(9)
<223> OTHER INFORMATION: 2'-fluoro-nucleotide
<220> FEATURE:
<221> NAME/KEY: modified_base
<222> LOCATION: (11)..(11)
<223> OTHER INFORMATION: 2'-fluoro-nucleotide
<220> FEATURE:
<221> NAME/KEY: modified_base
<222> LOCATION: (20)..(21)
<223> OTHER INFORMATION: 2'-O-methyl modified

<400> SEQUENCE: 193
acaacagact utaatgtaau u                                              21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-fluoro-nucleotide
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(12)
<223> OTHER INFORMATION: 2'-O-methyl modified
<220> FEATURE:
<221> NAME/KEY: modified_base
<222> LOCATION: (13)..(14)
<223> OTHER INFORMATION: 2'-fluoro-nucleotide
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (16)..(16)
<223> OTHER INFORMATION: 2'-fluoro-nucleotide
<220> FEATURE:
<221> NAME/KEY: modified_base
<222> LOCATION: (17)..(18)
<223> OTHER INFORMATION: 2'-O-methyl modified
```

```
<220> FEATURE:
<221> NAME/KEY: modified_base
<222> LOCATION: (19)..(19)
<223> OTHER INFORMATION: 2'-fluoro-nucleotide
<220> FEATURE:
<221> NAME/KEY: modified_base
<222> LOCATION: (20)..(21)
<223> OTHER INFORMATION: 2'-O-methyl modified

<400> SEQUENCE: 194
uuacauuaaa gucuguuguu u                                               21

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (HSC6) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 195
acaacagacu uuaauguaa                                                  19
```

CONJUGATES OF SMALL-INTERFERING NUCLEIC ACIDS

CROSS-REFERENCED TO RELATED APPLICATIONS

This application is a 35 U.S.C. §371 application of International Application No. PCT/US2009/004747, filed Aug. 19, 2009, designating the United States, which claims the benefit of priority under 35 U.S.C. §119(e) to: Provisional Patent Application No. 61/189,528, filed Aug. 19, 2008; Provisional Patent Application No. 61/198,935, filed Nov. 12, 2008; and Provisional Application No. 61/153,636, filed Feb. 18, 2009; all of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Oct. 10, 2011, is named SHE02050.txt and is 90,544 bytes in size.

FIELD OF THE INVENTION

Among other things, one or more embodiments of the present invention relate generally to conjugates comprising a small interfering nucleic acid (siNA) and a polymer. In addition, the invention relates to (among other things) compositions comprising conjugates, methods for synthesizing conjugates, and methods of administering a composition.

BACKGROUND OF THE INVENTION

RNA interference is currently recognized as a highly specific mechanism of sequence-specific gene silencing. See deFougerolles et al. (2007) *Nature Reviews* 6:443-453. The mechanism allows for the specific and profound reduction of proteins and mRNA.

Briefly, double-stranded RNA (dsRNA) is synthesized with a sequence complementary to a gene of interest and introduced into a cell or organism, where the dsRNA is recognized as exogenous genetic material and activates the RNAi pathway. If the exogenous dsRNA is relatively long, it will be cleaved into small interfering RNAs (siRNAs). Alternatively, if the exogenous dsRNA is relatively short (about 30 base pairs or less), cleavage does not occur, the exogenous dsRNA itself acts as the siRNA substrate, and complications arising from activation of innate immunity defenses are avoided. In both cases, the siRNA becomes incorporated into an RNA-induced silencing complex (RISC) followed by unwinding of the double stranded siRNA into two strands. One of these strands, the "sense" strand (also known as the "passenger" strand), is discarded. The other strand, the "guide" strand (also known as the "antisense" strand) recognizes target sites to direct mRNA cleavage, thereby silencing its message. A similar RNAi mechanism involves microRNAs (miRNAs) deriving from imperfectly paired non-coding hairpin RNA structures.

Through the specific targeting of genes, RNAi-based therapies have the ability to substantially block the production of undesired proteins. Thus, in diseases and conditions attributable to the undesired or over expression of certain proteins, RNAi-based therapies represent a potentially powerful and important approach.

Despite the great promise of RNAi-based therapies, there remains a problem of the relative short half life of these therapeutics in vivo. There remains a need for better and improved versions of siNA in order to bring the RNAi-based therapies to fruition.

SUMMARY OF THE INVENTION

Accordingly, in one or more embodiments of the invention, a conjugate is provided, the conjugate comprising a residue of a siNA covalently attached to a water-soluble polymer.

In one or more embodiments of the invention, a conjugate is provided, the conjugate comprising a residue of a siNA covalently attached, either directly or through a spacer moiety comprised of one or more atoms, to a water-soluble polymer, wherein the siNA is attached to the water-soluble polymer or spacer moiety via an amine linkage.

In one or more embodiments of the invention, a conjugate is provided, the conjugate comprising a residue of a siNA covalently attached, either directly or through a spacer moiety comprised of one or more atoms, to a water-soluble polymer, wherein the siNA is attached to the water-soluble polymer or spacer moiety via an amide linkage.

In further embodiments of the above-described embodiments, the conjugates comprise a targeting moiety that delivers the conjugate to the targeted site in the body.

In one or more embodiments of the invention, a method for delivering a conjugate is provided, the method comprising the step of subcutaneously administering to the patient a composition comprised of a conjugate of a residue of a siNA and a water-soluble polymer.

DETAILED DESCRIPTION OF THE INVENTION

Figure 1:
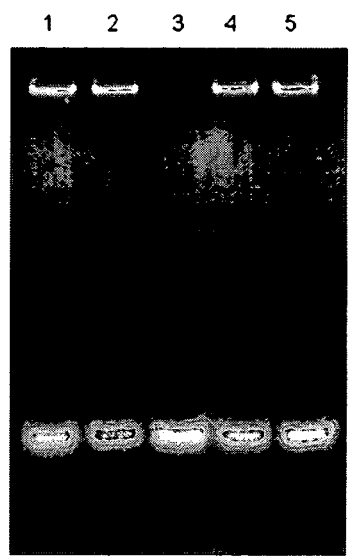
FIG. 1 is a representation of a gel as further described in Example 1.

As used herein, the singular forms "a," "an," and "the" include the plural reference unless the context clearly dictates otherwise. Thus, for example, reference to "siNA" includes a single siNA as well as two or more of the same or different siNAs, reference to an excipient refers to a single excipient as well as two or more of the same or different excipients, and the like.

Before further discussion, a definition of the following terms will aid in the understanding of the present invention.

In describing and claiming one or more embodiments of the present invention, the following terminology will be used in accordance with the definitions described below.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "—(OCH$_2$CH$_2$)$_n$—" where (n) is 2 to 4000. As used herein, PEG also includes "—CH$_2$CH$_2$—O (CH$_2$CH$_2$O)$_n$—CH$_2$CH$_2$—" and "—(OCH$_2$CH$_2$)$_n$O—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or C$_{1-20}$ alkoxy group, more preferably a C$_{1-10}$ alkoxy group, and still more preferably a C$_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in CH$_3$—O—(CH$_2$CH$_2$O)$_n$— and CH$_3$(OCH$_2$CH$_2$)$_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroyl-phosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

The term "targeting moiety" is used herein to refer to a molecular structure that increases localization of the conjugate described herein to a targeted area, e.g., enter, permeate, or penetrate a cell, or bind a receptor. Preferably, the targeting moiety comprises of vitamin, cofactor, antibody, antigen, receptor, DNA, RNA, sialyl Lewis X antigen, hyaluronic acid, sugars, cell specific lectins, steroid or steroid derivative, RGD peptide, cell penetrating or cell targeting moiety, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phosphatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a polymer segment and a siNA or an electrophile or nucleophile of a siNA. The spacer moiety may be hydrolytically stable or may include a physiologically releasable linkage (e.g., a hydrolyzable or enzymatically releasable linkage). Unless the context clearly dictates otherwise, a spacer moiety optionally exists between any two elements of a compound (e.g., the provided conjugates comprising a residue of siNA and water-soluble polymer can attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, substituted aryl, "Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "releasable" bond is a bond within a single molecular species that cleaves to result in two distinct molecular species. An exemplary releasable bond is a hydrolysable bond, which reacts with water (i.e., is hydrolyzed) under physiological conditions. The tendency of a bond to hydrolyze in water will depend not only on the general type of linkage connecting two central atoms but also on the substituents attached to these central atoms.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a polymer-siNA conjugate that is needed to provide a desired level of the conjugate (or corresponding unconjugated siNA) in the bloodstream or in the target tissue. The precise amount will depend upon numerous factors, e.g., the particular siNA, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "siNA," as used herein, refers to a moiety having human siNA activity. The siNA will also have at least one electrophilic group or nucleophilic group suitable for reaction with a polymeric reagent. In addition, the term "siNA" encompasses both the siNA prior to conjugation as well as the siNA residue following conjugation. As will be explained in further detail below, one of ordinary skill in the art can determine whether any given moiety has siNA activity. Further, the term "siNA" includes any nucleic acid molecule capable of mediating RNA interference ("RNAi") or gene silencing. The siNA includes, without limitation, a "short interfering nucleic acid" and includes short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, and post-transcriptional gene silencing RNA (ptg-sRNA). For example, the siRNA can be a double-stranded oligonucleotide molecule comprising a sense oligonucleotide and an antisense oligonucleotide, wherein the antisense region comprises complementarity to a target nucleic acid molecule. The siRNA can be a single-stranded hairpin oligonucleotide having self-complementary sense and antisense regions, wherein the antisense region comprises complementarity to a target nucleic acid molecule. As used herein, siRNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not contain any ribonucleotides (e.g., nucleotides having a 2'-OH group). The microRNAs can be of an agonist or antagonist and including, for example, antagomirs (as described in Krützfeldt et al. (2005) *Nature* 438(7068): 685-689). The siNA can be single stranded, double stranded or triple stranded.

In some instances, the siNA can be a sequence listed in the SEQUENCE LISTING included herewith.

In some instances, the siNA comprises a first sequence, for example, the antisense sequence of the siNA construct, complementary to a sequence or portion of sequence comprising a sequence represented by GenBank Accession Nos. shown in Table I of U.S. Patent Application Publication No. 2007/0160980 A1, or other sequence listed in that publication.

Further exemplary siNA is a siNA described in one or more of WO07/121,947, WO07/121,956, WO07/084,684, WO06/069782, WO06/023544, WO05/105152, WO05/000320, WO04/035615, European Patent and/or Application Nos. EP1857547, EP1771206, EP1527176, EP1638580, EP1551868, EP1536827, EP1527176, U.S. Patent Application Publication Nos. 2004/0180351 and 2005/0043263.

Still further exemplary siNA is siNA described in one or more of U.S. Pat. Nos. 5,898,031, 6,107,094, 7,056,704, 7,078,196, European Patent and Application Nos. EP1144623, EP1214945, EP1352061, German Patent 20023125, and U.S. Patent Application Publication Nos. 2005/0176667, 2005/0186591, 2005/0288244, 2006/0008822, 2006/0035254, 2006/0287260, 2007/0054279, 2007/0161595, 2007/0185050, 2007/0197460, 2007/0213292, 2007/0275465 and 2008/0194512.

Still further exemplary siNA is siNA described in one or more of the following U.S. Patent Application Publication Nos. 2005/0244858, 2005/0277610 and 2007/0265220.

Still further exemplary siNA is siNA described in one or more of the following publications Rose et al. (2005) *Nucleic Acid Res.* 33(13):4140-4156, Kim et al. (2005) *Nat. Biotechnol.* 23(2):222-226 and Amarzguioui et al. (2006) *Nature Protocol* 1(2):508-517.

Still further exemplary siNA is siNA described in one or more of the following U.S. Patent Application Publication Nos. 2002/0086356, 2003/0108923, 2007/0229266, 2004/

0259247, 2004/0259248, 2005/0026278, 2005/0059005, 2005/0182005, 2005/0227934, 2005/0234006, 2005/0234007, 2006/0166910, 2006/0212950, 2007/0003960, 2007/0003961, 2007/0003962, 2007/0003963, 2007/0093445 and 2007/0287179.

Still further exemplary siNA is siNA described in one or more of the following U.S. Patent Application Publication Nos. 2003/0190654, 2004/0001811, 2004/0038921, 2004/0053875, 2004/0072779, 2004/0091457, 2004/0102408, 2004/0121348, 2004/0126791, 2004/0175703, 2005/0074757, 2005/0100907 and 2008/0070856.

Still further exemplary siNA is siNA described in one or more of the following U.S. Patent Application Publication Nos. 2006/0014289, 2006/0035815, 2006/0122137, 2006/0142230, 2006/0160123, 2007/0155658, 2007/0172430, 2007/0213257, 2007/0213293, 2007/0254362, 2007/0269892, 2007/0275923, 2007/0276134, 2007/0281900, 2007/0293449, 2007/0293657 and 2008/0076701.

By "inhibit" or "down regulate" it is meant that the activity of a gene expression product or level of RNAs or equivalent RNAs encoding one or more gene products is reduced below that observed in the absence of the nucleic acid molecule. In one embodiment, inhibition with a siRNA molecule preferably is below that level observed in the presence of an inactive or attenuated molecule that is unable to mediate an RNAi response. In another embodiment, inhibition of gene expression with the siRNA molecule included as part of the instant invention is greater in the presence of the siRNA molecule than in its absence.

By "RNA" is meant a molecule comprising at least one ribonucleotide residue. By "ribonucleotide" is meant a nucleotide with a hydroxyl group at the 2' position of a β-D-ribo-furanose moiety. The terms include triple-stranded RNA, double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a siRNA or internally (e.g. capped structures), for example, at one or more nucleotides of the RNA. Nucleotides in the RNA molecules of the instant invention can also comprise non-standard nucleotides, such as non-naturally occurring nucleotides or chemically synthesized nucleotides or deoxy-nucleotides. These altered RNAs can be referred to as analogs or analogs of naturally-occurring RNA.

By "gene" and "target gene" and "target nucleic acid" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

"Optional" and "optionally" means that the subsequently described circumstance may or may not occur, so that the description includes instances where the circumstance occurs and instances where it does not. Thus, for example, a composition comprising an "optional excipient" includes compositions comprising one or more excipient as well as compositions any excipient.

The term "patient," refers to a living organism suffering from or prone to a condition that can be prevented or treated by administration of an active agent (e.g., siNA-containing conjugate), and includes both humans and animals. The term "subject" refers to a living organism suffering from or prone to a condition that can be prevented or treated through RNAi.

"Optional" or "optionally" means that the subsequently described circumstance may or may not occur, so that the description includes instances where the circumstance occurs and instances where it does not.

As used herein, an "excipient" is a component of a pharmaceutical composition that does not have RNAi activity. Further, "excipients" such as buffers, sugars, amino acids, and so forth are intended components of a pharmaceutical composition and stand in contrast to unintended components of a composition such as impurities.

A "therapeutically effective amount" is an amount of siNA (e.g., sirNA) construct required to provide a desired therapeutic effect. The exact amount required will vary from subject to subject and will otherwise be influenced by a number of factors, as will be explained in further detail below. An appropriate "therapeutically effective amount," however, in any individual case can be determined by one of ordinary skill in the art.

The term "substantially" refers to a system in which greater than 50% of the stated condition is satisfied. For instance, greater than 85%, greater than 92%, or greater than 96% of the condition may be satisfied.

Turning to one or more embodiments of the invention, a conjugate is provided, the conjugate comprising a residue of siNA covalently attached (either directly or through a spacer moiety) to a water-soluble polymer. The conjugates of the invention will have one or more of the following features.

siNAs

Turning to exemplary aspects of the invention, the compositions include one or more siNA, which may take several forms. siNAs may be of a length of about 7 to 50 nucleotides (each strand of a single stranded, double stranded and triple stranded siNA is independently of from about 7 to 50 nucleotides in length), e.g., one of the following nucleotide lengths: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some instances, the nucleotide length satisfies one or more of the following ranges: from 10 to 30; from 15 to 25; from 15 to 30; from 26 to 28; from 15 to 26; from 27 to 50; from 27 to 30; and from 10 to 20. Many siNAs are known in the art. siNAs, particularly in their single-stranded form and individual strands of a double-stranded or triple stranded siNA, generally have the ability to bind to a target with a $K_D$ of about 0.1 nM to about 100 nM.

In one or more embodiments, the siNA is a siRNA comprising a double-stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides, whereby said second stretch is at least partially identical to a target nucleic acid, and, optionally, one or more of the following apply: (i) the first stretch and/or the second stretch have a length of 15 to 23 nucleotides (e.g., 15, 16, 17, 18, 19, 20, 21 or 23 nucleotides); (ii) at least one of the two strands has an overhang of at least one nucleotide at the 5'-end or the 3'-end (preferably consisting of at least one nucleotide which is selected from the group comprising ribonucleotides and desoxyribonucleotides); (iii) a 2' modification (preferably selected from the group comprising amino, fluoro, methoxy, alkoxy and alkyl modifications; (iv)

a 3' modification (preferably an inverted nucleotide); (v) said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides; (vi) the first strand and the target nucleic acid comprises at least 15 nucleotides wherein there is one mismatch or two mismatches between said first strand and the target nucleic acid forming said double-stranded structure; (vii) the first strand and the second strand are linked by a loop structure. In some instances, it is preferred that the double-stranded structure is blunt ended on both sides of a double-stranded structure. In other instances, it is preferred that the double-stranded structure is blunt ended on the double-stranded structure which is defined by the 5'-end of the first strand and the 3'-end of the second strand. In still other instances, it is preferred that the double-stranded structure is blunt ended on the double stranded structure which is defined by the 3'-end of the first strand and the 5'-end of the second strand.

In one or more embodiments of the invention, the modification(s) included within an oligonucleotide that is an siNA can be present such that a pattern of the modification(s) is apparent or can be present such that a pattern of the modification(s) is not apparent. As would be understood, it is not possible to understand whether a pattern of modification(s) within an oligonucleotide is present based on only modification(s) of a single nucleotide within the oligonucleotide; consequently, it is necessary to demonstrate any pattern within a stretch of oligonucleotides.

This discussion of a pattern (and lack of a pattern) of modifications will focus on a modified nucleotide wherein a methoxy group is formed via methylation of the 2'-OH-group of the ribose moiety of the nucleotide (i.e., a 2'-O-methyl modification); this disclosure relating to patterns (or lack of patterns) of modifications, however, applies to any given modification as in the context of discussing the pattern (or lack of the pattern), any modification can be substituted for 2'-O-methyl modification).

In one or more embodiments, a pattern arises within a stretch of oligonucleotides such that each nucleotide within a stretch of nucleotides within the siNA alternates between 2'-O-methyl modified and non-2'-O-methyl modified. In one or more embodiments, however, a stretch of oligonucleotides will not demonstrate a pattern wherein a stretch of nucleotides within the siNA alternates between 2'-O-methyl modified and non-2'-O-methyl modified nucleotides. In an convention wherein "M" is a 2'-O-methyl modified nucleotide and "O" is a non-2'-O-methyl modified nucleotide, the following arrangement is considered as exhibiting a pattern: MOMOMOMOM, while the following arrangements are considered as not exhibiting a pattern: MOOOMOMOM; MOMOOOMOM; MOMOMOMOO; MOOOOOMOM; MOMOOOOOO; MOOOOOMOM; MOMOOOOOO; MMOMMOMMO; MOOMMOMMO; MOMOOOMMO; MOMOMOOOM; MMMOMOMOM; MOMMMOMOM; MOMOMMMOM; MOMOMOMMO; MOMOMOMOO; MMMOOMOMO; MMMOOOMOM; MMMOOOOMO; MMMOOOOOM; MMOMMOMOO; MMOMOMMOM; MMMMOMMMM; MMOMMMOMM; MOMMOM-MMO; MOMOMMOMM; MOMOMMMOO; MOMOM-MMOM; MOOMOOOMM; MOMOMMMO; MOMOOOOMM; MMOOOMOMM; MOOOMOMMO; MMMMMMOMM; MOMMMMMOM; OOMOMOMOM; OOOOMOMOM; OOMOOOMOM; OOMOMOMOO; OOOOOOMOM; OOMOOOOO; OOOOOOMOM; OOMOOOOOO; OMOMMOMMO; OOOMMOMMO; OOMOOOMMO; OOMOMOOOM; OMMOMOMOM; OOMMMOMOM; OOMOMMMOM; OOMOMOMMO; OOMOMOMOO; OMMOOMOMO; OMMOOOMOM; OMMOOOOMO; OMMOOOOOM; OMOOOMMOO; OMOMOMMOM; OMMMOMMMM; OMOMMMOMM; OOMMOMMMO; OOMOMOMM; OOMOMMMOO; OOMOMMMOM; OOOMOOOMM; OOMOOMMMO; OOMOOOOMM; OMOOOMOMM; OOOOMMOMO; OMMMMMOMM; and OOMMMMMOM. Of course, other arrangements are possible that similarly do not evidence a pattern. In another embodiment, the modified nucleotide comprises a 2'-fluoro modification.

The siNA is preferably targeted against a gene (i.e., the "target gene" or "target nucleic acid") selected from the group comprising structural genes, housekeeping genes, transcription factors, motility factors, cell cycle factors, cell cycle inhibitors, enzymes, growth factors, cytokines and tumor suppressors.

As will be explained in further detail below, the invention relates to polymer conjugates of siNAs. The polymer selected is typically water soluble so that the siNA to which it is attached does not precipitate in an aqueous environment, such as a physiological environment. The polymer selected is usually modified to have a one or more reactive groups, such as an active ester, carbonate or aldehyde. The polymer may be of any molecular weight, and typically between a weight-average molecular weight of 500 Daltons and a weight-average molecular weight of about 100,000 Daltons (the term "about" indicating that in preparations of a water soluble polymer, some molecules will weigh more, some less, than the stated molecular weight), and may be branched or unbranched. The polymers each typically have a weight-average molecular weight satisfying one or more of the following ranges: from about 2,000 Daltons to about 100,000 Daltons; from about 3,000 Daltons to about 50,000 Daltons; from about 5,000 Da to about 40,000 Daltons; and from about 20,000 Daltons to about 35,000 Daltons.

Suitable water-soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6,000 Daltons), cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. In one or more embodiments, it is preferred that the water-soluble polymer is not lactosylated poly(ethylene glycol) (e.g., a "lactose-PEG-siNA" construct).

In general, chemical derivatization may be performed under any suitable condition used to react a siNA with an activated polymer molecule. Methods for preparing chemical derivatives of polypeptides will generally comprise (a) reacting the siNA with the activated polymer molecule (such as a reactive ester, carbonate, or aldehyde derivative of the polymer molecule) under conditions whereby the siNA becomes covalently attached to the polymer. In one embodiment, the siNA may have a single polymer molecule attached thereto, although multiple polymers (e.g., two, three, four, and so on) attached to a single siNA are also contemplated.

siNA may be purchased from a commercial source or may be synthetically produced. For example siRNA can be purchased from Applied Biosystems (Foster City, Calif.) and Thermo Fisher Scientific Inc. (Waltham, Mass.). Those of ordinary skill in the art can prepare synthetic versions of siNA based on the references cited herein and elsewhere in the literature. For further details and a discussion of the synthesis of siRNA molecules in general see, U.S. Patent Application Publication No. 2003/0206887.

The Water-Soluble Polymer

As previously discussed, each conjugate comprises a siNA attached to a water-soluble polymer. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an siNA) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic water-soluble polymer is biocompatible and nonimmunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), hydroxyalkyl starch, and combinations of any of the foregoing.

With respect to hydroxyalkyl starch (HAS), these sugars represent a water-soluble polymer useful for the present invention. Typical of HAS is hydroxethyl starch, which is a substituted derivative of the carbohydrate polymer amylopectin which occurs in maize starch in a concentration of up to 95%. Amylopectin consists of glucose units, wherein the main chains have $\alpha$-1,4-glycosidic bonds, but $\alpha$-1,6-glycosidic bonds are present at the branching sites. Methods for activating hydroxyalkyl starch (such as hydroxyethyl starch) for facile attachment to molecules are described in U.S. Patent Application Publication No. 2006/0188472.

The polymer is not limited to a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the siNA. Thus, a polymeric reagent will possess a reactive group for reaction with the siNA. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGs will typically comprise a number of ($OCH_2CH_2$) monomers [or ($CH_2CH_2O$) monomers, depending on how the PEG is defined]. As used throughout the description, the number of repeating units is identified by the subscript "n" in "($OCH_2CH_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower $C_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy ($-OCH_3$) group (or $-CH_3$, again depending on how the PEG is defined), while the other terminus is a hydroxyl or other functional group that can be optionally chemically modified.

In one form useful in one or more embodiments of the present invention, free or unbound PEG is a linear polymer terminated at each end with hydroxyl groups:

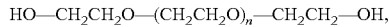
HO—$CH_2CH_2O$—($CH_2CH_2O$)$_n$—$CH_2CH_2$—OH, wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

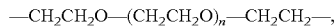
—$CH_2CH_2O$—($CH_2CH_2O$)$_n$—$CH_2CH_2$—, wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below:

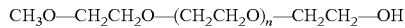
$CH_3O$—$CH_2CH_2O$—($CH_2CH_2O$)$_n$—$CH_2CH_2$—OH wherein (n) is as described above.

Multi-armed or branched PEG molecules, such as those described in U.S. Pat. No. 5,932,462, can also be used as the PEG polymer. For example, PEG can have the structure:

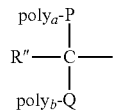

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine. Depending on the specific siNA used, the reactive ester functional group of the disubstituted lysine may be further modified to form a functional group suitable for reaction with the target group within the siNA.

In addition, the PEG can comprise a forked PEG. An example of a forked PEG is represented by the following structure:

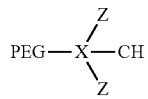

wherein: X is a spacer moiety of one or more atoms and each Z is an activated terminal group linked to CH by a chain of atoms of defined length. U.S. Pat. No. 7,223,803 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages (also referred to as "releasable" "linkages") in the polymer, including any of the above-described polymers. For example, PEG can be prepared with ester linkages in the polymer that are subject to hydrolysis. As shown below, this hydrolysis results in cleavage of the polymer into fragments of lower molecular weight:

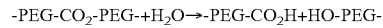
-PEG-$CO_2$-PEG-+$H_2O$→-PEG-$CO_2$H+HO-PEG-

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., a phosphoramidite group introduced at the end of a polymer, and a 5' hydroxyl group of an oligonucleotide.

Such optional features of the conjugate, e.g., the introduction of one or more degradable linkages into the polymer chain, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is hydrolyzed to generate a bioactive conjugate possessing a portion of the original PEG chain. In this way, the properties of the conjugate can be more effectively tailored to balance the bioactivity of the conjugate over time.

The water-soluble polymer associated with the conjugate can also be "releasable" (also referred to as "cleavable"). That is, the water-soluble polymer is released (either through hydrolysis, enzymatic processes, or otherwise), thereby resulting in the unconjugated siNA. In some instances, releasable polymers detach from the siNA in vivo without leaving any fragment of the water-soluble polymer or spacer moiety. In other instances, releaseable polymers detach from the siNA in vivo leaving a relatively small fragment (e.g., a succinate tag) from the water-soluble polymer. An exemplary releasable polymer includes one that attaches to the siNA via a carbonate linkage.

Those of ordinary skill in the art will recognize that the foregoing discussion concerning nonpeptidic and water-soluble polymers is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

As described above, a conjugate of the invention comprises a water-soluble polymer covalently attached to a siNA. Typically, for any given conjugate, there will be one to three water-soluble polymers covalently attached to one or more siNA. In some instances, however, the conjugate may have 1, 2, 3, 4, 5, 6, 7, 8 or more water-soluble polymers individually attached to a siNA.

The particular linkage within the moiety having siNA activity and the polymer depends on a number of factors. Such factors include, for example, the particular linkage chemistry employed, the particular siNA, the available functional groups within the siNA (either for attachment to a polymer or conversion to a suitable attachment site), the presence of additional reactive functional groups within the siNA, and the like.

The conjugates of the invention can be, although not necessarily, prodrugs, meaning that the linkage between the polymer and the siNA is releasable (e.g., hydrolyzable) to allow release of the parent moiety. Such linkages can be readily prepared by appropriate modification of either the siNA and/or the polymeric reagent using coupling methods commonly employed in the art. Most preferred for releasable linkages, however, are hydrolyzable linkages that are readily formed by reaction of a suitably activated polymer with a non-modified functional group contained within the moiety having siNA activity.

Alternatively, a hydrolytically stable linkage, such as an amide, urethane (also known as carbamate), amine, thioether (also known as sulfide), or urea (also known as carbamide) linkage can also be employed as the linkage for coupling the siNA. Again, preferred hydrolytically stable linkages include amines and amides. In one approach, a water-soluble polymer bearing an activated ester can be reacted with an amine group on the siNA to thereby result in an amide linkage.

In one or more embodiments, the conjugates of the invention further comprise a targeting moiety. Targeting moiety may comprise of, but is not limited to, an antibody or a fragment of an antibody, a protein or a fragment thereof, a receptor or a subunit thereof, a peptide, a lipid, a carbohydrate, a polymer, a radiolabel, or other suitable targeting moiety. For example, an antibody to a cell surface receptor or the receptor's ligand may be used as a targeting moiety that would deliver the conjugate to cells expressing the receptor on its surface. Similarly, using ApoB protein as target would deliver the siNA-conjugates to cells that express LDL receptor. Other examples of targeting moieties and their targets include: glucose or mannose-terminal glycoproteins for macrophages; galactose-terminal glycoproteins for hepatocytes; phosphovitellogenins for developing oocyte; fibrin for epithelial cells; and insulin and/or other hormones and transferring for various cell types. Once bound to a receptor or to the cell surface, the conjugates of the invention may be endocytosed, either by receptor-mediated endocytosis, pinocytosis, clathrin-mediated endocytosis, caveolae-mediated endocytosis, or some other mechanism. The endosomes (or commonly referred to as "vesicles"), containing the siNA conjugates and the targeting moiety may fuse with other vesicles, such as lysozymes, phagosomes, storage vesicles, or uncoupling vesicles called the compartment of uncoupling receptor and ligand (CURL). CURLs are characterized by an internal pH of ~5.0. In some embodiments, the conjugates possess a releasable linkage that is susceptible to a low pH and hence release the siNA from the conjugate. In other instances, the releasable linkage of the siNA-polymer conjugate may be susceptible to high or low pH, temperature, reducing or oxidizing environments, enzymes such as proteases, nucleases, esterases, lipases, and others present in the vesicles. Eventually, these vesicles may fuse with other vesicles or dissolve and release their contents in the cytoplasm, thus delivering the siNA to the intended cell and its cytoplasm. Thus, using the various releasable or cleavable linkages that are described herein; siNA-polymer conjugates comprising a targeting moiety are prepared that target and deliver siNA to desired cell type, or tissue.

The conjugates (as opposed to an unconjugated siNA) may or may not possess a measurable degree of RNAi activity. That is to say, a polymer-siNA conjugate in accordance with the invention will possesses anywhere from about 0.1% to about 100% of the bioactivity of the unmodified parent siNA. In some instances, the polymer-siNA conjugates may possess greater than 100% bioactivity of the unmodified parent siNA. Preferably, conjugates possessing little or no siNA activity contain a releasable linkage connecting the polymer to the moiety, so that regardless of the lack (or relatively lack) of activity in the conjugate, the active parent molecule (or a derivative thereof) is released upon aqueous-induced cleavage of the releasable linkage. Such activity may be determined using a suitable in-vivo or in-vitro model, depending upon the known activity of the particular moiety having RNAi activity being employed.

For conjugates possessing a hydrolytically stable linkage that couples the moiety having siNA activity to the polymer, the conjugate will typically possess a measurable degree of bioactivity. For instance, such conjugates are typically characterized as having a bioactivity satisfying one or more of the following percentages relative to that of the unconjugated siNA: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those well known in the art). Preferably, conjugates having a hydrolytically stable linkage (e.g., an amine or amide linkage) will possess at least some degree of the bioactivity of the unmodified parent moiety having siNA activity.

Exemplary conjugates in accordance with the invention will now be described.

Amino groups on siNA provide a point of attachment between the siNA and the water-soluble polymer. The siNA can, in some instances, be provided and otherwise manufactured with an amino group (such as having a aminohexyl [i.e., —$(CH_2)_6$—$NH_2$] or other aminoalkyl group. See, for example, Petrie et al. (1992) *Bioconjugate Chemistry* 3:85-87.

There are a number of examples of suitable polymeric reagents useful for forming covalent linkages with available amines of a siNA. Specific examples, along with the corresponding conjugate, are provided in Table 1, below. In the table, the variable (n) represents the number of repeating monomeric units and "—NH-(SiNA)" represents the residue of the siNA following conjugation to the polymeric reagent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

Amine-Selective Polymeric Reagents and the siNA Conjugate Formed Therefrom

| Polymeric Reagent | Corresponding Conjugate |
|---|---|
| mPEG-Oxycarbonylimidazole Reagent | Carbamate Linkage |
| mPEG Nitrophenyl Reagent | Carbamate Linkage |
| mPEG-Trichlorophenyl Carbonate Reagent | Carbamate Linkage |
| mPEG-Succinimidyl Reagent | Amide Linkage |
| Homobifunctional PEG-Succinimidyl Reagent | Amide Linkage |

TABLE 1-continued

Amine-Selective Polymeric Reagents and the siNA Conjugate Formed Therefrom

| Polymeric Reagent | Corresponding Conjugate |
|---|---|
| Biotin-(CH$_2$)$_4$—NH—CH$_2$CH$_2$—(OCH$_2$CH$_2$)$_n$—OCH$_2$C(O)—O—NHS<br>Heterobifunctional PEG-Succinimidyl Reagent | Biotin-(CH$_2$)$_4$—NH—CH$_2$CH$_2$—(OCH$_2$CH$_2$)$_n$—OCH$_2$CH$_2$C(O)NH—(siNA)<br>Amide Linkage |
| H$_3$C—(OCH$_2$CH$_2$)$_n$—O—CH$_2$CH$_2$—C(O)—O—NHS<br>mPEG-Succinimidyl Reagent | H$_3$C—(OCH$_2$CH$_2$)$_n$—O—CH$_2$CH$_2$—C(O)—NH—(siNA)<br>Amide Linkage |
| H$_3$CO—(CH$_2$CH$_2$O)$_n$—CH$_2$CH$_2$NH—C(O)—CH$_2$CH$_2$—C(O)—O—NHS<br>mPEG-Succinimidyl Reagent | H$_3$CO—(CH$_2$CH$_2$O)$_n$—CH$_2$CH$_2$NH—C(O)—CH$_2$CH$_2$—C(O)—NH—(siNA)<br>Amide Linkage |
| H$_3$CO—(CH$_2$CH$_2$O)$_n$—CH$_2$CH$_2$S—CH$_2$CH$_2$—C(O)—O—NHS<br>mPEG Succinimidyl Reagent | H$_3$CO—(CH$_2$CH$_2$O)$_n$—CH$_2$CH$_2$S—CH$_2$CH$_2$—C(O)—NH—(siNA)<br>Amide Linkage |

TABLE 1-continued

Amine-Selective Polymeric Reagents and the siNA Conjugate Formed Therefrom

| Polymeric Reagent | Corresponding Conjugate |
|---|---|
| H₃C—(OCH₂CH₂)ₙ—O—CH₂CH₂—C(=O)—O—N(succinimidyl)<br><br>mPEG-Succinimidyl Reagent | H₃C—(OCH₂CH₂)ₙ—O—CH₂CH₂—C(=O)—NH—(siNA)<br><br>Amide Linkage |
| H₃C—(OCH₂CH₂)ₙ—O—C(=O)—O-benzotriazole<br><br>mPEG-Benzotriazole Carbonate Reagent | H₃C—(OCH₂CH₂)ₙ—O—C(=O)—NH—(siNA)<br><br>Carbamate Linkage |
| H₃C—(OCH₂CH₂)ₙ—NH—C(=O)—O—(C₆H₄)—C(=O)—O—N(succinimidyl)<br><br>mPEG-Succinimidyl Reagent | H₃C—(OCH₂CH₂)ₙ—NH—C(=O)—O—(C₆H₄)—C(=O)—NH—(siNA)<br><br>Carbamate Linkage |
| H₃CO—(CH₂CH₂O)ₙ—C(=O)—O—(C₆H₄)—C(=O)—O—N(succinimidyl)<br><br>mPEG-Succinimidyl Reagent | H₃CO—(CH₂CH₂O)ₙ—C(=O)—O—(C₆H₄)—C(=O)—NH—(siNA)<br><br>Amide Linkage |

TABLE 1-continued

Amine-Selective Polymeric Reagents and the siNA Conjugate Formed Therefrom

| Polymeric Reagent | Corresponding Conjugate |
|---|---|
| <br>mPEG Succinimidyl Carbonate Reagent | <br>Carbamate Linkage |
| <br>Branched mPEG2-N-Hydroxysuccinimide Reagent | <br>Amide Linkage |
| 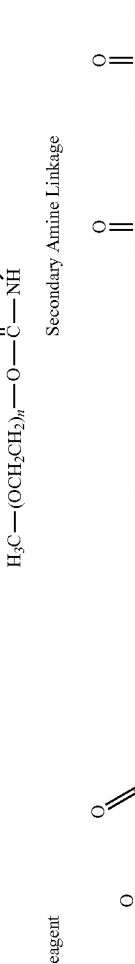<br>Branched mPEG2-Aldehyde Reagent | <br>Secondary Amine Linkage |
| 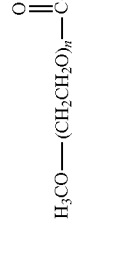<br>mPEG-Succinimidyl Reagent | 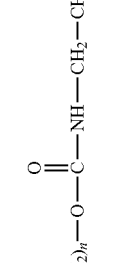<br>Amide Linkage |

TABLE 1-continued

Amine-Selective Polymeric Reagents and the siNA Conjugate Formed Therefrom

| Polymeric Reagent | Corresponding Conjugate |
|---|---|
| mPEG-Succinimidyl Reagent | Amide Linkage |
| Homobifunctional PEG-Succinimidyl Reagent | Amide Linkages |
| mPEG-Succinimidyl Reagent | Amide Linkage |
| Homobifunctional PEG-Succinimidyl Propionate Reagent | Amide Linkages |

TABLE 1-continued

Amine-Selective Polymeric Reagents and the siNA Conjugate Formed Therefrom

| Polymeric Reagent | Corresponding Conjugate |
|---|---|
| mPEG-Succinimidyl Reagent | Amide Linkage |
| Branched mPEG2-N-Hydroxysuccinimide Reagent | Amide Linkage |
| Branched mPEG2-N-Hydroxysuccinimide Reagent | Amide Linkage |
| mPEG-Thioester Reagent | Amide Linkage (typically to siNA having an N-terminal cysteine or histidine) |
| Homobifunctional PEG Propionaldehyde Reagent | Secondary Amine Linkages |

TABLE 1-continued

Amine-Selective Polymeric Reagents and the siNA Conjugate Formed Therefrom

| Polymeric Reagent | Corresponding Conjugate |
|---|---|
| $H_3C-(OCH_2CH_2)_n-O-CH_2CH_2-CHO$<br>mPEG Propionaldehyde Reagent | $H_3C-(OCH_2CH_2)_n-O-CH_2CH_2-CH_2-NH-(siNA)$<br>Secondary Amine Linkage |
| $OHC-CH_2CH_2CH_2-(OCH_2CH_2)_n-O-CH_2CH_2CH_2-CHO$<br>Homobifunctional PEG Butyraldehyde Reagent | $HN-CH_2CH_2CH_2-(OCH_2CH_2)_n-O-CH_2CH_2CH_2-CH_2-NH-(siNA)$<br>  (siNA)<br>Secondary Amine Linkages |
| $H_3C-(OCH_2CH_2)_n-O-CH_2CH_2CH_2-CHO$<br>mPEG Butyraldehyde Reagent | $H_3C-(OCH_2CH_2)_n-O-CH_2CH_2CH_2-CH_2-NH-(siNA)$<br>Secondary Amine Linkage |
| $H_3C-(OCH_2CH_2)_n-O-\overset{O}{C}-NH-(CH_2CH_2O)_4-CH_2CH_2CH_2-CHO$<br>mPEG Butyraldehyde Reagent | $H_3C-(OCH_2CH_2)_n-O-\overset{O}{C}-NH-(CH_2CH_2O)_4-CH_2CH_2CH_2-NH-(siNA)$<br>Secondary Amine Linkage |
| $\overset{O}{C}-(OCH_2CH_2)_n-O-\overset{O}{C}-NH-(CH_2CH_2O)_4-CH_2CH_2CH_2-CHO$<br>  HN<br>  |<br>  $(CH_2CH_2O)_4-CH_2CH_2CH_2-CH$<br>          ||<br>          O<br>Homobifunctional PEG Butyraldehyde Reagent | $\overset{O}{C}-(OCH_2CH_2)_n-O-\overset{O}{C}-NH-(CH_2CH_2O)_4-CH_2CH_2CH_2-NH-(siNA)$<br>  HN<br>  |<br>  $(CH_2CH_2O)_4-CH_2CH_2CH_2-NH-(siNA)$<br>Secondary Amine Linkages |
| $H_3C-(OCH_2CH_2)_n-O-\overset{O}{C}-NH-CH_2-CH_2-CH_2-CH_2$<br>                                    CH-CH_2CH_2CH<br>                                   |        ||<br>                                    O       O<br>                                    ||<br>$H_3C-(OCH_2CH_2)_n-O-\overset{O}{C}-NH$<br>Branched mPEG2 Butyraldehyde Reagent | $H_3C-(OCH_2CH_2)_n-O-\overset{O}{C}-NH-CH_2-CH_2-CH_2-CH_2$<br>                                    CH-CH_2CH_2CH_2-NH<br>                                    |                 |<br>                                    O              (siNA)<br>                                    ||<br>                                    C-NH-(CH_2CH_2O)_4-CH_2CH_2CH_2-NH<br>$H_3C-(OCH_2CH_2)_n-O-\overset{O}{C}-NH$<br>Secondary Amine Linkage |

TABLE 1-continued

Amine-Selective Polymeric Reagents and the siNA Conjugate Formed Therefrom

| Polymeric Reagent | Corresponding Conjugate |
|---|---|
| $H_3C-(OCH_2CH_2)_n-NH-\overset{O}{\underset{\|}{C}}-O-CH_2$<br>$H_3C-(OCH_2CH_2)_n-NH-\overset{O}{\underset{\|}{C}}-O-CH_2$<br>$\phantom{H_3C-(OCH_2CH_2)_n-NH-}HC-OCH_2-CH_2-CH_2-\overset{O}{\underset{\|}{C}}-NH-(CH_2CH_2O)_4-CH_2CH_2CH_2CH$<br>Branched mPEG2 Butyraldehyde Reagent | $H_3C-(OCH_2CH_2)_n-NH-\overset{O}{\underset{\|}{C}}-O-CH_2$<br>$H_3C-(OCH_2CH_2)_n-NH-\overset{O}{\underset{\|}{C}}-O-CH_2$<br>$\phantom{H_3C-(OCH_2CH_2)_n-NH-}HC-OCH_2CH_2CH_2-\overset{O}{\underset{\|}{C}}-NH-(CH_2CH_2O)_4-$<br>$\phantom{xxxxxxxxxxxxxxxxxxxxxxxxxxxxxxxxxxxxxxxxxxxxxxxxxxxxxxx}-CH_2CH_2CH_2CH_2-NH-(siNA)$<br>Secondary Amine Linkage |
| $H_3C-(OCH_2CH_2)_n-O-CH_2-\overset{OCH_2CH_3}{\underset{\|}{CH}}-OCH_2CH_3$<br>mPEG Acetal Reagent | $H_3C-(OCH_2CH_2)_n-O-CH_2CH_2-NH-(siNA)$<br>Secondary Amine Linkage |
| $H_3C-(OCH_2CH_2)_n-O-CH_2CH_2-\overset{O}{\underset{\|}{C}}-N\underset{\phantom{xx}}{\bigcirc}=O$<br>mPEG Piperidone Reagent | $H_3C-(OCH_2CH_2)_n-O-CH_2CH_2-\overset{O}{\underset{\|}{C}}-N\underset{\phantom{xx}}{\bigcirc}-NH-(siNA)$<br>Secondary Amine Linkage<br>(to a secondary carbon) |
| $H_3C-(OCH_2CH_2)_n-O-(CH_2)_{2-5}-\overset{O}{\underset{\|}{C}}-CH_3$<br>mPEG Methylketone Reagent | $H_3C-(OCH_2CH_2)_n-O-(CH_2)_{2-5}-\underset{\underset{CH_3}{\|}}{\overset{NH-(siNA)}{CH}}$<br>secondary amine linkage<br>(to a secondary carbon) |
| $H_3CO-(CH_2CH_2O)_n-\overset{O}{\underset{\underset{O}{\|}}{S}}-CH_2-CF_3$<br>mPEG tresylate Reagent | $H_3CO-(CH_2CH_2O)_n-CH_2CH_2-NH-(siNA)$<br>Secondary Amine Linkage |

TABLE 1-continued

Amine-Selective Polymeric Reagents and the siNA Conjugate Formed Therefrom

| Polymeric Reagent | Corresponding Conjugate |
|---|---|
| 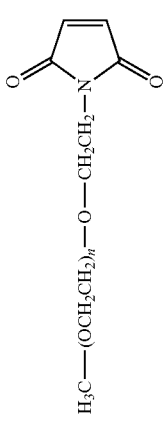<br>H$_3$C—(OCH$_2$CH$_2$)$_n$—O—CH$_2$CH$_2$—<br>mPEG Maleimide Reagent<br>(under certain reaction conditions such as pH > 8) | 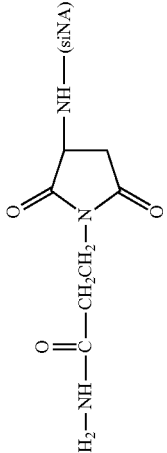<br>H$_3$C—(OCH$_2$CH$_2$)$_n$—O—CH$_2$CH$_2$—<br>Secondary Amine Linkage |
| 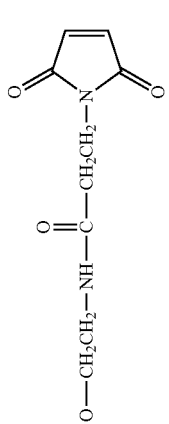<br>H$_3$C—(OCH$_2$CH$_2$)$_n$—O—CH$_2$CH$_2$—C(O)—NH—CH$_2$CH$_2$—<br>mPEG Maleimide Reagent<br>(under certain reaction conditions such as pH > 8) | 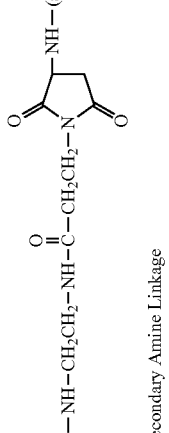<br>H$_3$C—(OCH$_2$CH$_2$)$_n$—O—CH$_2$CH$_2$—C(O)—NH—CH$_2$CH$_2$—<br>Secondary Amine Linkage |
| 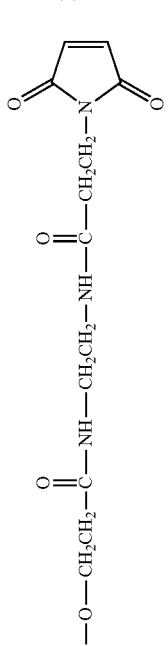<br>H$_3$C—(OCH$_2$CH$_2$)$_n$—O—CH$_2$CH$_2$—C(O)—NH—CH$_2$CH$_2$—NH—C(O)—CH$_2$CH$_2$—<br>mPEG Maleimide Reagent<br>(under certain reaction conditions such as pH > 8) | <br>H$_3$C—(OCH$_2$CH$_2$)$_n$—O—CH$_2$CH$_2$—C(O)—NH—CH$_2$CH$_2$—NH—C(O)—CH$_2$CH$_2$—<br>Secondary Amine Linkage |

TABLE 1-continued
Amine-Selective Polymeric Reagents and the siNA Conjugate Formed Therefrom
| Polymeric Reagent | Corresponding Conjugate |
|---|---|
| 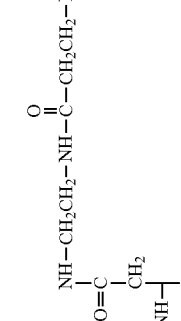 mPEG Forked Maleimide Reagent (under certain reaction conditions such as pH > 8) | 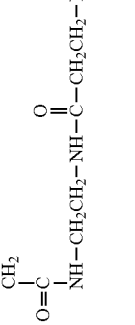 Secondary Amine Linkages |
|  branched mPEG2 Maleimide Reagent (under certain reaction conditions such as pH > 8) | 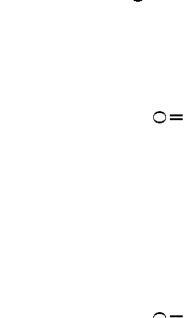 Secondary Amine Linkage |

TABLE 1-continued
Amine-Selective Polymeric Reagents and the siNA Conjugate Formed Therefrom
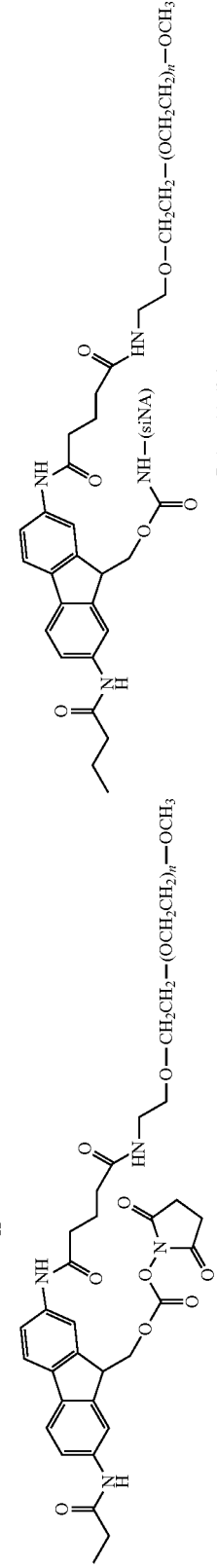

TABLE 1-continued

Amine-Selective Polymeric Reagents and the siNA Conjugate Formed Therefrom

| Polymeric Reagent | Corresponding Conjugate |
|---|---|

(Structures shown: fluorenyl-based NHS carbonate polymeric reagents with mPEG chains $CH_3O-(CH_2CH_2O)_n-CH_2CH_2-$ and their corresponding siNA conjugates with releasable linkages, where siNA is attached via NH group.)

Releasable linkage

Conjugation of a polymeric reagent to an amino group of a siNA can be accomplished by a variety of techniques. In one approach, a siNA can be conjugated to a polymeric reagent functionalized with a succinimidyl derivative (or other activated ester or carbonate group, wherein approaches similar to those described for these alternative activated ester group-containing polymeric reagents can be used). In this approach, the polymer bearing a succinimidyl derivative can be attached to the siNA in an aqueous media at a pH of 7 to 9.0, although using different reaction conditions (e.g., a lower pH such as 6 to 7, or different temperatures and/or less than 15° C.) can result in the attachment of the polymer to a different location on the siNA. In addition, an amide linkage can be formed reacting an amine-terminated non-peptidic, water-soluble polymer with a siNA bearing an activating a carboxylic acid group.

An exemplary conjugate comprises the following structure:

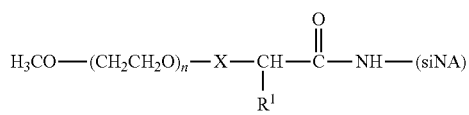

wherein:
(n) is an integer having a value of from 2 to 4000;
X is a spacer moiety;
$R^1$ is H or an organic radical (e.g., lower alkyl); and
siNA is a residue of a siNA.

Another exemplary conjugate of the present invention comprises the following structure:

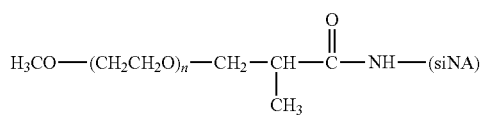

wherein (n) an integer having a value of from 2 to 4000 and siNA is a residue of a siNA.

Typical of another approach useful for conjugating the siNA to a polymeric reagent is use of reductive amination to conjugate a primary amine of a siNA with a polymeric reagent functionalized with a ketone, aldehyde or a hydrated form thereof (e.g., a ketone hydrate and aldehyde hydrate). In this approach, the primary amine from the siNA reacts with the carbonyl group of the aldehyde or ketone (or the corresponding hydroxyl-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus are possible) are possible, particularly with a polymer functionalized with a ketone or an alpha-methyl branched aldehyde and/or under specific reaction conditions (e.g., reduced pH).

Exemplary conjugates of the invention wherein the water-soluble polymer is in a branched form, will have the branched form of the water-soluble polymer comprise the following structure:

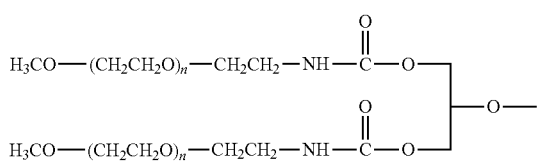

wherein each (n) is independently an integer having a value of from 2 to 4000.

Exemplary conjugates of the invention comprise the following structure:

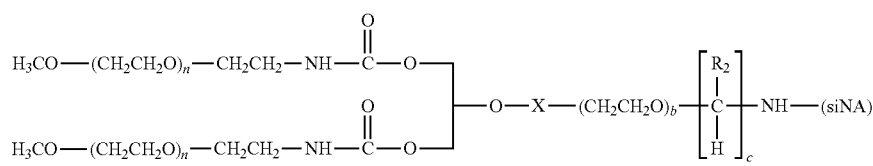

wherein:
each (n) is independently an integer having a value of from 2 to 4000;
X is spacer moiety;
(b) is an integer having a value 2 through 6;
(c) is an integer having a value 2 through 6;
$R^2$, in each occurrence, is independently H or lower alkyl; and
siNA is a residue of a siNA.

An exemplary conjugate of the invention comprises the following structure:

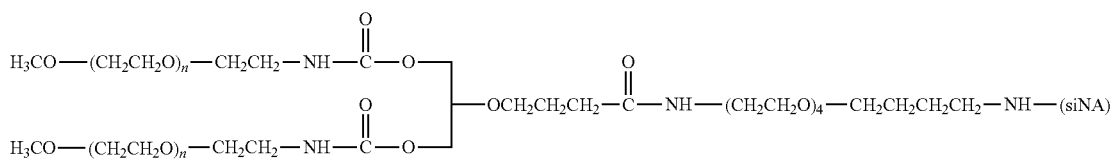

wherein:
    each (n) is independently an integer having a value of from 2 to 4000; and
    siNA is a residue of a siNA.

Another exemplary conjugate of the invention comprises the following structure:

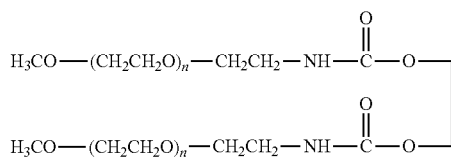

wherein:
    each (n) is independently an integer having a value of from 2 to 4000;
    (a) is either zero or one;
    X, when present, is a spacer moiety comprised of one or more atoms;
    (b') is zero or an integer having a value of one through ten;
    (c) is an integer having a value of one through ten;
    $R^2$, in each occurrence, is independently H or an organic radical;
    $R^3$, in each occurrence, is independently H or an organic radical; and
    siNA is a residue of a siNA.

An exemplary conjugate of the invention comprises the following structure:

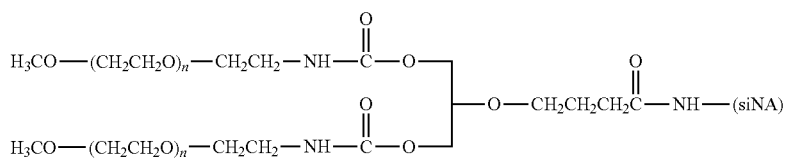

wherein:
    each (n) is independently an integer having a value of from 2 to 4000; and
    siNA is a residue of siNA.

Carboxyl groups represent another functional group that can serve as a point of attachment on the siNA. Structurally, the conjugate will comprise the following:

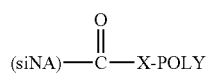

where (siNA) and the adjacent carbonyl group corresponds to the carboxyl-containing siNA, X is a linkage, preferably a heteroatom selected from O, N(H), and S, and POLY is a water-soluble polymer such as PEG, optionally terminating in an end-capping moiety.

The C(O)-X linkage results from the reaction between a polymeric derivative bearing a terminal functional group and a carboxyl-containing siNA. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at a carbonyl. Specific examples of water-soluble derivatives containing a hydrazide moiety, along with the corresponding conjugates, are provided in Table 2, below. In addition, any water-soluble derivative containing an activated ester (e.g., a succinimidyl group) can be converted to contain a hydrazide moiety by reacting the water-soluble polymer derivative containing the activated ester with hydrazine ($NH_2$—$NH_2$) or tert-butyl carbazate [$NH_2NHCO_2C(CH_3)_3$]. In the table, the variable (n) represents the number of repeating monomeric units and "=C-(SiNA)" represents the residue of the siNA following conjugation to the polymeric reagent. Optionally, the hydrazone linkage can be reduced using a suitable reducing agent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 2

Carboxyl-Selective Polymeric Reagents and the siNA Conjugate Formed Therefrom

| Polymeric Reagent | Corresponding Conjugate |
|---|---|
| $H_3CO-(CH_2CH_2O)_n CH_2CH_2-C(=O)-NH-NH_2$<br>mPEG-Hydrazine Reagent | $H_3CO-(CH_2CH_2O)_n CH_2CH_2-C(=O)-NH-N=C-(siNA)$<br>Hydrazone Linkage |
| $H_3CO-(CH_2CH_2O)_n CH_2CH_2-O-CH_2-C(=O)-NH-NH_2$<br>mPEG-Hydrazine Reagent | $H_3CO-(CH_2CH_2O)_n CH_2CH_2-O-CH_2-C(=O)-NH-N=C-(siNA)$<br>Hydrazone Linkage |
| $H_3CO-(CH_2CH_2O)_n CH_2CH_2-NH-C(=O)-NH-NH_2$<br>mPEG-Hydrazine Reagent | $H_3CO-(CH_2CH_2O)_n CH_2CH_2-NH-C(=O)-NH-N=C-(siNA)$<br>Hydrazone Linkage |
| $H_3CO-(CH_2CH_2O)_n CH_2CH_2-NH-NH-C(=O)-NH-NH_2$<br>mPEG-Hydrazine Reagent | $H_3CO-(CH_2CH_2O)_n CH_2CH_2-N(H)-NH-C(=O)-NH-N=C-(siNA)$<br>Hydrazone Linkage |
| $H_3CO-(CH_2CH_2O)_n CH_2CH_2-NH-C(=S)-NH-NH_2$<br>mPEG-Hydrazine Reagent | $H_3CO-(CH_2CH_2O)_n CH_2CH_2-NH-C(=S)-NH-N=C-(siNA)$<br>Hydrazone Linkage |
| $H_3CO-(CH_2CH_2O)_n CH_2CH_2-NH-NH-C(=S)-NH-NH_2$<br>mPEG-Hydrazine Reagent | $H_3CO-(CH_2CH_2O)_n CH_2CH_2-N(H)-NH-C(=S)-NH-N=C-(siNA)$<br>Hydrazone Linkage |
| $H_3CO-(CH_2CH_2O)_n CH_2CH_2-NH-C(=O)-NH-NH-C(=O)-NH-NH_2$<br>mPEG-Hydrazine Reagent | $H_3CO-(CH_2CH_2O)_n CH_2CH_2-NH-C(=O)-NH-NH-C(=O)-NH-N=C-(siNA)$<br>Hydrazone Linkage |
| $H_3CO-(CH_2CH_2O)_n CH_2CH_2-O-C(=O)-NH-NH_2$<br>mPEG-Hydrazine Reagent | $H_3CO-(CH_2CH_2O)_n CH_2CH_2-O-C(=O)-NH-N=C-(siNA)$<br>Hydrazone Linkage |

Thiol groups contained within the siNA can serve as effective sites of attachment for the water-soluble polymer. To the extent that a given siNA does not include a thiol, a thiol can be introduced via techniques known to those of ordinary skill in the art.

Specific examples of reagents, along with the corresponding conjugate, are provided in Table 3, below. In the table, the variable (n) represents the number of repeating monomeric units and "—S-(siNA)" represents the siNA residue following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

TABLE 3

Thiol-Selective Polymeric Reagents and the siNA Conjugate Formed Therefrom

| Polymeric Reagent | Corresponding Conjugate |
|---|---|
| $H_3C-(OCH_2CH_2)_n-O-CH_2CH_2-$ mPEG Maleimide Reagent | $H_3C-(OCH_2CH_2)_n-O-CH_2CH_2-$ (succinimide)-S-(siNA) Thioether Linkage |
| $H_3CO-(CH_2CH_2O)_n-CH_2CH_2-$ mPEG Maleimide Reagent | $H_3CO-(CH_2CH_2O)_n-CH_2CH_2-$ (succinimide)-S-(siNA) Thioether Linkage |
| $H_3CO-(CH_2CH_2O)_n-C(O)-NH-CH_2CH_2OCH_2CH_2OCH_2CH_2NH-C(O)-CH_2CH_2-$ mPEG Maleimide Reagent | $H_3CO-(CH_2CH_2O)_n-C(O)-NH-CH_2CH_2OCH_2CH_2OCH_2CH_2NH-C(O)-CH_2CH_2-$ (succinimide)-S-(siNA) Thioether Linkage |

TABLE 3-continued

Thiol-Selective Polymeric Reagents and the siNA Conjugate Formed Therefrom

| Polymeric Reagent | Corresponding Conjugate |
|---|---|
| Homobifunctional mPEG Maleimide Reagent | Thioether Linkages |
| mPEG Maleimide Reagent | Thioether Linkage |
| mPEG Maleimide Reagent | Thioether Linkage |

TABLE 3-continued
Thiol-Selective Polymeric Reagents and the siNA Conjugate Formed Therefrom
| Polymeric Reagent | Corresponding Conjugate |
|---|---|
|  mPEG Maleimide Reagent |  Thioether Linkage |
| 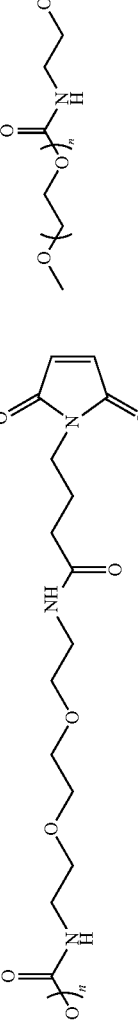 mPEG Forked Maleimide Reagent | 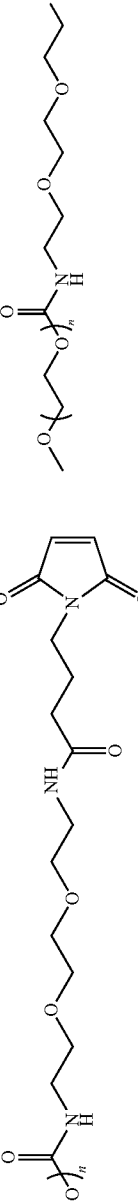 Thioether Linkage |

TABLE 3-continued

Thiol-Selective Polymeric Reagents and the siNA Conjugate Formed Therefrom

| Polymeric Reagent | Corresponding Conjugate |
|---|---|
| branched mPEG2 Maleimide Reagent | Thioether Linkage |
| branched mPEG2 Maleimide Reagent | Thioether Linkage |

TABLE 3-continued

Thiol-Selective Polymeric Reagents and the siNA Conjugate Formed Therefrom

| Polymeric Reagent | Corresponding Conjugate |
|---|---|
| Branched mPEG2 Forked Maleimide Reagent | Thioether Linkages |
| Branched mPEG2 Forked Maleimide Reagent | Thioether Linkages |

TABLE 3-continued

Thiol-Selective Polymeric Reagents and the siNA Conjugate Formed Therefrom

| Polymeric Reagent | Corresponding Conjugate |
|---|---|
| $H_3C-(OCH_2CH_2)_n-O-CH_2CH_2-S(=O)_2-CH=CH_2$<br>mPEG Vinyl Sulfone Reagent | $H_3C-(OCH_2CH_2)_n-O-CH_2CH_2-S(=O)_2-CH_2-CH_2-S-(siNA)$<br>Thioether Linkage |
| $H_3C-(OCH_2CH_2)_n-O-CH_2CH_2-C(=O)-NH-CH_2-CH_2-SH$<br>mPEG Thiol Reagent | $H_3C-(OCH_2CH_2)_n-O-CH_2CH_2-C(=O)-NH-CH_2-CH_2-S-S-(siNA)$<br>Disulfide Linkage |
| $HS-CH_2CH_2-NH-C(=O)-CH_2CH_2-(OCH_2CH_2)_n-C(=O)-NH-CH_2-CH_2-SH$<br>Homobifunctional PEG Thiol Reagent | $(siNA)S-S-CH_2CH_2-NH-C(=O)-CH_2CH_2-(OCH_2CH_2)_n-C(=O)-NH-CH_2CH_2-S-S-(siNA)$<br>Disulfide Linkages |
| $H_3CO-(CH_2CH_2O)_n-CH_2CH_2CH_2-S-S-\text{(2-pyridyl)}$<br>mPEG Disulfide Reagent | $H_3CO-(CH_2CH_2O)_n-CH_2CH_2CH_2-S-S-(siNA)$<br>Disulfide Linkage |
| $\text{(2-pyridyl)}-S-S-CH_2CH_2-(CH_2CH_2O)_n-CH_2CH_2CH_2-S-S-\text{(2-pyridyl)}$<br>Homobifunctional Disulfide Reagent | $(siNA)-S-S-CH_2CH_2-(CH_2CH_2O)_n-CH_2CH_2CH_2-S-S-(siNA)$<br>Disulfide Linkages |

With respect to conjugates formed from water-soluble polymers bearing one or more maleimide functional groups (regardless of whether the maleimide reacts with an amine or thiol group on the siNA), the corresponding maleamic acid form(s) of the water-soluble polymer can also react with the siNA. Under certain conditions (e.g., a pH of about 7-9 and in the presence of water), the maleimide ring will "open" to form the corresponding maleamic acid. The maleamic acid, in turn, can react with an amine or thiol group of a siNA. Exemplary maleamic acid-based reactions are schematically shown below. POLY represents the water-soluble polymer, and (siNA) represents the siNA.

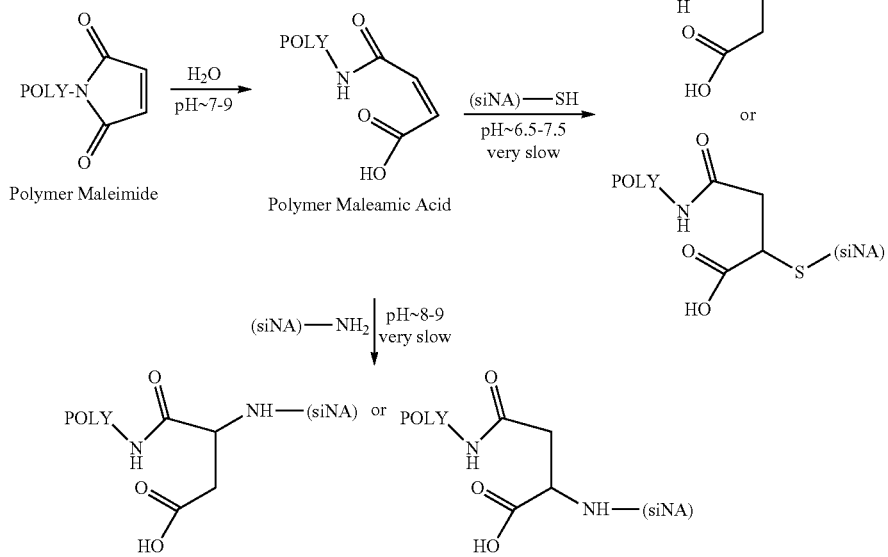

A representative conjugate in accordance with the invention can have the following structure:

POLY-$L_{0,1}$-C(O)Z—Y—S—S-(siNA)

wherein POLY is a water-soluble polymer, L is an optional linker, Z is a heteroatom selected from the group consisting of O, NH, and S, and Y is selected from the group consisting of $C_{2-10}$ alkyl, $C_{2-10}$ substituted alkyl, aryl, and substituted aryl, and (siNA) is a siNA. Polymeric reagents that can be reacted with a siNA and result in this type of conjugate are described in U.S. Patent Application Publication No. 2005/0014903.

As previously indicated, exemplary conjugates of the invention wherein the water-soluble polymer is in a branched form, will have the branched form of the water-soluble polymer comprise the following structure:

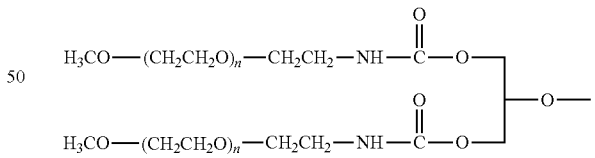

wherein each (n) is independently an integer having a value of from 2 to 4000.

Exemplary conjugates having a water-soluble polymer in branched form are prepared using the following reagent:

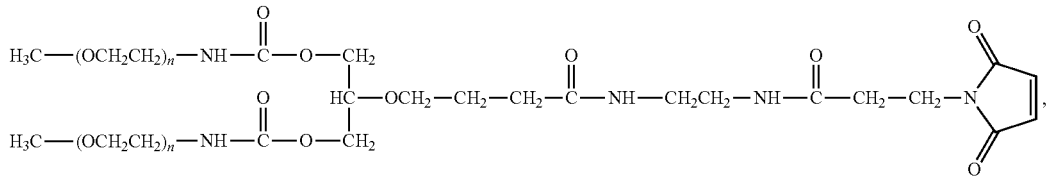

thereby forming a conjugate having the following structure:

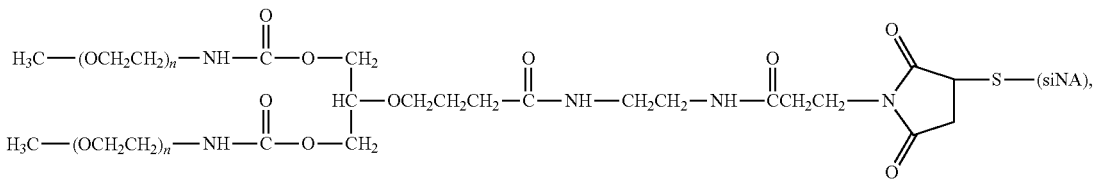

wherein:
(for each structure) each (n) is independently an integer having a value of from 2 to 4000; and
(siNA) is a residue of siNA.

An additional exemplary conjugate can be formed using a reagent:

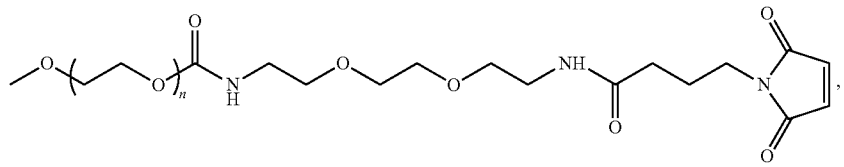

thereby forming a conjugate having the following structure:

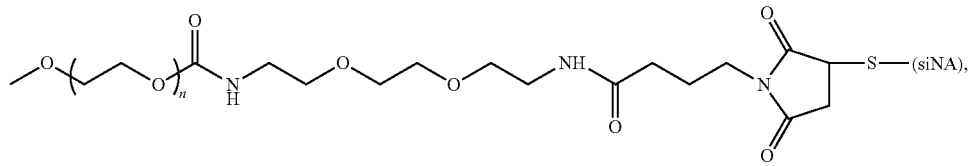

wherein:
(for each structure) (n) is independently an integer having a value of from 2 to 4000; and
siNA is a residue of siNA.

Conjugates can be formed using thiol-specific polymeric reagents in a number of ways and the invention is not limited in this regard. For example, the siNA—optionally in a suitable buffer (including amine-containing buffers, if desired)—is placed in an aqueous media at a pH of about 7-8 and the thiol-specific polymeric reagent is added at a molar excess. The reaction is allowed to proceed for about 0.5 to 2 hours, although reaction times of greater than 2 hours (e.g., 5 hours, 10 hours, 12 hours, and 24 hours) can be useful if PEGylation yields are determined to be relatively low. Exemplary polymeric reagents that can be used in this approach are polymeric reagents bearing a reactive group selected from the group consisting of maleimide, sulfone (e.g., vinyl sulfone), and thiol (e.g., functionalized thiols such as an ortho pyridinyl or "OPSS").

The conjugates can be formed from reagents bearing multiple polymer "arms" and functional groups.

For example, one such multiarm approach has the following formula:

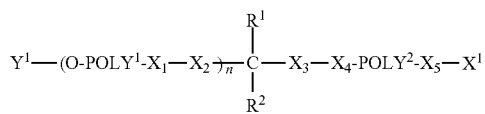

wherein:
as $X_1$, $X_2$, $X_3$, $X_4$, $X_5$ are each independently optional spacer moieties;
each POLY$^1$ is a water-soluble polymer (e.g., a PEG);
POLY$^2$ is a positively charged or neutral polymer (e.g., chitosan, polylysine, and polyethylenemine);
n is 1, 2, or 3;
R$^1$ is H or alkyl;
R$^2$ is H or alkyl;
Y$^1$ is H, lower alkyl, substituted alkyl, a fatty group (optionally substituted) including lipids (e.g., phospholipids, lipophilic vitamins, lipophilic coenzymes, or lipophilic antioxidants); and
X$^1$ is an endcapping group or spacer moiety connecting an siNA or a targeting moiety (e.g., folate, pemeterxed, RGD peptide, and cholesterol).

One specific example of the use of this structure follows. POLY$^1$ is a branched PEG polymer that includes a lipid or fatty group, Y$^1$, at a terminus of a branched PEG (POLY$^1$) and as POLY$^2$ is the positively charged polymer selected from the group consisting of a polylysine (such as a modified polylysine) and polyethyleneimine. Further, optional spacer moiety, X$_5$, is present and is a releasable linker, which, when X$^1$ is a spacer moiety connecting an siNA, provides for a release of the siNA. In addition, this structure can deliver the siNA as an unbound component in a composition as the negative charges of the siNA would be attracted to the positive charges of POLY$^2$. Depending on the complexity of the Y$^1$, and the molecular weight of the PEG in this example, the polymeric mixture in water could form a micelle.

Micelles are known to have useful drug delivery properties. See Kataoka et al. (1993) *J. Controlled Rel.* 24:119-132 and Husseini et al. (2002) *J Controlled Rel.* 83:302-304.

An exemplary structure following this approach is provided below.

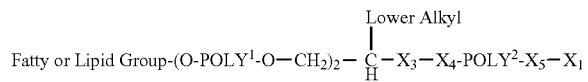

A second generic structure that will be applicable to siNA delivery is shown below. Methods for preparing the structure are described in U.S. Patent Application Publication No. 2007/0031371. While this structure is shown in a six-arm form which delivers up to six drug molecules, this structural type is also available in other numbers of arms, including two- and four-arm varieties.

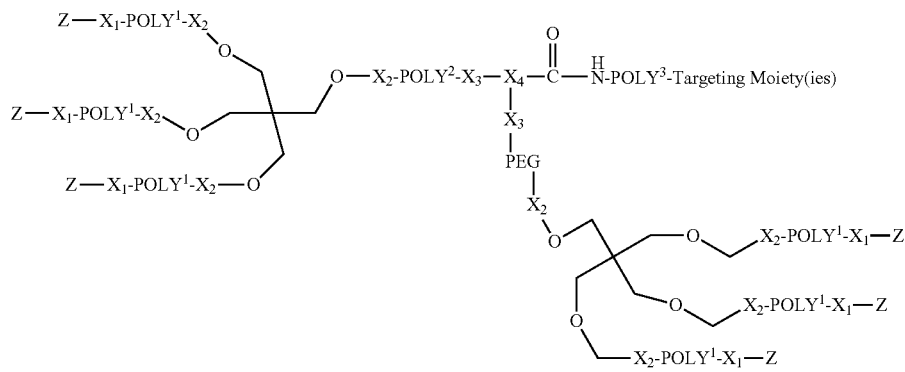

wherein:

$X_1$ is a degradable or releaseable spacer moiety or linker (e.g., ester, releasable carbamate, releasable disulfide, and releasable thioether);

each of $X_2$, $X_3$, $X_4$ is independently a stable spacer moiety;

each Z is a residue of a pharmacologically active agent (e.g., a siNA);

each $POLY^1$ is a water soluble polymer (e.g., a PEG);

$POLY^2$ is a water soluble oligomeric linker (e.g., a PEG, a polycationic polymer, and carbohydrate);

$POLY^3$ is a water soluble polymeric linker that is optionally positively charged (e.g., chitosan, polylysine, an polyethyleneimine); and each Targeting moiety is an organic or biologically active moiety that can binds to target and is selected to fit a specific delivery application (e.g., folate, pemeterxed and RGD peptide, or cholesterol).

The residue of the pharmacologically active agent, (Z) can also contain various structural motifs especially for siNA delivery (e.g., Z is a targeting moiety-Xn-Z- or Z-Xn-Targeting moiety-; where Xn may be a stable or releasable spacer moiety). Alternatively spacer moieties ($X_1$) could be polycationic moieties that form non-covalent ionic complex with the siNA drug.

A third generic multiarm structure is shown below. Methods for preparing the structure are described in U.S. Patent Application Publication No. 2007/0031371. This particular multiarm may have two or more arms depending on the functionality of the polypeptide linker (two or more amino acids, lysines in this example).

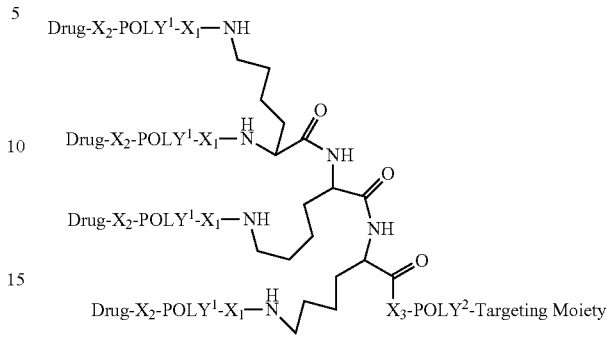

wherein:

Drug is a residue of a pharmacologically active agent drug that is released in vivo;

each $X_1$ is a stable spacer moeity;

$X_3$ is a stable spacer moeity;

$X_2$ is a releasable spacer moeity (e.g., ester, releasable carbamate, releasable disulfide, and releasable thioether);

each $POLY^1$ is a water soluble polymer (e.g., a PEG);

$POLY^2$ is neutral or, optionally, positively charged water soluble polymeric linker (e.g., a PEG, polycationic polymer, and carbohydrate); and Targeting moiety is an organic or biologically active moiety that can bind to a target and is selected to fit a specific delivery application.

Spacer moieties, end groups and targeting groups will include, in some cases, lipid or phospholipids moieties. Positively charged polymers may include polyamines or polymers containing positively charged amine groups. Releaseable linkers may be, for example, FMOC-based structures and esters.

Note that the pharmacologically active agent moiety (Drug) may also contain various structural motifs especially for siNA delivery (e.g., Drug=TM-Lx-Drug- or Drug-Lx-TM-; where Lx may be a stable or releasable linker and TM is a targeting moiety). Alternatively, linkers ($X_2$) could be polycationic moieties that form non-covalent ionic complex with the siNA drug.

Additional multiarm approaches are envisioned, an example of which is provided below.

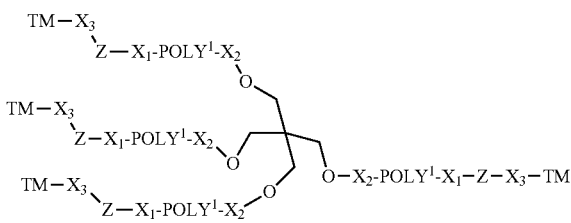

wherein:
each $X_1$ is a releaseable spacer moiety;
each $X_2$ is a stable spacer moiety;
$X_3$ is an optionally stable or releasable spacer moiety (e.g., ester, releasable carbamate, releasable disulfide, and releasable thioether);
Z is a residue of a pharmacologically active agent (e.g., a siRNA);
each $POLY^1$ is a water soluble polymer (e.g., a PEG);
each TM is a targeting moiety, which is an optional presence on one or more polymer-linked pharmacologically active agent moieties (e.g., folate, pemeterxed, RGD peptide and cholesterol).

More structures may also be useful for targeted conjugate delivery of siNA. The targeting moieties may optionally be present on one or more of the polymer linked drug moieties and be linked via a stable or releasable linker (when the targeting moiety is stably linked to siNA, conjugation to the passenger or sense strand would be preferred).

$$Y\text{-}POLY^1\text{-}X_1\text{-}Z\text{—}X_3\text{-}TM$$

wherein:
$X_1$ is a releaseable spacer moiety;
Y is an end-capping group or spacer moiety containing lower alkyl, alkyl or a lipid and optionally connected to a stable or releasable linked targeting moiety (e.g., folate or pemeterxed);
$X_3$ is an optional stable or releasable spacer moiety (e.g., ester, disulfide, releasable carbamate, releasable thioether, cleavable amide and peptide);
Z is a residue of a pharmacologically active agent (e.g., siRNA)
$POLY^1$ is a water soluble polymer (e.g., a PEG); and
each TM is a targeting moiety (e.g., folate, pemeterxed, RGD peptide, and cholesterol), which is an optional presence on one or more polymer-linked pharmacologically active agent moieties.

Note that linear and branched PEG architectures may also be used in this context as shown above.

In the above-described structures, please note that the drug moiety (Z) may also contain various structural motifs especially for siNA delivery (e.g., Z is a targeting moiety-Xn-Z- or Z-Xn-Targeting moiety-; where Xn may be stable or releasable linker). Alternatively linkers ($X_1$) could be polycationic moieties that form non-covalent ionic complex with the siNA drug.

With respect to polymeric reagents, those described here and elsewhere can be purchased from commercial sources (e.g., Nektar Therapeutics, Huntsville, Ala. and NOF Corporation, Japan). In addition, methods for preparing the polymeric reagents are described in the literature.

The attachment between the siNA and the non-peptidic, water-soluble polymer can be direct, wherein no intervening atoms are located between the siNA and the polymer, or indirect, wherein one or more atoms are located between the siNA and the polymer. With respect to the indirect attachment, a "spacer moiety" or "linker" serves as a linker between the residue of the siNA and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of "—" (a covalent bond), —O—, —S—, —S—S—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$-, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms.

Also, the oligomer chain would not be considered part of the spacer moiety if the oligomer is adjacent to a polymer segment and merely represent an extension of the polymer segment.

Compositions

The conjugates are typically part of a composition. Generally, the composition comprises a plurality of conjugates, preferably although not necessarily, each conjugate is comprised of the same siNA (i.e., within the entire composition, only one type of siNA is found). In addition, the composition can comprise a plurality of conjugates wherein any given conjugate is comprised of a moiety selected from the group consisting of two or more different siNA moieties (i.e., within the entire composition, two or more different siNA moieties are found). Optimally, however, substantially all conjugates in the composition (e.g., 85% or more of the plurality of conjugates in the composition) are each comprised of the same siNA.

The composition can comprise a single conjugate species (e.g., a monoPEGylated conjugate wherein the single polymer is attached at the same location for substantially all conjugates in the composition) or a mixture of conjugate species (e.g., a mixture of monoPEGylated conjugates where attachment of the polymer occurs at different sites and/or a mixture monPEGylated, diPEGylated and triPEGylated conjugates). The compositions can also comprise other conjugates having four, five, six, seven, eight or more polymers attached to any given moiety having siNA activity. In addition, the invention includes instances wherein the composition comprises a plurality of conjugates, each conjugate comprising one water-soluble polymer covalently attached to one siNA, as well as compositions comprising two, three, four, five, six, seven, eight, or more water-soluble polymers covalently attached to one siNA.

With respect to the conjugates in the composition, the composition will satisfy one or more of the following characteristics: at least about 85% of the conjugates in the composition will have from one to four polymers attached to the siNA; at least about 85% of the conjugates in the composition will have from one to four polymers attached to the siNA; at least about 85% of the conjugates in the composition will have from one to three polymers attached to the siNA; at least about 85% of the conjugates in the composition will have from one to two polymers attached to the siNA; at least about 85% of the conjugates in the composition will have one polymer attached to the siNA; at least about 95% of the conjugates in the composition will have from one to five polymers attached to the siNA; at least about 95% of the conjugates in the composition will have from one to four polymers attached to the siNA; at least about 95% of the conjugates in the composition will have from one to three polymers attached to the siNA; at least about 95% of the conjugates in the composition will have from one to two polymers attached to the siNA; at least about 95% of the conjugates in the composition will have one polymer attached to the siNA; at least about 99% of the conjugates in the composition will have from one to five polymers attached to the siNA; at least about 99% of the conjugates in the composition will have from one to four polymers attached to the siNA; at least about 99% of the conjugates in the composition will have from one to three polymers attached to the siNA; at least about 99% of the conjugates in the composition will have from one to two polymers attached to the siNA; and at least about 99% of the conjugates in the composition will have one polymer attached to the siNA.

In one or more embodiments, it is preferred that the conjugate-containing composition is free or substantially free of albumin. It is also preferred that the composition is free or substantially free of macromolecules that do not have siNA activity. Thus, it is preferred that the composition is 85%, more preferably 95%, and most preferably 99% free of albumin. Additionally, it is preferred that the composition is 85%, more preferably 95%, and most preferably 99% free of any protein that does not have siNA activity. To the extent that albumin is present in the composition, exemplary compositions of the invention are substantially free of conjugates comprising a poly(ethylene glycol)polymer linking a residue of a siNA to albumin.

Control of the desired number of polymers for any given moiety can be achieved by selecting the proper polymeric reagent, the ratio of polymeric reagent to the siNA, temperature, pH conditions, and other aspects of the conjugation reaction. In addition, reduction or elimination of the undesired conjugates (e.g., those conjugates having four or more attached polymers) can be achieved through purification means.

For example, the polymer-siNA conjugates can be purified to obtain/isolate different conjugated species. Specifically, the product mixture can be purified to obtain an average of anywhere from one, two, three, four, five or more PEGs per siNA, typically one, two or three PEGs per siNA. The strategy for purification of the final conjugate reaction mixture will depend upon a number of factors, including, for example, the molecular weight of the polymeric reagent employed, the particular siNA, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-siNA ratios (e.g., 1-mer, 2-mer, 3-mer, and so forth, wherein "1-mer" indicates 1 polymer to siNA, "2-mer" indicates two polymers to siNA, and so on) on the basis of their differing molecular weights (where the difference corresponds essentially to the average molecular weight of the water-soluble polymer portion). For example, in an exemplary reaction where a 2,000 Dalton oligopeptide is randomly conjugated to a polymeric reagent having a molecular weight of about 20,000 Daltons, the resulting reaction mixture may contain unmodified oligopeptide (having a molecular weight of about 2,000 Daltons), monoPEGylated oligopeptide (having a molecular weight of about 22,000 Daltons), diPEGylated oligopeptide (having a molecular weight of about 42,000 Daltons), and so forth.

While this approach can be used to separate PEG and other polymer-siNA conjugates having different molecular weights, this approach is generally ineffective for separating positional isoforms having different polymer attachment sites within the siNA. For example, gel filtration chromatography can be used to separate from each other mixtures of PEG 1-mers, 2-mers, 3-mers, and so forth, although each of the recovered conjugate compositions may contain PEG(s) attached to different reactive groups (e.g., amine residues) within the siNA.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content (Sims et al. (1980) *Anal. Biochem*, 107:60-63), (iv) sodium dodecyl sulfate polyacrylamide gel electrophoresis (SDS PAGE), followed by staining with barium iodide, and (v) high performance liquid chromatography (HPLC).

Separation of positional isoforms is carried out by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (i.e., positional isoforms).

The compositions are preferably substantially free of proteins and other macromolecules that do not have siNA activity. In addition, the compositions preferably are substantially free of all other noncovalently attached water-soluble polymers. In some circumstances, however, the composition can contain a mixture of polymer-siNA conjugates and unconjugated siNA.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In some embodiments of the invention, the compositions comprising the polymer-siNA conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and U.S. Patent Applications Nos. 2005/0281781, and 2008/0044438. In one or more embodiments, the delivery vehicle is not a liposomal in nature (i.e., lacks liposomes).

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

With respect to pulmonary delivery of the conjugates described herein, it is preferred to employ one or more of the approaches described in U.S. Pat. Nos. 6,565,885; 6,946,117; 6,309,623; and 6,433,040; the contents of all of which are hereby incorporated herein by reference in their entirety.

The invention also provides a method for administering a conjugate as provided herein to a patient suffering from a condition that is responsive to treatment with conjugate. The method comprises administering to a patient, generally via injection, a therapeutically effective amount of the conjugate (preferably provided as part of a pharmaceutical composition). As previously described, the conjugates can be administered injected parenterally by intravenous injection. Advantageously, the conjugate can be administered by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the conjugate. Those of ordinary skill in the art appreciate which conditions a specific conjugate can effectively treat. Advantageously, the conjugate can be administered to the patient prior to, simultaneously with, or after administration of another active agent.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, symptoms of organophosphate poisoning lessen and/or are eliminated entirely.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

One advantage of administering certain conjugates described herein is that individual water-soluble polymer portions can be cleaved when a hydrolytically releasable linkage is included between the residue of siNA and water-soluble polymer. Such a result is advantageous when clearance from the body is potentially a problem because of the polymer size. Optimally, cleavage of each water-soluble polymer portion is facilitated through the use of physiologically cleavable and/or enzymatically releasable linkages such as amide, carbamate, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully described in the literature. Reagents and materials are commercially available and/or their syntheses (particularly with respect to polymeric reagents) are described in the literature unless specifically stated to the contrary. See, for example, M. B. Smith and J. March, *March's Advanced Organic Chemistry: Reactions Mechanisms and Structure*, 6th Ed. (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

References in this Experimental to polymeric reagents identified by the following designations shall represent the following structure:

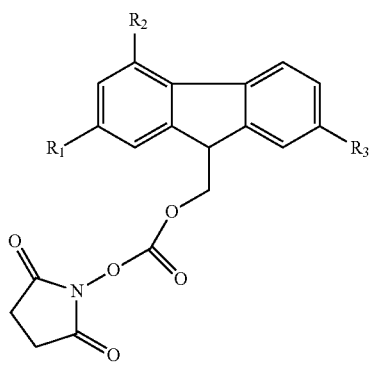

wherein, when the polymeric reagent designated as:

"C2," $R_2$ is H and each of $R_1$ and $R_3$ is

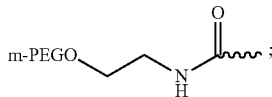

"G2," $R_2$ is H and each of $R_1$ and $R_3$ is

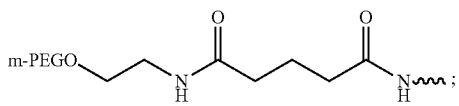

"CG," $R_1$ is H, $R_2$ is

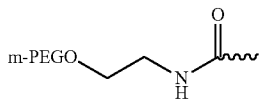

and $R_3$ is

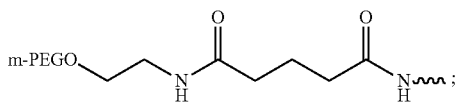

and

"CAC," $R_1$ is H, $R_2$ is

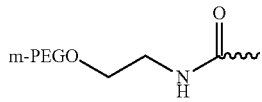

and $R_3$ is

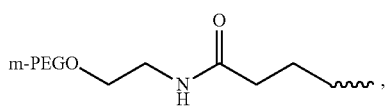

and each m-PEG represents $CH_3O(CH_2CH_2O)_n$—$CH_2CH_2$~ and (n) is defined such that both m-PEG moieties in the structure provide the molecular weight stated in the particular example.

Further, the following structures shall be identified in this Experimental by the designations located adjacent to the structure:

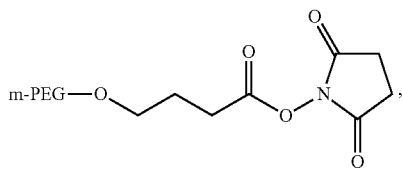

m-PEG—SBA

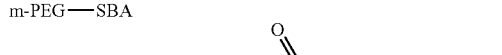, m-PEG—SPA

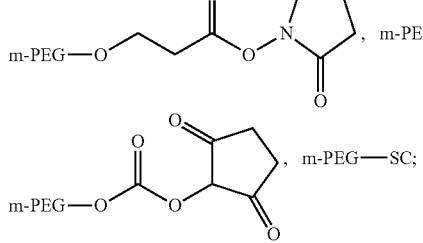, m-PEG—SC;

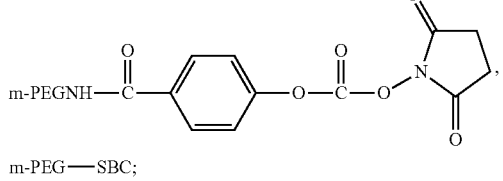

m-PEG—SBC;

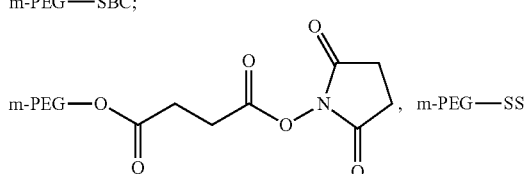, m-PEG—SS

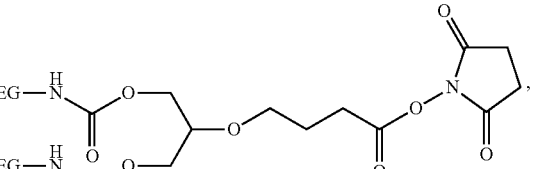

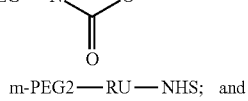; and

-continued

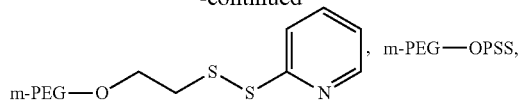

wherein m-PEG represents $CH_3O(CH_2CH_2O)_n$—$CH_2CH_2$~ and (n) is defined such that m-PEG moiety in the structure provides the molecular weight stated in the particular example.

The C2, G2, CG, CAC, SBC and SS polymeric reagents, upon conjugation to the siNA, provide conjugates that are releaseable in vivo (i.e., wherein the polymeric reagent detaches or substantially detaches from the conjugate, thereby releasing the original siNA or an siNA only slightly modified with a small residue from the polymeric reagent), whereas the PEG2-RU-NHS polymeric reagent, upon conjugation to the siNA, provides a substantially stable conjugate. The OPSS polymeric reagent, upon conjugation to the siNA, provides a conjugate that may undergo disulfide exchange. Single- and double-stranded RNA sequences were manufactured by Tri-Link BioTechnologies, San Diego, Calif., Dharmacon RNAi Technologies, Lafayette, Colo., and IDT Inc., Coralville, Iowa. Chitosan was obtained from Kitto Life, Kyongki-Do, Korea. Two forms were used: chitooligosaccharide with average MW about 10,000 Daltons (measured by GPC) and with ~94% deacetylation (measured by NMR) and chitoooligosaccharide average MW 3,000-5,000 Daltons (measured by GPC) and with ~86% deacetylation (by NMR). Generally, it is preferred to use chitosan lacking derivatization with side chains of —NH—$(CH_2)_a$—$(NH(CH_2)_2)_e$—$NH_2$, where (a) and (e) are independently 1 to 5. Generally, it is also preferred to use chitosan with a molecular weight of less than about 100,000 Daltons, more preferably less than about 60,000 Daltons, still more preferably less than 30,000 Daltons, with less than 20,000 Daltons being most preferred.

Further, the following siNAs (single-stranded oligonucleotide sequences are identified with SEQ ID NOs), shall be identified in this Experimental by the SEQ ID NOs located adjacent to the sequence or corresponding oligonucleotide (oligo) number:

Example 1

Conjugation of Double-stranded siRNA with a 5'-aminoC6 Linker with

1a) CAC 20K Polymeric Reagent ["9-hydroxymethyl-4-(mPEG(10,000)-carboxyamide)-7-(3-(mPEG (10,000)carbamoyl-propyl)-fluorene-N-hydroxysuccinimide" or "4,7-CAC-PEG2-FMOC-NHS 20K"] and 1b) GC 20K Polymeric Reagent ["9-hydroxymethyl-4-(mPEG(10,000)-carboxyamide)-7-(3-(mPEG (10,000)amidoglutaric amide)-fluorene-N-hydroxysuccinimide" or "4,7-CG-PEG2-FMOC-NHS 20K"]

Sodium phosphate buffer (25 mM; pH 7.5) was prepared. A stock solution (280 µM) of double-stranded siRNA with a 5'-aminoC6 linker on the sense strand (SEQ ID NO: 183: SEQ ID NO: 192) (IDT Inc., Coralville, Iowa) was prepared in 1×siRNA buffer (diluted from 5×siRNA buffer, pH 7.5, Dharmacon Lafayette, Colo.). The reactions were run by dissolution of the indicated polymeric reagent CAC or GC (4 mg, 0.2 µmol) in a mixture of siRNA stock solution (27 µl, 0.0075 µmol) and the indicated sodium phosphate buffer (25 mM, 173 µl). The reaction mixtures were stirred and incubated at room temperature for three hours. Aliquots (2 µl) were taken, quenched with 0.1 M glycine (2 µl) and diluted with RNAse free water and 6× loading buffer (comprised of 10 mM pH 7.6 Tris buffer, 60 mM EDTA, 60% glycerol, 0.03% bromophenol blue and 0.03% xylene cyanol). The samples were loaded on a non-denaturing PAGE gel (Invitrogen 20% TBE gel) and run at 100 V for 120 min. The gels were removed, stained with ethidium bromide (BioChemika, Sigma) for 30 minutes and then destained for more than one hour.

The gel is provided in FIG. 1, wherein lanes 1 and 2 correspond to siRNA-CAC conjugate, lane 3 corresponds to siRNA, and lanes 4 and 5 correspond to siRNA-CG conjugate.

| Sequence | Name | SEQ ID NO: |
|---|---|---|
| 5' (C6-NH2) AmCAmACmAGmACmUUmUAmAUmGUmAA-3' | Oligo 13 | 183 |
| 5'(C6-NH2) AmCAmACmAGmACmUUmUAmAUmGUmAA-3'(C6-SH)(Cy5.5) | Oligo 14 | 184 |
| 5' (C6-NH2)AmCAmACmAGmACmUUmUAmAUmGUmAA-3'(cholesteryl-TEG) | Oligo 18 | 185 |
| 5'(C6-S-SC6) -AmCAmACmAGmACmUUmUAmAUmGUmAA-3' | Oligo 3 | 186 |
| 5'(C6-NH2)AmCAmACmAGmACmUUmUAmAUmGUmAA-3'(C6-NH) | Oligo 5 | 187 |
| 5'mUUmACmAUmUAmAAmGUmCUmGUmUGmU-3' (C6-NH)(Cy5.5) | Oligo 28 | 188 |
| 5'mUUmACmAUmUAmAAmGUmCUmGUmUGmU-3' C6-NH2) | Oligo 31 | 189 |
| 5'mUUmACmAUmUAmAAmGUmCUmGUmUGmU-3' C3-S-S-C3 | Oligo 34 | 190 |
| 5' AmCAmACmAGmACmUUmUAmAUmGUmAA-3' | Sense | 191 |
| 5'mUUmACmAUmUAmAAmGUmCUmGUmUGmU-3' | Antisense | 192 |
| - Ai2FCAAi2FCAGAi2FCTi2FUTAATGTAAmUmU | Sense | 193 |
| 5'- rUmUrAmCAi2FUmUAmAAmGmUi2FCi2FUmGi2FUmUmGi2FUmUmU | Antisense | 194 |

Example 2

Conjugation of double-stranded siRNA and single-stranded siRNA with 2a) m-PEG-SBA 5K ["mPEG-succinimidyl butanoate 5K"] and 2b) m-PEG-SPA 5K [or "mPEG-succinimidyl propionate 5K"]

Preparation of Conjugates with a Double-Stranded siRNA

Sodium phosphate buffer (100 mM; pH 8.0) was prepared. A stock solution (280 μM) of double-stranded siRNA with a 5'-aminoC6 linker on the sense strand (SEQ ID NO: 183:SEQ ID NO: 192) (IDT Inc., Coralville, Iowa) was prepared in 1×siRNA buffer (diluted from 5×siRNA buffer, pH 7.5, Dharmacon, Lafayette, Colo.). The reactions in were run by dissolution of the indicated polymeric reagent (1 mg, 0.2 μmol) in a mixture of siRNA stock solution (10 μl, 0.0028 μmol) and the indicated sodium phosphate buffer (100 mM, 90 μl). The reaction mixtures were stirred and incubated at room temperature for three hours. Aliquots (2 μl) were taken, quenched with 0.1 M glycine (2 μl) and diluted with RNAse free water and loading buffer.

Preparation of Conjugates with a Single-Stranded siRNA

A stock solution (1000 μM) of siRNA sense-strand with a 5'-aminoC6 linker (SEQ ID NO: 183) (IDT Inc., Coralville, Iowa) was prepared in 1×siRNA buffer. The reactions were run by dissolution of mPEG-SBA 5K reagent (1 mg, 0.2 μmol) in a mixture of siRNA stock solution (10 μl, 0.01 μmol) and the indicated sodium phosphate buffer (100 mM, 90 μl). The reaction mixtures were stirred and incubated at room temperature for three hours. Aliquots (2 μl) were taken, quenched with 0.1 M glycine (2 μl) and diluted with RNAse free water and loading buffer.

The samples were loaded on a non-denaturing PAGE gel (Invitrogen 20% TBE gel) and run at 100 V for 120 minutes. The gels were removed, stained with ethidium bromide (BioChemika, Sigma) for 30 minutes and then destained for more than one hour.

Figure 2:
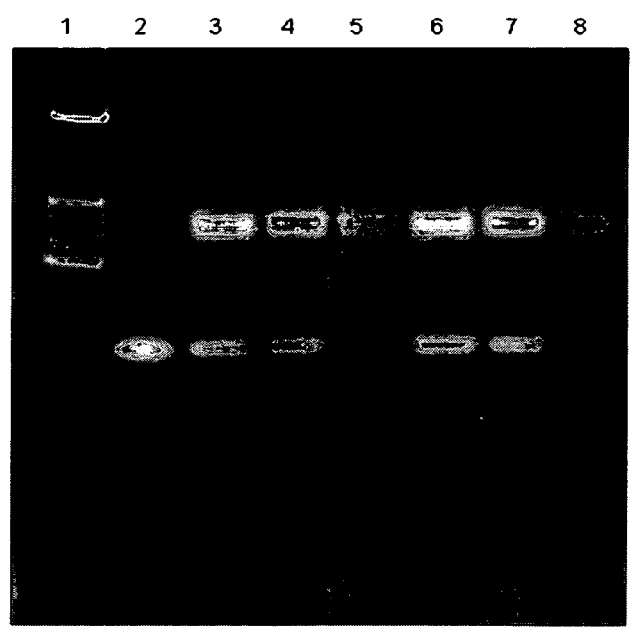
FIG. 2 is a representation of a gel as further described in Example 2.

The gel is provided in FIG. 2, showing native PAGE 5'-aminoC6 double-stranded siRNA (280 μM)+mPEG-SBA 5K or mPEG-SPA 5K (70×) comparisons with 5'-aminoC6 siRNA sense strain (1000 μM)+mPEG-SBA 5K (20×) at pH 8.0 in 100 mM phosphate buffer for three hours. Lane corresponds to a 10 bp DNA ladder, lane 2 corresponds to double-stranded siRNA, lane 3 corresponds to double-stranded siRNA-mPEG-SBA 5K conjugate, lane 4 corresponds to double-stranded siRNA-mPEG-SPA 5K conjugate, lane 5 corresponds to siRNA sense strain-mPEG-SBA 5K conjugate, lane 6 corresponds to double-stranded siRNA-mPEG-SBA 5K conjugate, lane 7 corresponds to double-stranded siRNA-mPEG-SPA 5K conjugate, lane 8 corresponds to siRNA sense strain-mPEG-SBA 5K, conjugate, and 9 corresponds to double-stranded siRNA.

Example 3a-3f

Conjugation of Double-Stranded siRNA (Ds-siRNA) and Single-Stranded siRNA (ss-siRNA) with Polymeric Reagents 3a) and 3b) m-PEG2-RU-NHS 20K ["Reversed-Urethane Branched PEG NHS 20K"], 3c) and 3d) m-PEG-SC 20K ["mPEG Succinimido Carbonate 20K"], and 3e) and 3f) CAC ["9-hydroxymethyl-4-(mPEG(10,000)-carboxyamide)-7-(3-(mPEG(10,000)carbamoyl-propyl)-fluorene-N-hydroxysuccinimide" or "4,7-CAC-PEG2-FMOC-NHS 20K"]

The reaction parameters were set up according to Table 4. The polymeric reagents were dissolved in 2 mM HCl (100 mg/ml) and used immediately. Each portion of PEG reagent was added every 30 minutes. The concentration of 5'-AminoC6 double-stranded (SEQ ID NO: 183:SEQ ID NO: 192) or single stranded siRNA (SEQ ID NO: 183) in the reaction solution was 28 μM. The reaction mixtures were incubated at ambient temperature (22 C) with stirring. At 3 hours, 10 μl reaction mixtures were mixed with 2.5 μl 0.2 M glycine (unbuffered) to quench the reaction. The reaction mixtures were analyzed by 20% non-denaturing PAGE and 4-20% native PAGE gels. See FIG. 3, FIG. 4, FIG. 5A and FIG. 5B.

TABLE 4

Reaction Parameters for Examples 3a-3f

| Example | Polymeric Reagent 100 mg/mL, μl | 500 mM EPPS buffer, pH 8.5, μl | siRNA | RNAse free water (μl) | Total volume (μl) | Ratio |
|---|---|---|---|---|---|---|
| 3a | m-PEG2-RU-NHS 20K, 85%, 20 μl × 4 (340 nmole) | 40 | ds-5' AminoC6, 0.28 mM in siRNA buffer, 20 μl (5.6 nmole) | 60 | 200 | 60:1 |
| 3b | m-PEG2-RU-NHS 20K, 85%, 20 μl × 4 (336 nmole) | 40 | ss-5' AminoC6, 1.0 mM in siRNA buffer, 5.6 μl (5.6 nmole) | 74.4 | 200 | 60:1 |
| 3c | mPEG-SC 20K, 85%, 20 μl × 4 (340 nmole) | 40 | ds-5' AminoC6, 0.28 mM in siRNA buffer, 20 μl (5.6 nmole) | 60 | 200 | 60:1 |
| 3d | mPEG-SC 20K, 85%, 20 μl × 4 (340 nmole) | 40 | ss-5' AminoC6, 1.0 mM in siRNA buffer, 5.6 μl (5.6 nmole) | 74.4 | 200 | 60:1 |
| 3e | 4,7-CAC-mPEG-FMOC-NHS, 87%, 20 μl × 4 (340 nmole) | 40 | ds-5' AminoC6, 0.28 mM in siRNA buffer, 20 μl (5.6 nmole) | 60 | 200 | 60:1 |

TABLE 4-continued

Reaction Parameters for Examples 3a-3f

| Example | Polymeric Reagent 100 mg/mL, μl | 500 mM EPPS buffer, pH 8.5, μl | siRNA | RNAse free water (μl) | Total volume (μl) | Ratio |
|---|---|---|---|---|---|---|
| 3f | 4,7-CAC-PEG2-FMOC-NHS, 87% 20 μl × 4 (340 nmole) | 40 | ss-5' AminoC6, 1.0 mM in siRNA buffer, 5.6 μl (5.6 nmole) | 74.4 | 200 | 60:1 |

Figure 3:
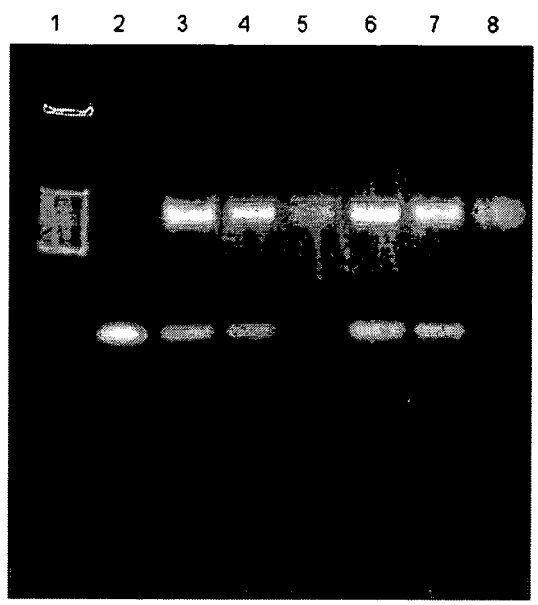
FIG. 3, FIG. 4, FIG. 5A and FIG. 5B are representations of gel as further described in Examples 3a-3f.
Figure 4:

A gel is provided in FIG. 3, showing native 20% PAGE 5'-aminoC6 ds-siRNA+indicated polymeric reagent (60×) comparisons with 5'-aminoC6 ss-siRNA at pH 8.5 in 100 mM EPPS buffer for three hours. Lane 1 corresponds to a 10 bp DNA ladder, lane 2 corresponds to ds-siRNA-m-PEG2-RU-NHS 20K conjugate, lane 3 corresponds to ss-siRNA-m-PEG2-RU-NHS conjugate, lane 4 corresponds to ds-siRNA-m-PEG-SC 20K conjugate, lane 5 corresponds to ss-siRNA-m-PEG-SC 20K conjugate, lane 6 corresponds to ds-siRNA-CAC 20K conjugate, lane 7 corresponds to ss-siRNA-4,7-CAC 20K conjugate (although the bands crossed over to lane 6). The conversion yields of ds-siRNA conjugation were estimated with density scanning: all were roughly 50%. FIG. 4 represents the gel of FIG. 3 stained with iodine, thereby showing the PEG components.

Figure 5A:
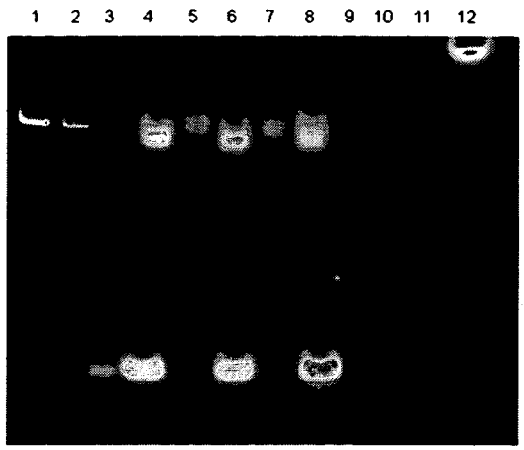
Figure 5B:
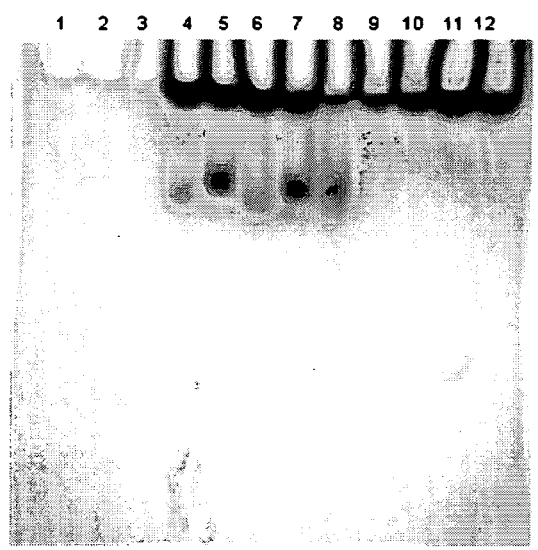

A gel is provided in FIG. 5A, showing igure native 4-20% gradient PAGE 5'-aminoC6 double-stranded siRNA+indicated polymeric reagent comparisons with 5'-aminoC6 siRNA sense strain at pH 8.5 in 100 mM EPPS buffer for three hours. Lanes 1 and 2 correspond to a 10 bp DNA ladder, lane 3 corresponds to ds-siRNA, lane 4 corresponds to ds-siRNA-m-PEG2-RU-NHS 20K conjugate, lane 5 corresponds to ss-siRNA-m-PEG2-RU-NHS 20K conjugate, lane 6 corresponds to ds-siRNA-m-PEG-SC 20K conjugate, lane 7 corresponds to ss-siRNA-m-PEG-SC 20K conjugate, lane 8 corresponds to ds-siRNA-4,7-CAC 20K conjugate, lane 9 corresponds to ss-siRNA-4,7-CAC 20K conjugate (although the bands crossed over to lane 6), lane 10 corresponds to mPEG2-RU-NHS 20K, lane 11 corresponds to mPEG-SC 20K, lane 12 corresponds to CAC 20K. Conversion yields of ds-siRNA conjugation were estimated by density scanning: all were roughly 50%. FIG. 5B represents the gel of FIG. 5A stained with iodine, thereby showing the PEG components.

Figure 6A:
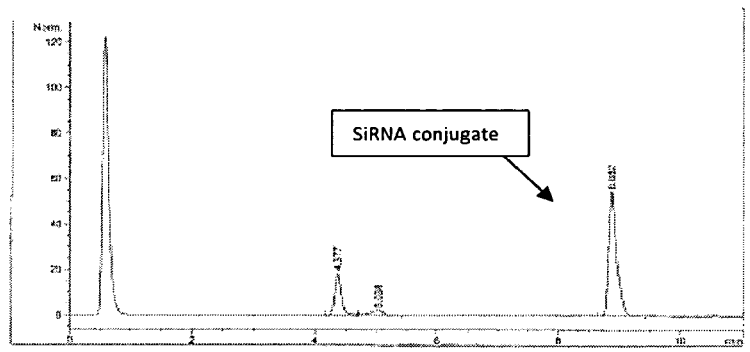
FIG. 6A, FIG. 6B and FIG. 6C are representations of chromatograms as further described in Examples 3a-3f
Figure 6B:
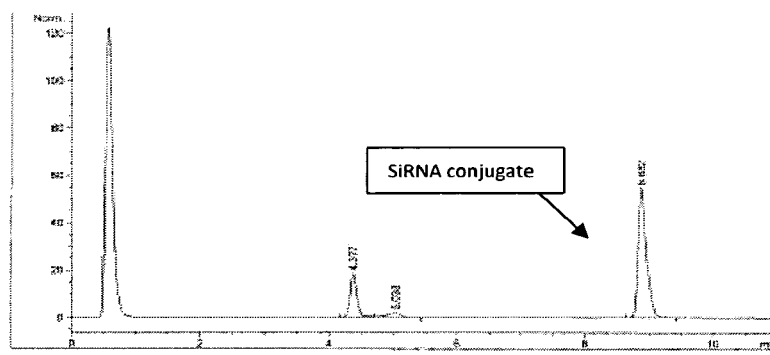
Figure 6C:
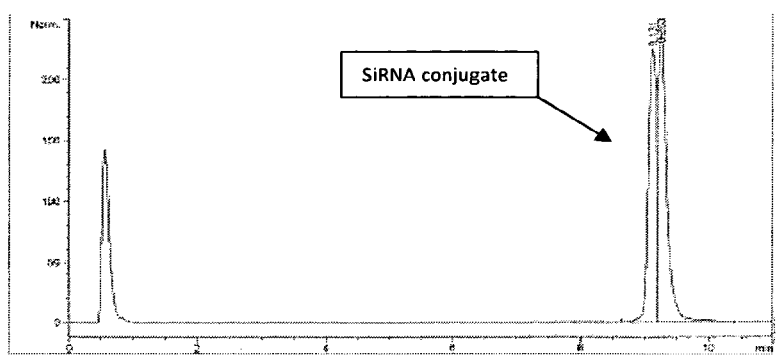

Single stranded siRNA conjugation mixtures were analyzed by RP-HPLC (reversed phase-high performance liquid chromatography), results shown in FIG. 6A, FIG. 6B and FIG. 6C, wherein the chromatogram provided in FIG. 6A corresponds to the product resulting from the reaction parameters for Example 3b, 74% conversion, FIG. 6B corresponds to the product resulting from the reaction parameters for Example 3d, 63.8% conversion, and FIG. 6C corresponds to the product resulting from the reaction parameters for Example 3f, complete conversion detected.

Example 4

Conjugation of 5'AminoC6 Tetramer with m-PEG2-RU-NHS 20K

"Reversed-Urethane Branched PEG NHS 20K"

Figure 7:
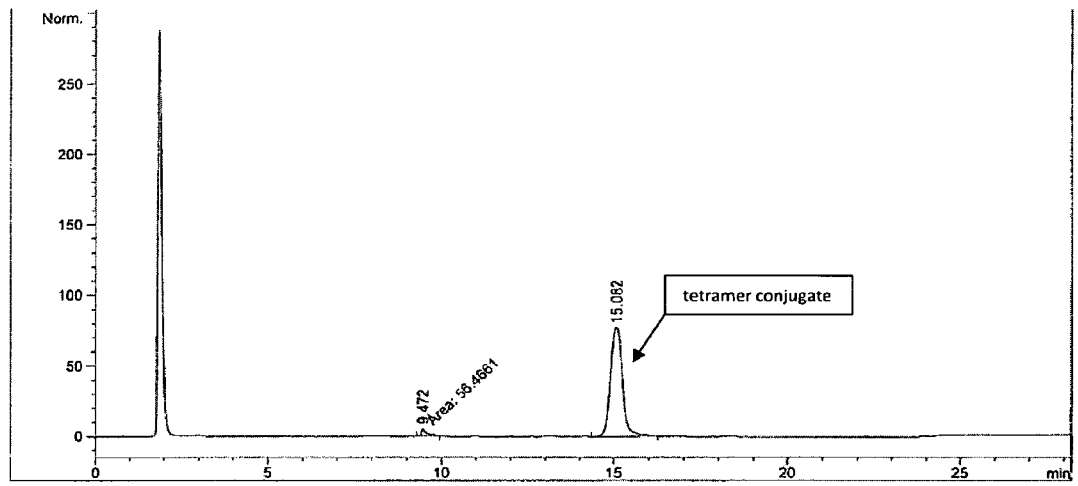
FIG. 7 is a representation of a chromatogram as further described in Example 4.

EPPS buffer (500 mM) was prepared at pH 8.5. A stock solution (14.723 mM) of 5'-aminoC6 ACAA tetramer (Trilink Biotechnology, San Diego, Calif.) was prepared in 1×siRNA buffer (diluted from 5×siRNA buffer, pH 7.5, Dharmacon, Lafayette, Colo.). The reaction was run by dissolution of the indicated polymeric reagent (36.8 mg, 85%) in a mixture of siRNA stock solution (10 μl) and the indicated EPPS buffer (500 mM, 490 μl). The reaction mixture was stirred and incubated at room temperature for three hours. Aliquot (2 μl) was taken, quenched with 0.1 M glycine (2 μl) and diluted with RNAse free water. The sample was analyzed on RP-HPLC, wherein the chromatogram provided in FIG. 7 corresponds to this example and shows a conversion yield of 97%.

Examples 5a and 5b

Conjugation of ss-siRNA with m-PEG-SC 20K ["mPEG Succinimido Carbonate 20K"]

Figure 8:
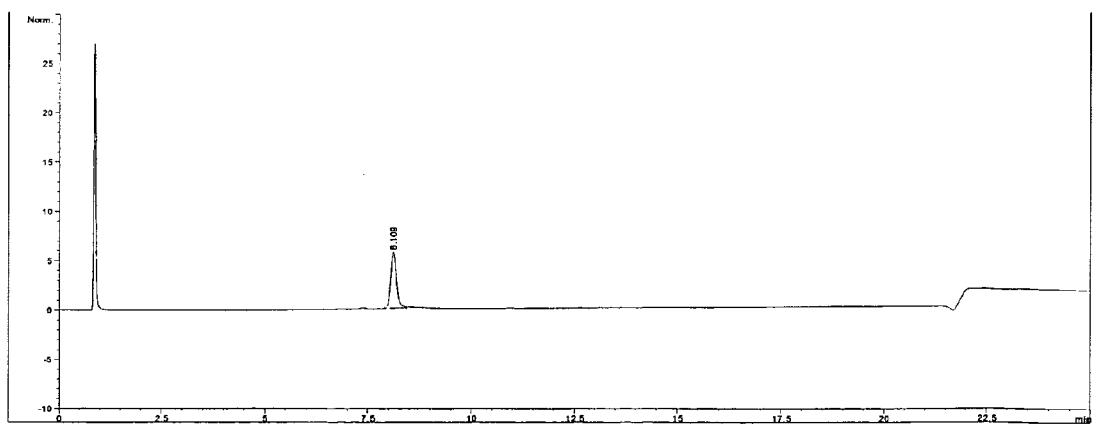
FIG. 8 is a representation of a chromatogram as further described in Examples 5a and 5b and FIG. 9 is a representation of mass spectrometry results as further described in Examples 5a and 5b.
Figure 9:
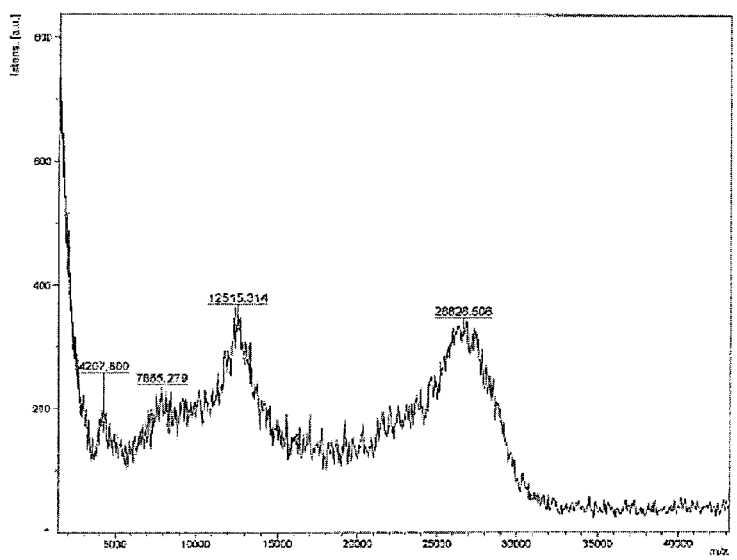

The mPEG reagent was dissolved in 2 mM HCl (100 mg/ml) and used immediately. A stock solution (10.0 mM) of 5'-AminoC6 siRNA sense strain (SEQ ID NO: 183) (Trilink Biotechnology, San Diego, Calif.) was prepared. The reaction was conducted using the reaction parameters set forth in Table 5. The reaction mixtures were incubated at ambient temperature (22° C.). At 15, 30, 60, 90 minutes, 2 μl reaction mixtures were mixed with 2 μl 0.2 M glycine (unbuffered) to quench the reaction. The samples were analyzed via RP-HPLC (results provided in Table 6). The reaction mixture was subjected to purification on FPLC system equipped with Hi-Trap Q HP anion-exchange cartridge. Pure conjugate was obtained, as shown in the chromatogram provided in FIG. 8 while FIG. 9 provides mass spectrometry results (MALDI-MS) of the m-PEG-SC-(ss-siRNA) conjugate.

TABLE 5

Reaction Parameters for Example 5a and Example 5b

| | Example 5a | Example 5b |
|---|---|---|
| m-PEG-SC 20K (90%, 100 mg/ml), μl | 14.12 | 28.24 |
| ss-siRNA (96%, 10 mM), μl | 1 | 1 |
| EPPS buffer (1M, pH 8.5), μl | 3.33 | 3.33 |
| RNAse free water, μl | 14.88 | 0.76 |
| Total Volume, μl | 33.33 | 33.33 |
| Ratio | 6:1 | 12:1 |

TABLE 6

Results at Time Points 15, 30, 60 and 90 minutes for
Example 5a and Example 5b

| Time Point (minutes) | Conversion Yield, % | |
|---|---|---|
| | Example 5a 6:1 | Example 5b 12:1 |
| 15 | 49.0 | 67 |
| 30 | 59.3 | 76.8 |
| 60 | 64.0 | 85.4 |
| 90 | 63.3 | 88.0 |

Example 6

Conjugation of ss-siRNA with CAC 20K Polymeric Reagent

"4,7-CAC-PEG2-FMOC-NHS 20K"

Figure 10:
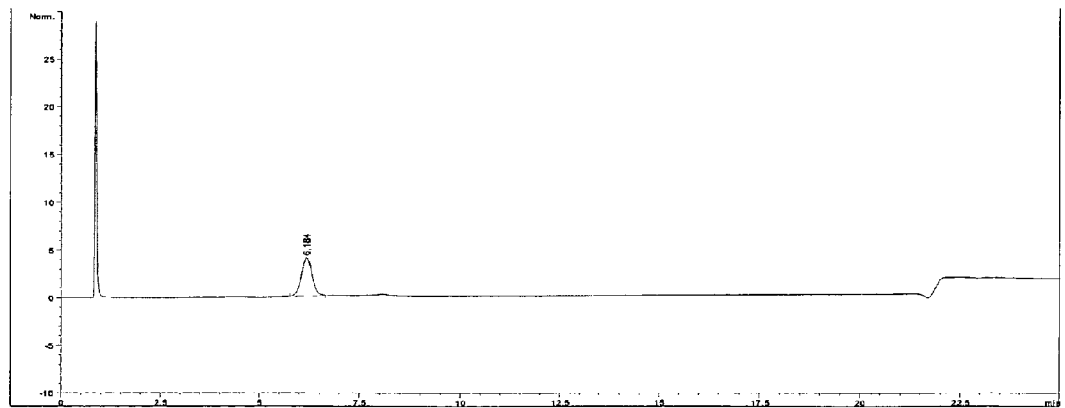
FIG. 10 is a representation of a chromatogram as further described in Example 6.
Figure 11:
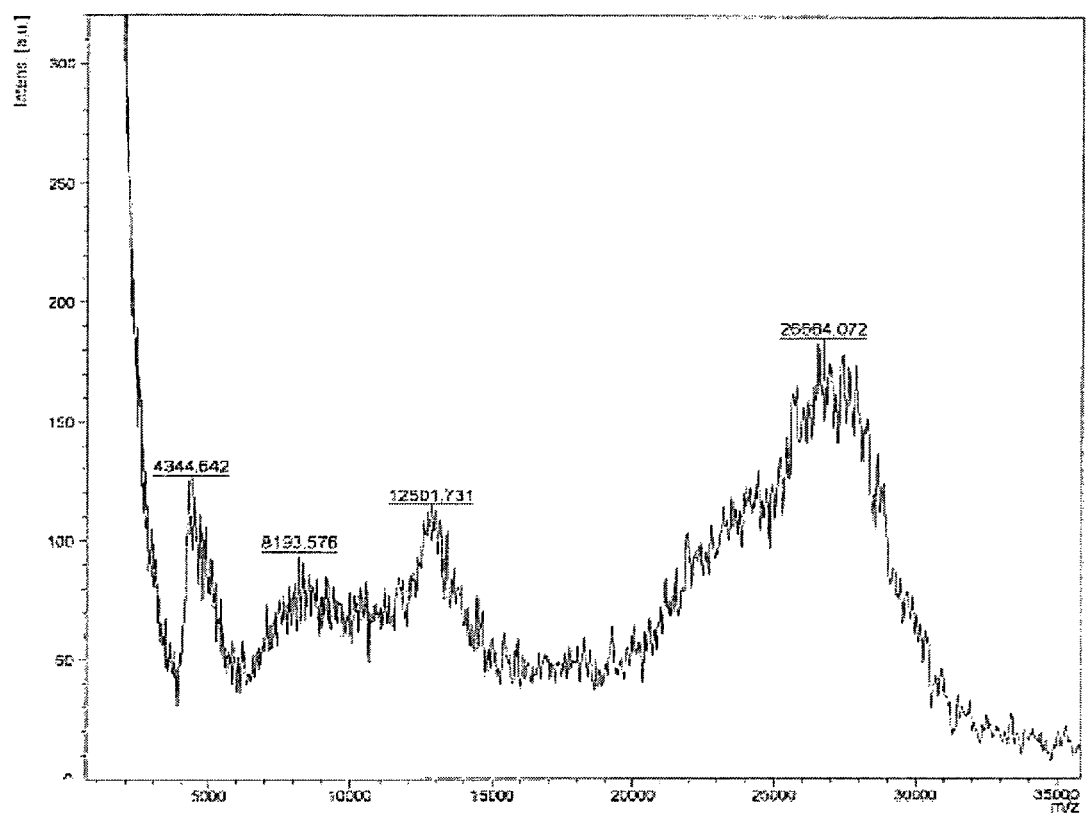
FIG. 11 is a representation of mass spectrometry results as further described in Example 6.

The reaction was conducted in a manner similar to those of the previous examples, using the reaction parameters set forth in Table 7. The reaction mixtures were incubated at ambient temperature (22° C.). At 15, 30, 60, 90, and 180 minutes, 2 μl reaction mixtures were mixed with 2 μl 0.2 M glycine (unbuffered) to quench the reaction. The samples were analyzed on RP-HPLC (results provided in Table 8). The reaction mixture was subjected to purification on FPLC system equipped with Hi-Trap Q HP anion-exchange cartridge. The pure product was obtained. The RP-HPLC chromatogram of the product is provided in FIG. 10 while FIG. 11 provides mass spectrometry results (MALDI-MS) of the CAC-(ss-siRNA) conjugate.

TABLE 7

Reaction Parameters for Example 6a and Example 6b

| | Example 6a | Example 6b |
|---|---|---|
| CAC 20K (90%, 100 mg/ml), μl | 14.12 | 28.24 |
| ss-siRNA (96%, 10 mM), μl | 1 | 1 |
| EPPS buffer (1M, pH 8.5), μl | 3.33 | 3.33 |
| RNAse free water, μl | 14.88 | 0.76 |
| Total Volume, μl | 33.33 | 33.33 |
| Ratio | 6:1 | 12:1 |

TABLE 8

Results at Time Points 15, 30, 60, 90 and 180 minutes for
Example 6a and Example 6b

| Time Point (minutes) | Conversion Yield, % | |
|---|---|---|
| | Example 6a 6:1 | Example 6b 12:1 |
| 15 | 37.8 | 54.0 |
| 30 | 50.3 | 69.1 |
| 60 | 55.0 | 77.8 |
| 90 | 56.3 | 80.4 |
| 180 | 56.4 | 79.6 |

Figure 12:
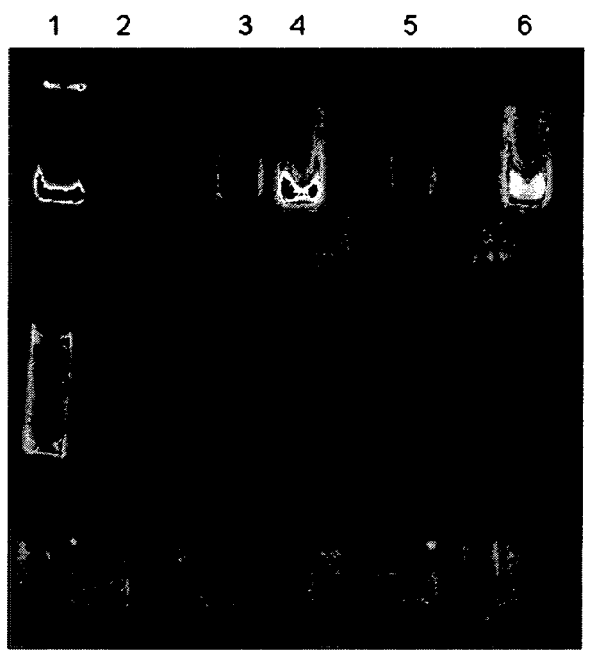
FIG. 12 is a representation of a gel as further described in Example 6.

Further analysis via a native gel analysis for the reaction conducted for 180 minutes were performed by mixing 0.5 μl of the reaction mixture with 1 μl 0.2 M glycine (unbuffered) to quench the reaction. The reaction mixtures were analyzed by 4-20% native PAGE gel as shown in FIG. 12. In FIG. 12, lane 1 corresponds to a 10 bp DNA ladder, lane 2 corresponds to ss-siRNA, lane 3 corresponds to m-PEG-SC 20K-ss-siRNA conjugate (6:1), lane 4 corresponds to m-PEG-SC 20K-ss-siRNA conjugate (12:1), lane 5 corresponds to CAC 20K-ss-siRNA (6:1) conjugate, lane 6 corresponds to CAC 20K-ss-siRNA conjugate (12:1).

Example 7

PEGylation and Purification of CAC 20K-ssRNA Conjugate

"CAC-PEG2-FMOC-20K-ssRNA Conjugate"

Figure 13:
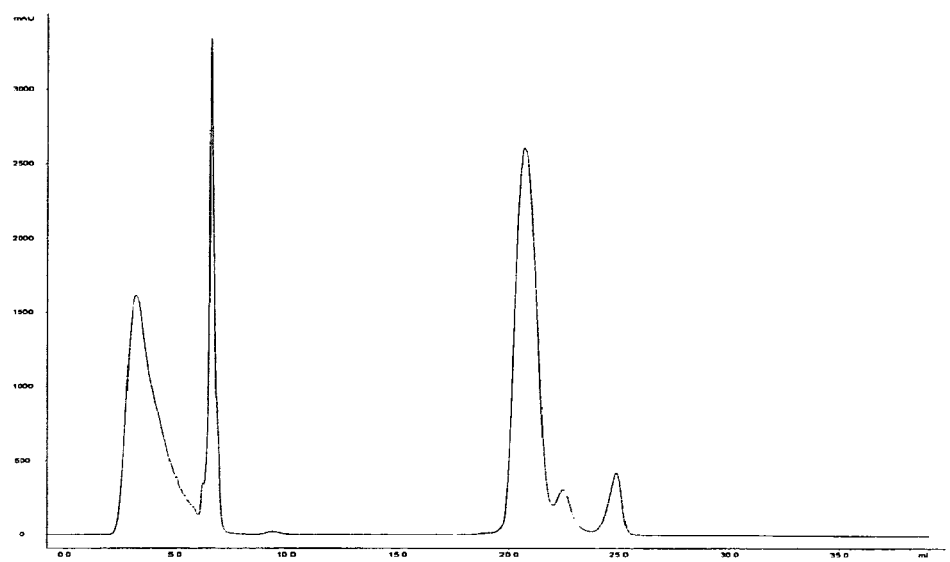
FIG. 13 is a representation of a chromatogram as further described in Example 7.

CAC-ssRNA conjugate was produced in a 0.3-mL reaction mixture consisting of 0.030 mL 1 M EPPS buffer, pH 8.5, 0.009-ML 10 mM ssRNA (sequence: 5'-C6-$NH_2$-AmCAmACmAGmACmUUmUAmAUmGUmAA-3', SEQ ID NO: 183) and 0.261 ml of 100 mg/mL CAC 20K polymeric reagent. The CAC 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris buffer, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volumes). The linear gradient consisted of 10 to 80% of the buffer B over the twenty column volumes at the elution flow rate of 1 mL/min. The chromatogram of the reaction mixture is provided in FIG. 13. The concentration of the conjugate was determined by UV spectrophotometry. The purity of the conjugate was confirmed by ion-exchange HPLC. MALDI-TOF analysis was performed to confirm the molecular weight of the conjugate.

Example 8

PEGylation and Purification of CG 20K-ssRNA Conjugate

"CG-PEG2-FMOC-20K-ssRNA Conjugate"

Figure 14:
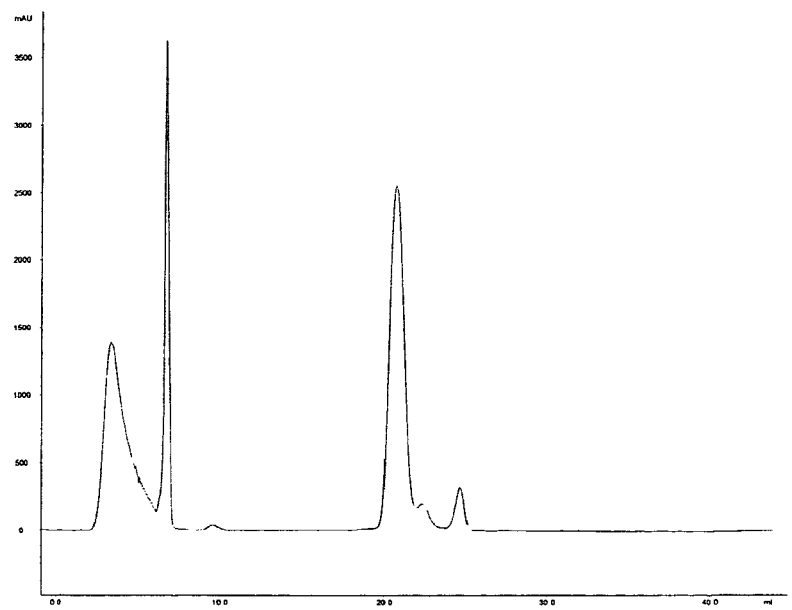
FIG. 14 is a representation of a chromatogram as further described in Example 8.

CG 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-$NH_2$-AmCAmACmAGmACmUUmUAmAUmGUmAA-3', SEQ ID NO: 183) and 0.261 ml of 100 mg/mL CG 20K polymeric reagent. The CG 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-ML with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with the buffer A (5 column volumes). The linear gradient consisted of 10 to 80% of the buffer B over the twenty column volumes at the elution flow rate of 1 mL/min. The chromatogram of the reaction mixture is provided in FIG. 14. The concentration of the conjugate was determined by UV spectrophotometry. The purity of the conjugate was determined by ion-exchange HPLC. MALDI-TOF analysis was performed to confirm the molecular weight of the conjugate.

Example 9

PEGylation and Purification of C2 20K-ssRNA Conjugate

"C2-PEG2-FMOC 20K-ssRNA Conjugate"

Figure 15:
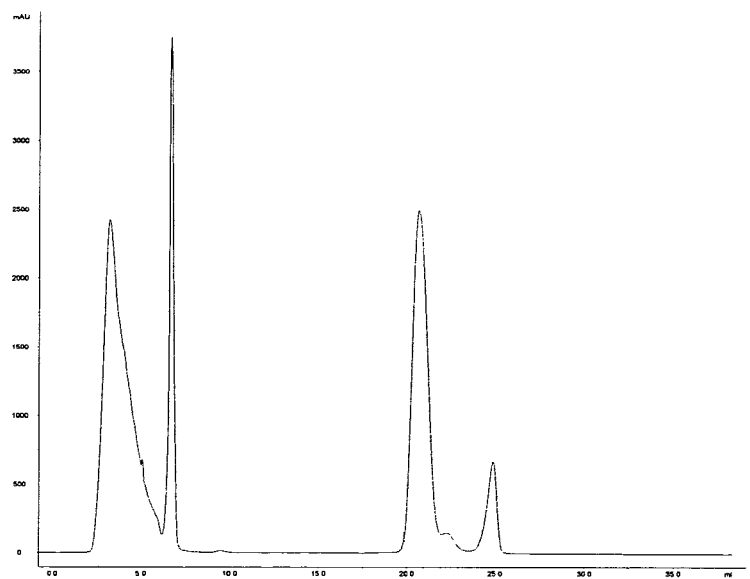
FIG. 15 is a representation of a chromatogram as further described in Example 9.

C2 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$-AmCAmACmAGmACmUUmUAmAUmGUmAA-3', SEQ ID NO: 183) and 0.261 ml of 100 mg/mL C2 20K polymeric reagent. The C2 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with a 5 column volume of the buffer A. The linear gradient consisted of 10 to 80% of the buffer B over the twenty column volumes at the elution flow rate of 1 mL/min. The chromatogram of the reaction mixture is provided in FIG. 15. The concentration of the conjugate was determined by UV spectrophotometry. The purity of the conjugate was confirmed by ion-exchange HPLC. MALDI-TOF analysis was performed to confirm the molecular weight of the conjugate.

Example 10

Figure 16:
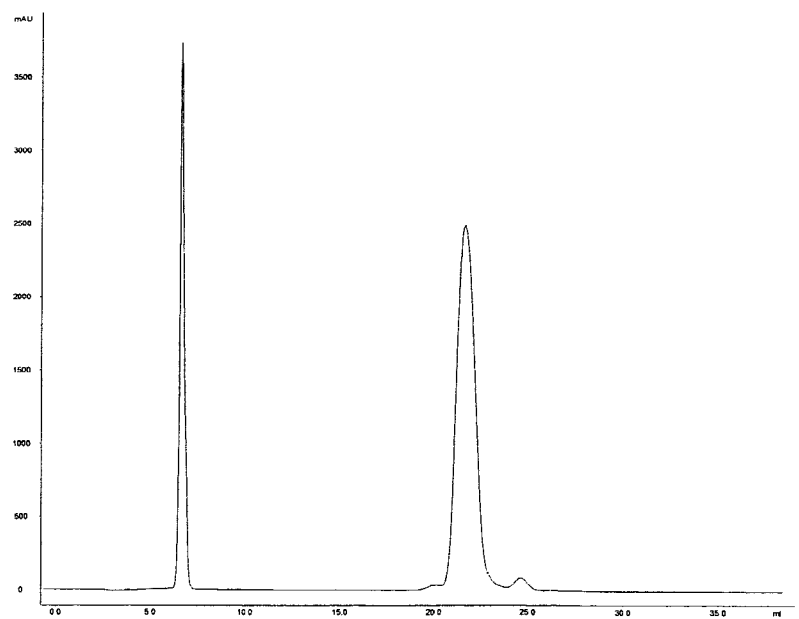
FIG. 16 is a representation of a chromatogram as further described in Example 10.

PEGylation and Purification of m-PEG-SS 20K-ssRNA Conjugate m-PEG-SS 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$-AmCAmACmAGmACmUUmUAmAUmGUmAA-3', SEQ ID NO: 183) and 0.261 ml of 100 mg/mL m-PEG-SS 20K polymeric reagent. The m-PEG-SS 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volumes). The linear gradient consisted of 10 to 80% of the buffer B over the twenty column volumes of the eluate at an elution flow rate of 1 mL/min. The chromatogram of the reaction mixture is provided in FIG. 16. The concentration of the conjugate was determined by UV spectrophotometry. The purity of the conjugate was confirmed by ion-exchange HPLC. MALDI-TOF analysis was performed to confirm the molecular weight of the conjugate.

Example 11

Figure 17:
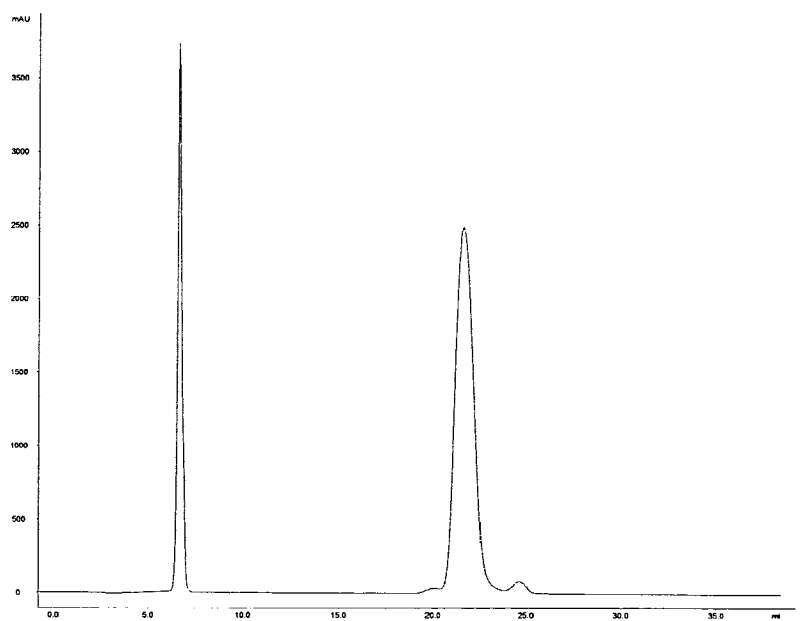
FIG. 17 is a representation of a chromatogram as further described in Example 11.

PEGylation and Purification of m-PEG-SBC 30K-ssRNA Conjugate m-PEG-SBC 30K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$-AmCAmACmAGmACmUUmUAmAUmGUmAA-3', SEQ ID NO: 183) and 0.261 ml RNAse free water. The m-PEG-SBC 30K polymeric reagent (31.5 mg) was added into the RNA with three portions within 20 minutes. After the last addition of the m-PEG-SBC 30K reagent, the reaction mixture was further incubated at 25° C. for 20 minutes; then 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volume). The linear gradient consisted of 10 to 80% of the buffer B over the twenty column volumes of the eluate at an elution flow rate of 1 mL/min. The chromatogram of the reaction mixture is provided in FIG. 17. The concentration of the conjugate as determined by UV spectrophotometry. The purity of the conjugate was confirmed by ion-exchange HPLC. MALDI-TOF analysis was performed to confirm the molecular weight of the conjugate Example 12

Figure 18:
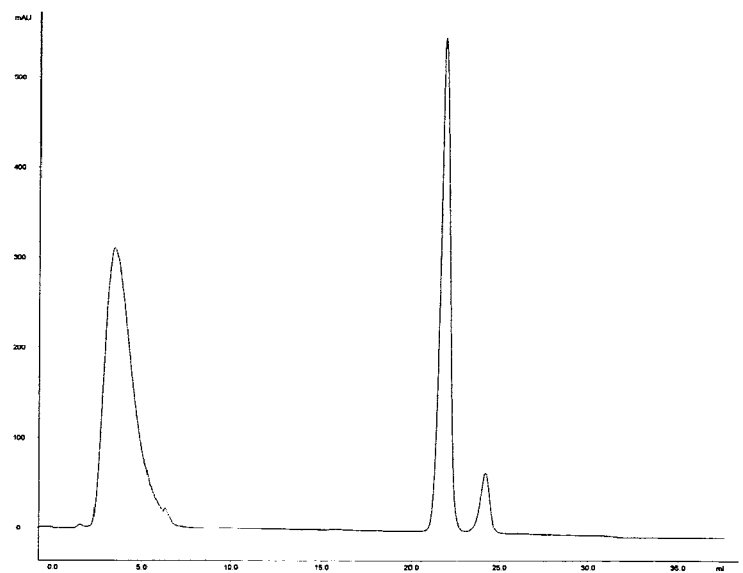
FIG. 18 is a representation of a chromatogram as further described in Example 12.

PEGylation and Purification of m-PEG-OPSS 5K-ssRNA Conjugate m-PEG-OPSS 5K-ssRNA conjugate was produced by the reduction of 5' capped-RNA (5'-C6-S—SC6-AmCAmAC-mAGmACmUUmUAmAUmGUmAA-3', SEQ ID NO: 186) with Tris(2-Carboxyethyl)phosphine hydrochloride (TCEP.HCl) followed by PEGylation with m-PEG-OPSS 5K. To reduce 5'-capped-RNA, a 0.03 mL solution containing 0.002 mL of 5' capped-RNA, 0.006 mL, 1 M, EPPS buffer, pH 8.5 and 0.022-mL 18 mM TCEP.HCl was incubated at 25° C. without stirring for 60 minutes. After 60 minutes incubation, 0.03 mL reaction mixture was loaded on a desalting column (pre-equilibrated with 20 mM HEPES, 50 mM NaCl, pH 7.4) and rinsed with 0.03 mL buffer (20 mM HEPES, 50 mM NaCl, pH 7.4). A total of 0.06 mL solution containing RNA with free thiol group (5'-HSC6-AmCAmACmAGmACmUUmUAmAUmGUmAA-3'(SEQ ID NO: 195)) was collected. To PEGylate free thiol-ss-RNA, 7.2 mg m-PEG-OPSS 5K was added into the 0.06-ML solution containing RNA with free thiol group. After incubation at 25° C. without stirring for three hours, the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 18. The concentration of the conjugate was determined by UV spectrophotometry. The purity of the conjugate was confirmed by ion-exchange HPLC. MALDI-TOF analysis was performed to confirm the molecular weight of the conjugate.

Example 13

PEGylation and Purification of Di-C2 20K-ssRNA Conjugate or "Di-C2-mPEG2-FMOC-20K-ssRNA Conjugate"

Figure 19:
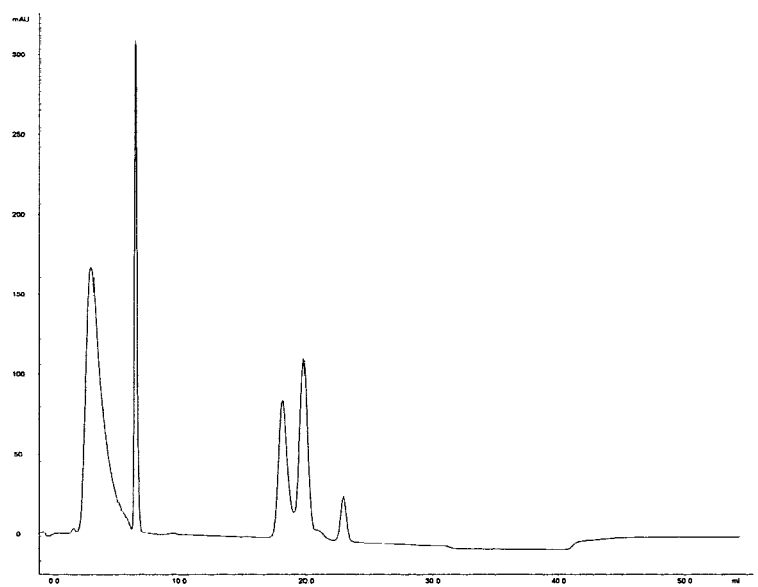
FIG. 19 is a representation of a chromatogram as further described in Example 13.

Di-C2 20K-ssRNA conjugate was produced in a 0.033 mL reaction mixture consisting of 0.003 mL 1 M EPPS buffer, pH 8.5, 0.001 mL 10 mM ssRNA (sequence: 5'-C6-NH$_2$-AmCAmACmAGmACmUUmUAmAUmGUmAA-3', SEQ ID NO: 183) and 0.0281 ml of 100 mg/mL C2 20K polymeric reagent. The C2 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.005 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 19. The concentration of the conjugate was determined by UV spectrophotometry. The purity of the conjugate was confirmed by ion-exchange HPLC. MALDI-TOF analysis was performed to confirm the molecular weight of the conjugate.

Example 14

Figure 20:
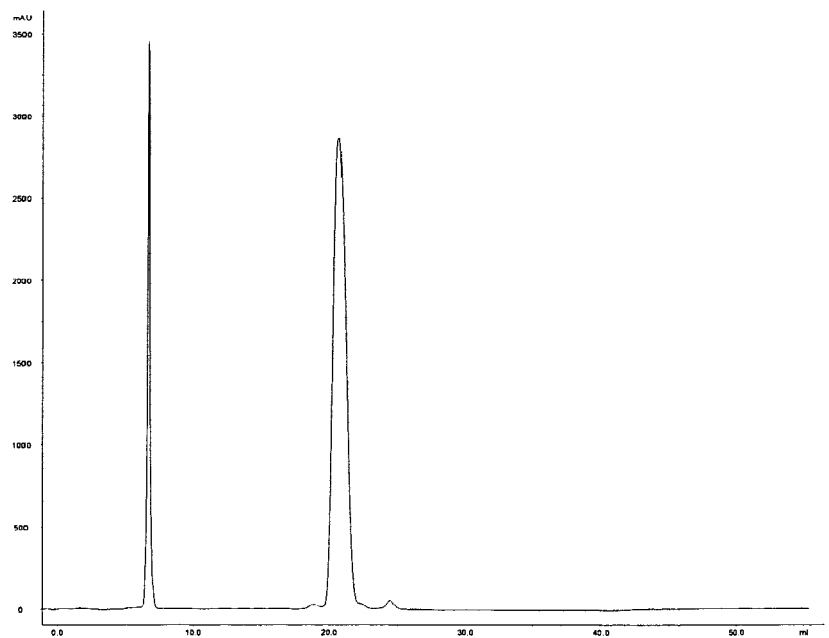
FIG. 20 is a representation of a chromatogram as further described in Example 14.

PEGylation and Purification of m-PEG2-RU-NHS 20K-ssRNA Conjugate or "ruPEG2-20K-ssRNA Conjugate"

m-PEG2-RU-NHS 20K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$-AmCAmACmAGmACmUUmUAmAUmGUmAA-3', SEQ ID NO: 183) and 0.261 ml of 100 mg/mL m-PEG2-RU-NHS 20K polymeric reagent. The m-PEG2-RU-NHS 20K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 20. The concentration of the conjugate was determined by UV spectrophotometry. The purity of the conjugate was confirmed by ion-exchange HPLC. MALDI-TOF analysis was performed to confirm the molecular weight of the conjugate.

Example 15

Figure 21:
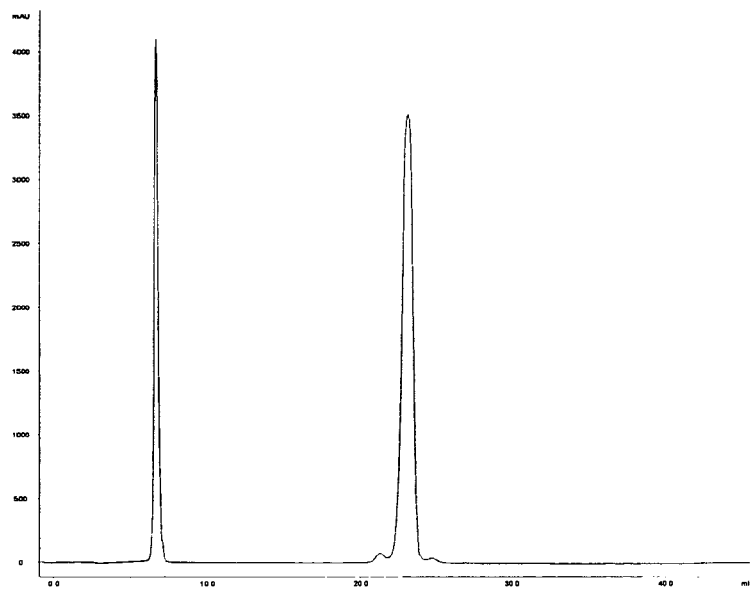
FIG. 21 is a representation of a chromatogram as further described in Example 15.

PEGylation and Purification of mPEG-SBA 5K-ssRNA Conjugate m-PEG-SBA 5K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$-AmCAmACmAGmACmUUmUAmAUmGUmAA-3', SEQ ID NO: 183) and 0.261 ml of 100 mg/mL m-PEG-SBA 5K polymeric reagent. The m-PEG-SBA 5K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-ML with 20 mM Bis-tris, pH 6.8 and purified by anion exchange chromatography (HiTrap Q HP; 1 mL). A linear salt gradient separated the PEGylated ss-RNA from the unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 21. The concentration of the conjugate was determined by UV spectrophotometry. The purity of the conjugate was confirmed by ion-exchange HPLC. MALDI-TOF analysis was performed to confirm the molecular weight of the conjugate.

Example 16

Figure 22:
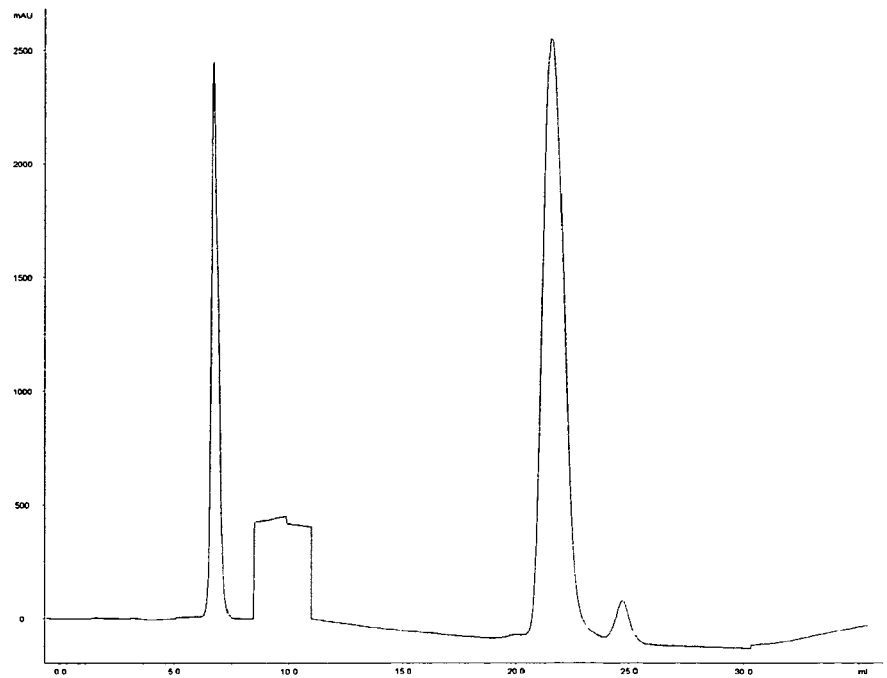
FIG. 22 is a representation of a chromatogram as further described in Example 16.

PEGylation and Purification of m-PEG-SC 20K-ssRNA Conjugate m-PEG-SC 20K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$-AmCAmACmAGmACmUUmUAmAUmGUmAA-3', SEQ ID NO: 183) and 0.261 ml of 100 mg/mL mPEG-SC 20K polymeric reagent. The mPEG-SC 20K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 22. The concentration of the conjugate was determined by UV spectrophotometry. The purity of the conjugate was confirmed by ion-exchange HPLC. MALDI-TOF analysis was performed to confirm the molecular weight of the conjugate.

Example 17

Comparison of Conjugates

A comparison of some of the analytical data of the conjugates prepared in Examples 7 through 16 is provided in Table 9. Purity % was determined by anion exchange HPLC while observed molecular weight (MW) was established using MALDI.

Anion exchange HPLC was carried out using a DIONEX BioLC DNAPac PA-10 column (P/N: 043010, Ser#: 007409; Lot#: 008-20-009) having dimensions of 4 mm×250 mm. Flow rate was set at 1.5 mL/min with a column temperature of 25° C. The detection wavelength was 260 nm. Eluent buffer A was 25 mM Tris/0.5% ACN, pH 8.0/HCl and eluent buffer B was 25 mM Tris/0.5% ACN, NH$_4$Cl: 1.6M, pH 8.0/NH$_4$OH. The eluent profile for the approach designated as "IEX-6" is set forth in Table 10a and the eluent profile for the approach designated as "IEX-8" is set forth in Table 10b.

TABLE 9

Comparison of Conjugates Prepared in Example 7 through 16

| Conjugates | Purity (%) | Calculated MW (kD) | Observed MW (kD) |
| --- | --- | --- | --- |
| CAC 20K-ssRNA (Example 7) | 97 | 26.3 | 27.7 |
| CG 20K-ssRNA (Example 8) | >99 | 26.3 | 27.3 |
| C2 20K-ssRNA (Example 9) | 97 | 26.3 | 27.8 |
| m-PEG-SS 20K-ssRNA (Example 10) | 93 | 26.3 | 26.8 |
| m-PEG-SBC 30K-ssRNA (Example 11) | 90 | 36.3 | 33.7 |
| m-PEG-OPSS 5K-ssRNA (Example 12) | >99 | 11.3 | 12.2 |
| Di-C2 20K-ssRNA (Example 13) | >99 | 46.3 | 48.7 |
| m-PEG2-RU-NHS 20K-ssRNA (Example 14) | 97 | 26.3 | 27.6 |
| m-PEG-SBA 5K-ssRNA (Example 15) | 93 | 11.3 | 11.9 |
| m-PEG-SC 20K-ssRNA (Example 16) | 92 | 26.3 | 26.7 |

TABLE 10a

Eluent Profile for IEX-6 Approach

| Time (minutes) | A | B |
| --- | --- | --- |
| −10 | 85 | 15 |
| 0 | 85 | 15 |
| 3 | 85 | 15 |
| 20 | 66.5 | 33.5 |
| 20.1 | 0 | 100 |
| 26 | 0 | 100 |
| 26.1 | 85 | 15 |
| 26.2 | Stop | |

TABLE 10b

Eluent Profile for IEX-6 Approach

| Time (minutes) | A | B |
| --- | --- | --- |
| −10 | 95 | 5 |
| 0 | 95 | 5 |
| 3 | 95 | 5 |
| 29.3 | 66.5 | 33.5 |
| 29.4 | 0 | 100 |
| 36.4 | 0 | 100 |
| 36.5 | 95 | 5 |
| 36.6 | Stop | |

Example 18

PEG-ssRNA Conjugate Release Kinetics

Figure 23:
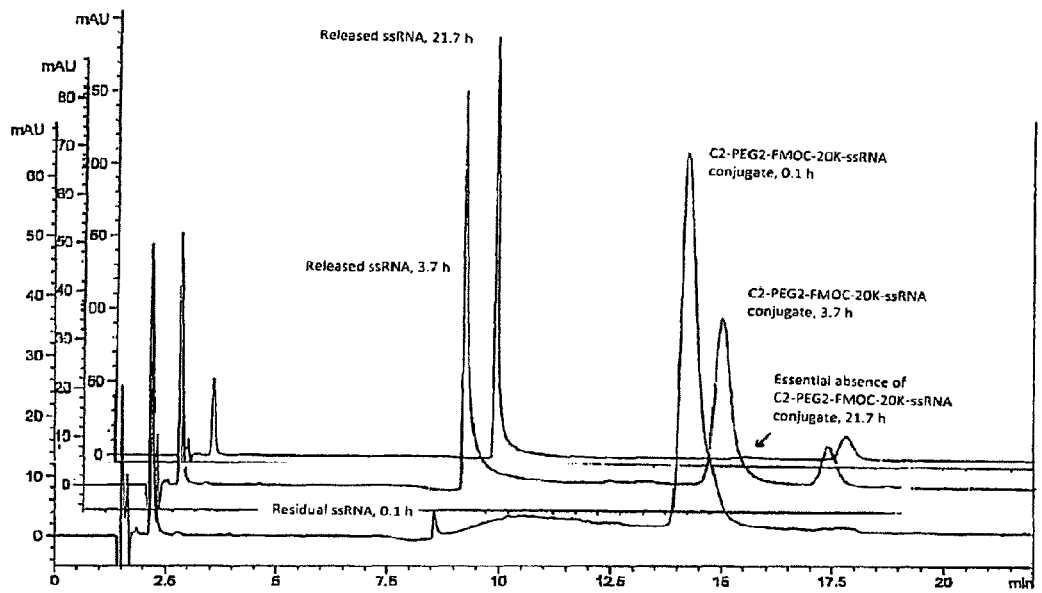
FIG. 23 is a series of chromatograms showing the release of ssRNA from C2-PEG2-FMOC-20K-ssRNA as further described in Example 18.
Figure 24:
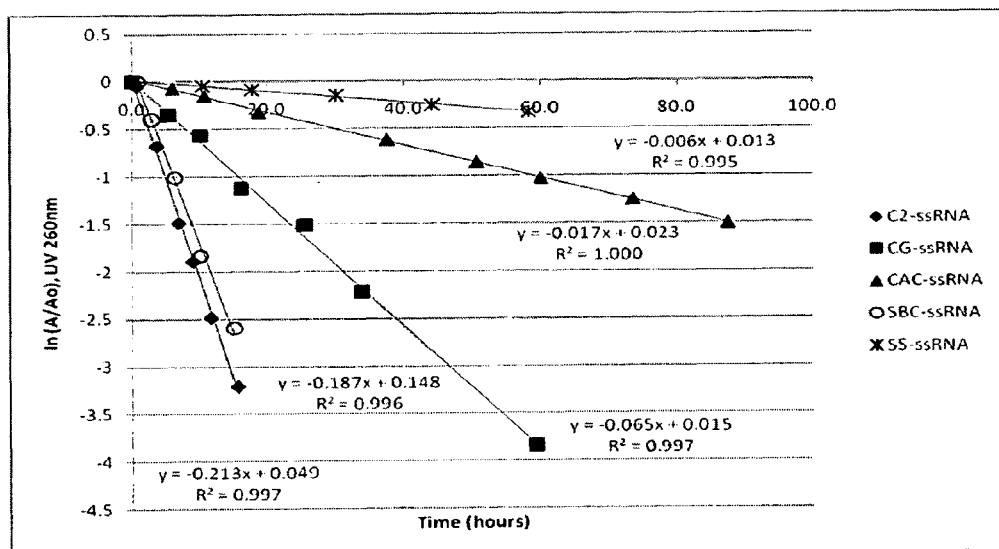
FIG. 24 is a time-concentration plot of PEG-ssRNA conjugates, wherein release kinetics (0.4 M HEPES, pH 7.4, 37° C.) are shown as further described in Example 18.

NH$_2$—C6-ssRNA release from C2-PEG2-FMOC-20K-ssRNA conjugate. C2-PEG2-FMOC-20K-ssRNA conjugate, prepared as described in Example 9, 24 µM in 20 mM Bis-Tris buffer, pH 6.8, NaCl solution (50 µl) was combined with 0.6M HEPES buffer, pH 7.5 (100 µL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-ssRNA conjugate peak with an increase in peaks correlating with released NH$_2$—C6-ssRNA and PEG2-fulvene (see the corresponding chromatograms of FIG. 23). See also the time-concentration plot of FIG. 24 and Table 11.

NH$_2$—C6-ssRNA release from CG-PEG2-FMOC-20K-ssRNA conjugate. CG-PEG2-FMOC-20K-ssRNA conjugate, prepared as described in Example 8, 25 µM in 20 mM Bis-Tris buffer, pH 6.8, NaCl solution (50 µL) was combined with 0.6M HEPES buffer, pH 7.5 (100 µL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-snRNA conjugate peak with an increase in peaks correlating with released NH$_2$—C6-ssRNA and PEG2-fulvene. See Table 11 and the time-concentration plot of FIG. 24.

NH$_2$—C6-ssRNA release from CAC-PEG2-FMOC-20K-snRNA conjugate. CAC-PEG2-FMOC-20K-ssRNA conjugate, prepared as described in Example 7, 24 µM in 20 mM Bis-Tris buffer, pH 6.8, NaCl solution (50 µL) was combined with 0.6M HEPES buffer, pH 7.5 (100 µL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released NH$_2$—C6-ssRNA and PEG2-fulvene. See Table 11 and the time-concentration plot of FIG. 24.

Succinate modified NH$_2$—C6-ssRNA release from SS-PEG-20K-ssRNA conjugate. SS-PEG-20K-ssRNA conjugate, prepared as described in Example 10, 25.8 µM in 20 mM Bis-Tris buffer, pH 6.8, NaCl solution (50 µl) was combined with 0.6M HEPES buffer, pH 7.5 (100 µL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released succinate modified NH$_2$—C6-ssRNA (i.e., COOHCH$_2$CH$_2$CO—NH—C6-ssRNA). See Table 11 and the time-concentration plot of FIG. 24.

NH$_2$—C6-ssRNA release from SBC-PEG-30K-ssRNA conjugate. SBC-PEG-30K-ssRNA conjugate, prepared as described in Example 11, 17.6 µM in 20 mM Bis-Tris buffer, pH 6.8, NaCl solution (50 µL) was combined with 0.6M HEPES buffer, pH 7.5 (100 µL) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released NH$_2$—C6-ssRNA and PEG-phenol. See Table 11 and the time-concentration plot of FIG. 24.

PEG Conjugate Release Results. Release of the PEG-ssRNA conjugates were analyzed by reverse phase HPLC at 260 nm with TEAA water/acetonitrile gradient. Decrease of the conjugate peaks were observed and plotted according to first order rate plot; ln A/A$_0$ (peak area at 260 nm) vs. time (h). The release half-life ($t_{1/2}$) for each conjugate was calculated from the slope (m=−k) of the first order rate plot where $t_{1/2}$=ln 2/k. See Table 11 and the time-concentration plot of FIG. 24.

Glycine conjugates were prepared by dissolving 10 mg PEG2-FMOC-NHS 20K reagent, as labeled, in 50 µL of 1% glycine buffer pH 9. After 15 minutes of incubation, the glycine conjugate was diluted with water (283 µL) and was combined with 0.6M HEPES buffer, pH 7.5 (667 µL) to provide a conjugate solution of 0.4 M HEPES buffer, pH 7.5. Glycine conjugates incubated at 37° C. in HPLC vials and aliquots were injected at various intervals for analysis by gel-permeation chromatography with refractive index detection. See Table 11.

TABLE 11

Release Half-life Observed for Indicated Conjugates in 0.4M HEPES, 37° C.

| | C2-PEG2-FMOC 20K | CG-PEG2-FMOC 20K | CAC-PEG2-FMOC 20K | mPEG-SBC 30K | mPEG-SS 20K |
|---|---|---|---|---|---|
| Gly Conjugate (pH 7.5) | 1.2 h | 5.1 h | 16.5 h | | |
| ssRNA Conjugate (pH 7.4) | 3.3 h | 10.7 h | 39.8 h | 3.7 h | 115.5 h |

OPSS-5K-ssRNA Release Kinetics. Release of the PEG from the OPSS-5K-ssRNA conjugate occurs by a displacement mechanism. The substrate prepared in Example 12 above was carried out using a 50 µL, 47 µM sample in FPLC purification buffer (20 mM Bis-Tris, 200 mM NaCl, pH 6.8) using a releasing buffer: KCl: 2.7 mM, NaCl: 137 mM, phosphate: 10 mM, pH 7.4 with reduced glutathione in releasing buffer, 293 mM, was freshly made and used immediately. 50 µL RNA conjugate buffer was exchanged into releasing buffer via gel filtration; dilute RNA was added to a final volume of 0.3 mL with releasing buffer; the reduced glutathione was added into 0.3 mL RNA conjugate solution. In the final solutions; RNA conjugate concentration: 7.7 µM (estimated); reduced glutathione: 4.8 mM. The mixture was incubated at 37° C. The samples were analyzed by HPLC and the data were analyzed with Prism 4 software assuming a pseudo-first order reaction. The half-life release of the conjugate disulfide under the reduced glutathione conditions described above was 6.3 hours.

Example 19

Preparation of Chitosan 10K/FMOC-CAC 20K Conjugate

Figure 25:
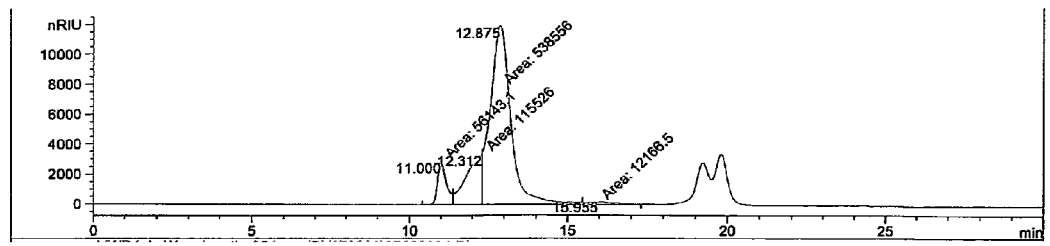
FIG. 25 is a representation of a chromatogram as further described in Example 19.

The pH of the chitosan 10K (MW=10000, 0.05 g, 0.28 mmol) solution in 5 mL of Phosphate Buffered Saline (PBS) was adjusted to pH 6.3 using 1M hydrochloric acid (HCl) or 1M sodium hydroxide (NaOH). To the solution was added 9-hydroxymethyl-4-(mPEG(10,000)-carboxyamide)-7-(3-(mPEG(10,000))carbamoyl-propyl)-N-hydroxysuccinimide polymeric reagent (FMOC-CAC 20K, 0.1 g, 5.0 mmol). The solution was stirred at room temperature. The product was purified by cation exchange chromatography using a POROS 50© cation exchange resin and a 1M sodium chloride (NaCl) solution as an eluent. The collected eluent was dialyzed to remove the excess salt using a SpectraPor MWCO 6-8000 membrane and the resulting solution was evaporated at the reduced pressure. Purified yield 42 mg. The GPC chromatogram (FIG. 25) (Ultrahydrogel 250 column, mobile phase: 0.2M sodium acetate/0.3M acetic acid, flow rate running at 0.5 mL/min, temperature 25° C., refractive index detector) shows peaks at 11.0 minutes, 12.3 minutes, 12.8 minutes, and 15.9 minutes as evidence of at least mono- and di-PEGylation of the chitosan.

Example 20

Preparation of Chitosan 10K/mPEG-SS 20K Conjugate

Figure 26:
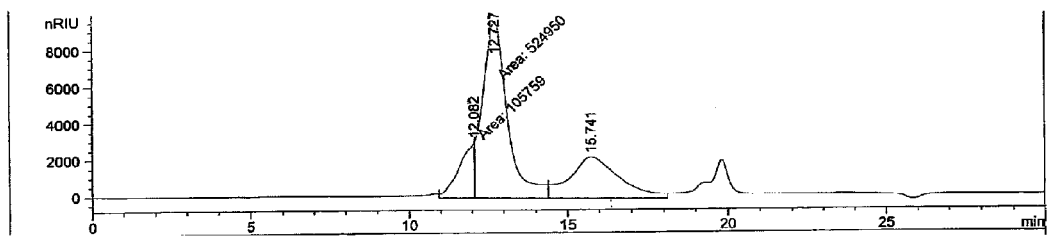
FIG. 26. is a representation of a chromatogram as further described in Example 20.

The pH of the chitosan 10K (MW=10000, 0.1 g, 0.56 mmol) solution in 5 mL of Phosphate Buffered Saline (PBS) was adjusted to pH 6.3 using 1M hydrochloric acid (HCl) or 1M sodium hydroxide (NaOH). To the solution was added mPEG-SS 20 20K polymeric reagent (double ester 20K, 0.2 g, 10.0 µmol). The solution was stirred at room temperature. The product was purified by cation exchange chromatography using a POROS 50© cation exchange resin and a 1M sodium chloride (NaCl) solution as an eluent. The collected eluent was dialyzed to remove the excess salt using a SpectraPor MWCO 6-8000 and the resulting solution was evaporated at the reduced pressure. The GPC chromatogram (FIG. 26) (Ultrahydrogel 250 column, mobile phase: 0.2M sodium acetate/0.3M acetic acid, flow rate 0.5 mL/min, temperature 25° C.; refractive index detector) shows peaks at 12.1 minutes, 12.7 minutes, and 15.7 minutes.

Example 21

Preparation of Chitosan 3-5K/IR Dye 800CW Conjugate

To a solution of the chitosan 3-5K (MW=3-5000, 0.01 g, 55.6 mmol) in 0.5 mL of DI water, 35 µL of 0.5M sodium hydroxide was added. A solution of the IR Dye 800CW NHS ester from LiCor® (MW=1166.2, 0.0025 g, 2.15 mmol) in 125 µL of DMSO (dimethyl sulfoxide) was added to the dissolved chitosan. The solution is stirred at room temperature. The product was purified by cation exchange chromatography using a 1M HCl eluent on a POROS 50© cation exchange resin. The collected acidic fraction was neutralized using 1M NaOH and was dialyzed to remove the excess salt using a SpectraPor MWCO 6-8000 membrane. Next, water was evaporated from the resulting solution at the reduced pressure.

Example 22

Preparation of Chitosan 10K/IR Dye 800CW Conjugate

To a solution of the chitosan 10K (MW=10000, 0.01 g, 55.6 mmol) in 0.5 mL of DI water, 25 µL of 0.5M sodium hydroxide was added. The IR Dye 800CW NHS ester from LiCor® (MW=1166.2, 0.005 g, 4.3 µmol) was dissolved in 250 µL of DMSO (dimethyl sulfoxide). Next, f 60 µL of the resulting solution is removed and added to the dissolved chitosan. The solution is stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next, water was evaporated from the resulting solution at the reduced pressure.

Example 23

Preparation of Chitosan 3-5K/mPEG-BTC 5K and IR Dye 800CW Conjugate

A solution of the chitosan 3-5K/mPEG-BTC 5K conjugate (MW=18-20000, 0.01 g) in 0.5 mL of DI water was prepared. The IR Dye 800CW NHS ester from LiCor® (MW=1166.2, 0.005 g, 4.3 µmol) was dissolved in 250 µL of DMSO (dimethyl sulfoxide). Next, 125 µL of the resulting solution was removed and added to the dissolved chitosan. The solution was stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next, water was evaporated from the resulting solution at the reduced pressure.

Example 24

Preparation of Chitosan 10K/mPEG-BTC 5K and IR Dye 800CW Conjugate

A solution of the chitosan 10K/mPEG-BTC 5K conjugate (MW=25000, 0.01 g) in 0.5 mL of DI water was prepared. The IR Dye 800CW NHS ester from LiCor® (MW=1166.2, 0.005 g, 4.3 µmol) was dissolved in 250 µL of DMSO (dimethyl sulfoxide). Next, 60 µL of the resulting solution was removed and added to the dissolved chitosan. The solution is stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next water was evaporated from the resulting solution at the reduced pressure.

Example 25

Preparation of Chitosan 3-5K/mPEG-butrALD 5K Conjugate

Figure 27:
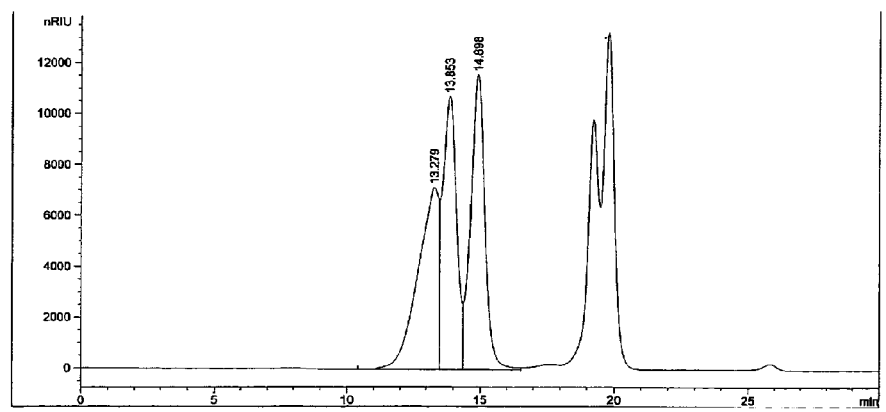
FIG. 27 is a representation of a chromatogram as further described in Example 25.

Chitosan 3-5K (MW=3-5000, 0.1 g, 0.56 mmol) was dissolved in 5 mL of DI water and the pH of the solution was adjusted to pH 8.4 using 1M sodium hydroxide (NaOH). To the solution was added mPEG-butrALD 5K (MW=5000, 1.39 g, 0.278 mmol). The solution was stirred at room temperature for one hour and then added 0.21 g sodium borohydride (5.56 mmol) was added and the mixture was stirred overnight. The reaction mixture was transferred to SpectraPor MW6-8000 dialysis tubing and dialyzed versus DI water. The dialysate is changed every hour for a total of four washes. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution is transferred to a round bottom flask and the solvent was evaporated at the reduced pressure. The GPC chromatogram (FIG. 27) (Ultrahydrogel 250 column, mobile phase: 0.2M sodium acetate/0.3M acetic acid, flow rate 0.5 mL/min, temperature 25° C.; refractive index detector) shows peaks at 13.2 minutes, 13.8 minutes, and 14.8 minutes.

Example 26

Preparation of Chitosan 10K/mPEG-butrALD 5K Conjugate

Figure 28:
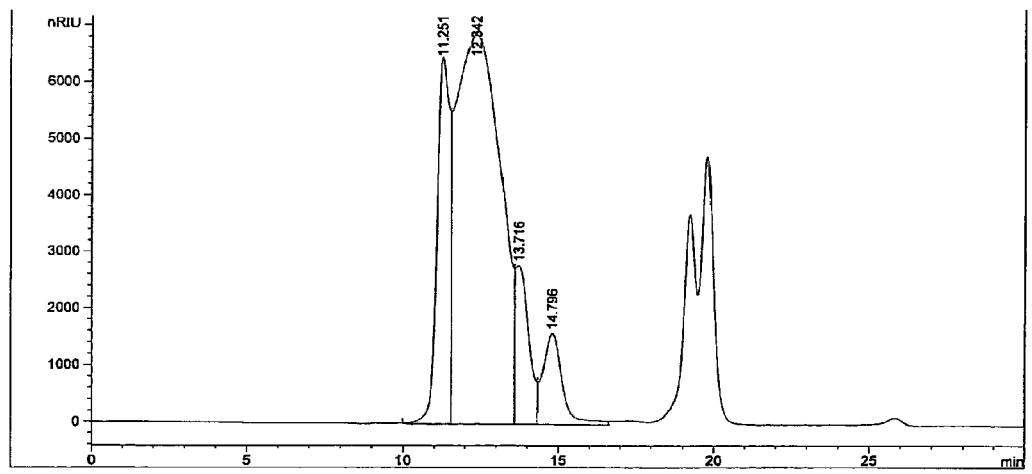
FIG. 28 is a representation of a chromatogram as further described in Example 26.

Chitosan 10K (MW=10000, 0.1 g, 0.56 mmol) was dissolved in 5 mL of DI water and the pH of the solution was adjusted to pH 6.3 using 1M sodium hydroxide (NaOH). To the solution was added mPEG-butrALD 5K (MW=5000, 1.39 g, 0.278 mmol). The solution was stirred at room temperature for one hour and then 0.21 g sodium borohydride (5.56 mmol) was added and the mixture was stirred overnight. The reaction mixture was transferred to SpectraPor MW6-8000 dialysis tubing and dialyzed versus DI water. The dialysate is changed every hour for a total of four washes. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution is transferred to a round bottom flask and water was evaporated at the reduced pressure. The GPC chromatogram (FIG. 28) (Ultrahydrogel 250 column, mobile phase: 0.2M sodium acetate/0.3M acetic acid, flow rate 0.5 mL/min, temperature 25° C.; refractive index detector) shows peaks at 11.2 minutes, 12.3 minutes, 13.7 minutes, and 14.7 minutes.

Example 27

Preparation of Chitosan 3-5K/mPEG-BTC 5K Conjugate

Chitosan 3-5K (MW=3-5000, 0.1 g, 0.56 mmol) in 10 mL of 0.1M boric acid and adjusted solution to pH 8.5 using 0.1M sodium hydroxide (NaOH). To the solution was added mPEG-BTC 5K (MW=5000, 0.77 g, 0.14 mmol). The solution was stirred at room temperature overnight. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution was transferred to a round bottom flask and water was evaporated at the reduced pressure. The GPC chromatogram (not shown) (Ultrahydrogel 250 column, mobile phase: 0.2M sodium acetate/0.3M acetic acid, flow rate 0.5 mL/min, temperature 25° C.; refractive index detector) shows peaks at 13.2 minutes, 14.4 minutes, and 17.1 minutes indicating mono-, di- and tri-PEGylation.

Example 28

Preparation of Chitosan 10K/mPEG-BTC 5K Conjugate

Chitosan 10K (MW=10000, 0.1 g, 0.56 mmol) was dissolved in 10 mL of 0.1M boric acid solution and the pH of the solution was adjusted solution to pH 6.5 using 0.1 M sodium hydroxide (NaOH). To the solution was added mPEG-BTC 5K polymeric reagent (MW=5000, 0.77 g, 0.14 mmol). The solution was stirred at room temperature overnight. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL DI water and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution is transferred to a round bottom flask and water was evaporated at reduced pressure. The GPC chromatogram (not shown) (Ultrahydrogel 250 column, mobile phase: 0.2M sodium acetate/0.3M acetic acid, flow rate 0.5 mL/min, temperature 25° C.; refractive index detector) shows peaks at 11.4 minutes, 12.5 minutes, 13.5 minutes and 14.9 minutes indicating mono-, di- and tri-PEGylation.

Example 29

Preparation of Chitosan and PEG-Chitosan/siRNA Ionic Complexes

The chitosan or chitosan/PEG conjugate was dissolved in PBS buffer at pH 5.3, 6.3, or 7.3 with the resulting solution having a final concentration of 5 mg/mL. The siRNA duplex was dissolved in DI water at a final concentration of 2.5 mg/mL. The resulting ionic complexes were prepared by the addition of the specific quantities of the chitosan or chitosan/PEG conjugate solution (listed in the Table 12A to 12D) to the specific quantities of the solution of siRNA.

TABLE 12A

Summary of data for Chitosan 3-5K/siRNA Ionic Complexes

| Chitosan 3-5K (µL) | siRNA (µL) | PBS (µL) | Ratio (N:P) |
|---|---|---|---|
| 3 | 3 | 9 | 1:1 |
| 4.5 | 3 | 7.5 | 1.5:1 |
| 6 | 3 | 6 | 2:1 |
| 7.5 | 3 | 4.5 | 2.5:1 |

TABLE 12B

Summary of data for Chitosan 10K/siRNA Ionic Complexes

| Chitosan 10K (µL) | siRNA (µL) | PBS (µL) | Ratio (N:P) |
|---|---|---|---|
| 1.5 | 3 | 10.5 | 1:1 |
| 3 | 3 | 9 | 2:1 |
| 4.5 | 3 | 7.5 | 3:1 |
| 6 | 3 | 6 | 4:1 |
| 7.5 | 3 | 4.5 | 5:1 |

TABLE 12C

Summary of data for PEG-Chitosan 3-5K/siRNA Ionic Complexes

| PEG-Chitosan 3-5K (µL) | siRNA (µL) | PBS (µL) | Ratio (N:P) |
|---|---|---|---|
| 3 | 3 | 9 | 1:1 |
| 4.5 | 3 | 7.5 | 1.5:1 |
| 6 | 3 | 6 | 2:1 |
| 7.5 | 3 | 4.5 | 2.5:1 |

TABLE 12D

Summary of data for PEG-Chitosan 10K/siRNA Ionic Complexes

| PEG-Chitosan 10K (μL) | siRNA (μL) | PBS (μL) | Ratio (N:P) |
|---|---|---|---|
| 1.5 | 3 | 10.5 | 1:1 |
| 3 | 3 | 9 | 2:1 |
| 4.5 | 3 | 7.5 | 3:1 |
| 6 | 3 | 6 | 4:1 |
| 7.5 | 3 | 4.5 | 5:1 |

Evaluation of the prepared chitosan and chitosan-PEG complexes with siRNAs is described in the Example 35.

Example 30

PEG-Chitosan Release Kinetics

CAC-PEG2-FMOC-20K-Chitosan-10K conjugate release. CAC-PEG2-FMOC-20K-Chitosan-10K conjugate, prepared as described in Example 19, 1 mg in 20 mM Bis-Tris, pH 6.8, NaCl solution (167 μL) was combined with 0.6M HEPES, pH 7.5 (333 μL) to provide a conjugate solution of 0.4 M HEPES, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-Chitosan conjugate peaks with an increase in peak correlating with released and PEG2-fulvene.

Release of the PEG-Chitosan conjugate was analyzed by reverse phase HPLC at 260 nm with TEAA water/acetonitrile gradient. Increase of the PEG-fulvene peak was observed and plotted according to first order rate plot; In $A/A_0$ (peak area at 260 nm) vs. time (h). The release half-life ($t_{1/2}$) for each conjugate was calculated from the slope (m=k) of the first order rate plot where $t_{1/2}=\ln 2/k$. Data provided in Table 13.

TABLE 13

Release Half-life Observed for Indicated Conjugates in 0.4M HEPES, 37° C.

| | C2-PEG2-FMOC 20K | CG-PEG2-FMOC 20K | CAC-PEG2-FMOC 20K | mPEG-SBC 30K | mPEG-SS 20K |
|---|---|---|---|---|---|
| CAC-Chitosan Conjugate, pH 7.4 | NA | NA | 2.4 h* | NA | NA |

(*Calculated from limited data, t = 0 and t = 7.2 h. NA = Data not available)

Example 31

Synthesis of an Oligomer Having an Ortho Pyridyl Disulfide (OPSS) Active Group and a RGD Peptide Targeting Moiety Following the reaction schematic shown below, the synthesis of an oligomer having an ortho pyridyl disulfide (OPSS) active group and a RGD peptide targeting moiety was conducted.

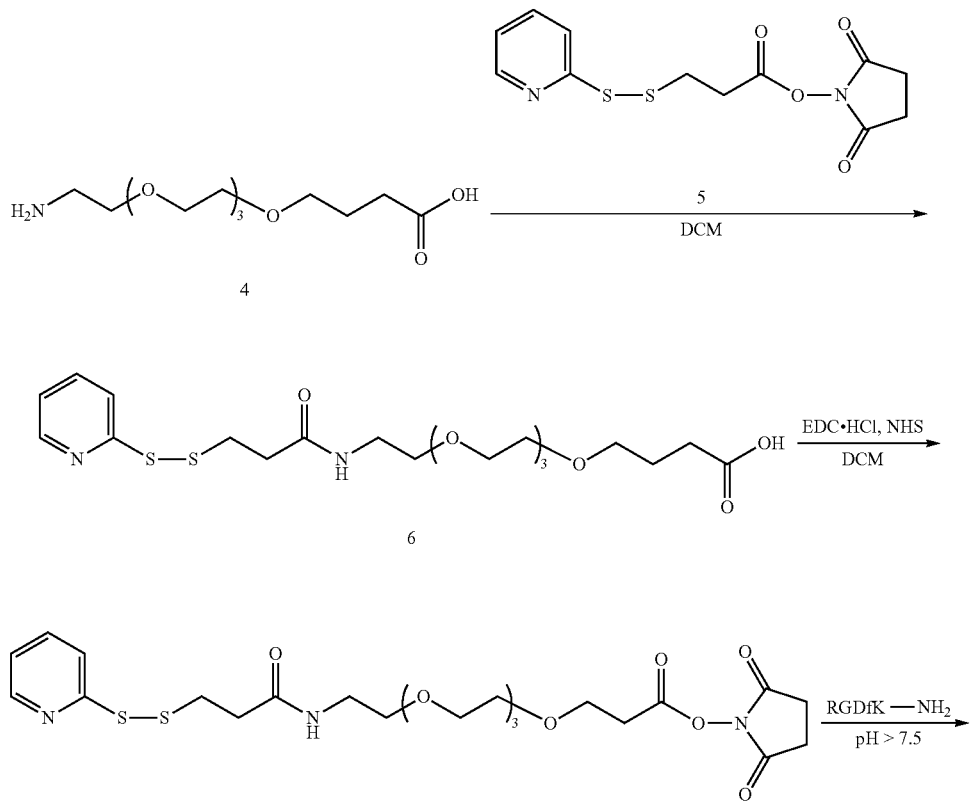

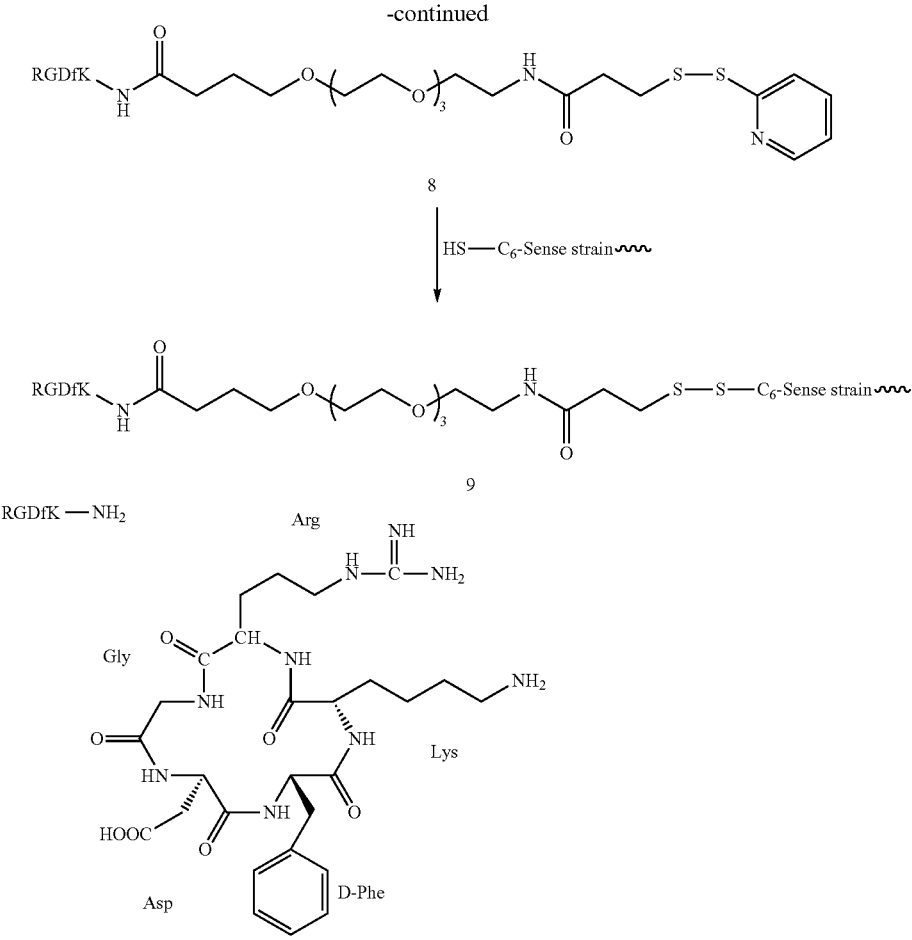

4-(2-(2-(3-(pyridin-2-yldisulfanyl)propanamido)ethoxy)ethoxy)butanoic acid (Compound 6)

4-(2-(2-aminoethoxy)ethoxy)butanoic acid (Compound 4) (F.W. 312.37, 100 mg, 0.377 mmole) in 20 mL of anhydrous toluene was azetropically distilled under reduced pressure at 60° C. on a rotary evaporator. The azeotropic distillation was repeated with 20 mL of anhydrous toluene. Then, the resulting residue was dissolved in anhydrous DCM (20 ml). To the above solution was added N-succinimidyl-3-(2-pyridithio) propionate (Compound 5) (SDPD, F.W.265.3, 100 mg, 0.32 mmole) and triethylamine (105 μl, 0.75 mmole). The mixture was allowed to stand for overnight under stirring at room temperature. TLC showed the disappearance of SPDP. The reaction solution was washed with diluted phosphoric acid (pH4, 5 ml×2). The organic phase was dried over anhydrous $Na_2SO_4$ and concentrated under reduced pressure. The resulting residue was subject to flash chromatography on a Biotage system, giving 140 mg of Compound 6, purity>95% (HPLC).

$^1$H NMR in $CDCl_3$, δ ppm: 8.49 (1H, s), 7.74 (1H, d), 7.69 (1H, m), 7.15 (1H, q), 3.80 (2H, t), 3.64 (12H, m), 3.59 (2H, t), 3.46 (2H, dd), 3.07 (2H, t), 2.64 (4H, m). ESI-MS: [M+H]$^+$ 417.

N-(2-(2-(4-(2,5-dioxopyrrolidin-1-yl)-4-oxobutoxy)ethoxy)ethyl)-3-(pyridin-2-yldisulfanyl)propanamide (Compound 7)

Compound 6 (15 mg, 0.036 mmol) was dissolved in 10 mL of anhydrous DCM. To the above solution were added NHS (4.54 mg, 1.05 equiv.) and EDC hydrochloride (7.25 mg, 1.10 equiv.), respectively. The mixture was stirred for one day at room temperature. Reverse phase HPLC analysis showed that the reaction was complete. The reaction solution was washed with diluted phosphoric acid (pH 4, 10 ml×2). Organic phase was dried over anhydrous $Na_2SO_4$ and concentrated under reduced pressure, yielding syrup Compound 7 (15 mg, 74.5%), substitution 85%. $^1$H NMR in $CDCl_3$, δ ppm: 8.49 (1H, s), 7.66 (2H, m), 7.12 (1H, m), 6.89 (1H, b), 3.86 (1H, t), 3.64 (12H, m), 3.59 (2H, t), 3.46 (2H, dd), 3.08 (2H, t), 2.89 (2H, t), 2.84 (3.4H, s), 2.62 (2H, t). ESI-MS: [M+H]$^+$ 560.

Conjugation of OPSS-TEG-SPA with cRGDfK

OPSS-TEG-SPA (5.6 mg, 0.010 mmol) [TEG representing a tetra(ethylene oxide)] was mixed with cRGDfK peptide (3.0 mg, 0.005 mmol) in 100 mM carbonate-bicarbonate buffer (pH 10.1). The mixture was allowed to stand for three hours at room temperature. The reaction mixture was analyzed on a Zorbax C18 (4.6×50 mm) with a gradient of 10-60% ACN in 0.1% TFA and flow rate 1.5 ml/min. RGDfK Conjugate with a M.W. 1047 was formed with a retention time of 1.99 mM (40.6%, UV 254 nm), compared to 2.17 min for hydrolyzed form (20.1%, UV 254 nm), and 8.13 min for additional component (33%, UV 254 nm). The RDGfK with TEG linker and active OPSS group can be conjugated with siRNA having an active thiol functionality, such as the hexyl thiol modified siRNA described herein. By way of illustration, see Example 32.

Example 32 ssRNA-C$_6$—SS-TEG-(KfDGR-N Terminus) Conjugate ssRNA-C$_6$—SS-TEG-(KfDGR-N terminus) conjugate was produced by the reduction of 5' capped-RNA (5'-C6-S—SC6-AmCAmACmAGmACmUUmUAmAUmGU-mAA-3', SEQ ID NO: 186) with Tris(2-Carboxyethyl)phosphine Hydrochloride (TCEP.HCl) followed by the coupling with OPSS-TEG-KfDGR-(N terminus).

To reduce 5'-capped-RNA, a 0.015-ML solution containing 0.003 mL 5' capped-RNA, 0.003-ML, 1 M, EPPS, pH 8.5 and 0.007-ML 64 mM TCEP.HCl was incubated at 25° C. without stirring for 60 minutes. After 60 minutes incubation, 0.015-ML reaction mixture was loaded on a desalting column (pre-equilibrated with 20 mM HEPES, 50 mM NaCl, pH 7.4) and rinsed with 0.045-ML buffer (20 mM HEPES, 50 mM NaCl, pH 7.4). A total of 0.06-ML solution containing RNA with free thiol group (5'-HSC6-AmCAmA-CmAGmACmUUmUAmAUmGUmAA-3'(SEQ ID NO: 195) was collected.

To couple reduced RNA with OPSS-TEG-(KfDGR-N terminus), 0.005-mL of reduced oligo from the above reaction was mixed with 0.005-ML solution containing a mixture of OPSS-TEG-(KfDGR-N terminus) and OPSS-TEG-propionic acid. The reaction mixture was incubated at 25° C. without stirring for three hours. Analysis of the reaction mixture by ion-exchange HPLC revealed a new peak (RT=14.6 min, 26% UV 260 nm) supporting the expected formation of ssRNA-C$_6$—SS-TEG-(KfDGR-N terminus) conjugate. An additional peak was observed (RT=15.7 min, 45% UV 260 nm) and correlated with separately prepared impurity marker for ssRNA-C$_6$—SS-TEG-propionic acid conjugate. The ssRNA-C$_6$—SS-TEG-propionic acid conjugate was prepared as an impurity marker by coupling reduced RNA with OPSS-TEG-propionic acid.

Example 33

Additional Syntheses of siRNA, Chitosan, and PEGs Having Targeting Moieties

Targeting moieties may be attached to either the siRNA, chitosan (or other positively charged polymer described herein), or PEGs including heterobifunctional PEGs that may also be attached at the remote end to either chitosan or siRNA.

Pemeterxed targeting moiety attached to PEG. Using the following reaction scheme, a pemeterxed moiety (i.e., a moiety having pemeterxed activity) can be attached to a polymer.

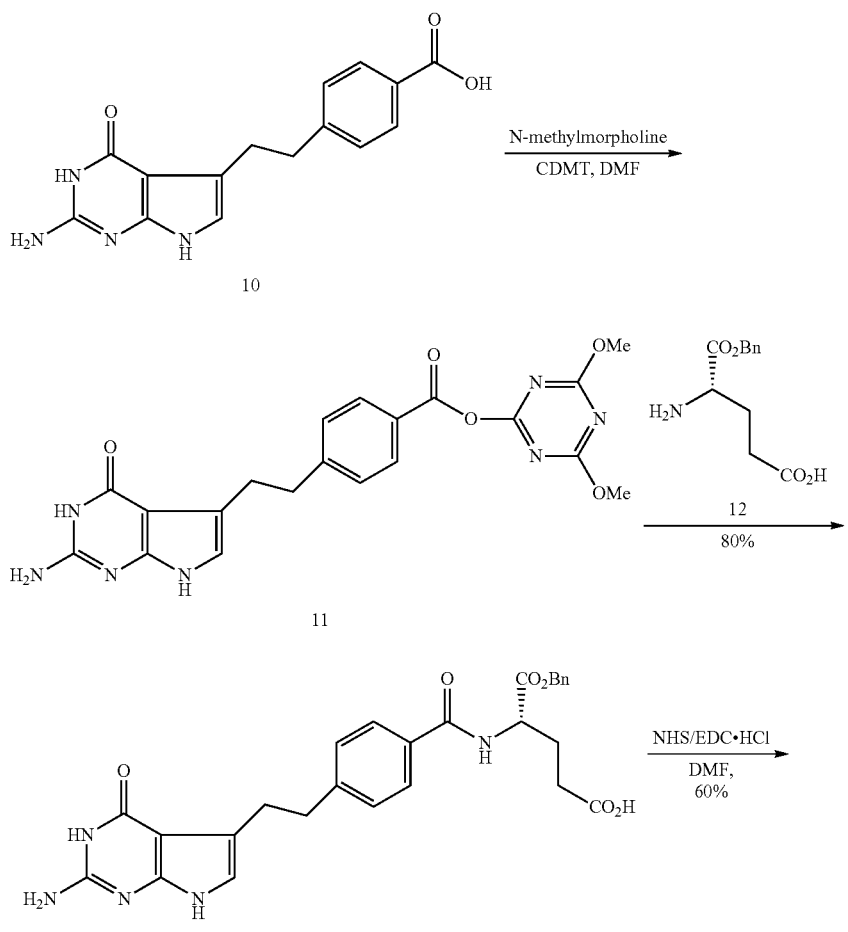

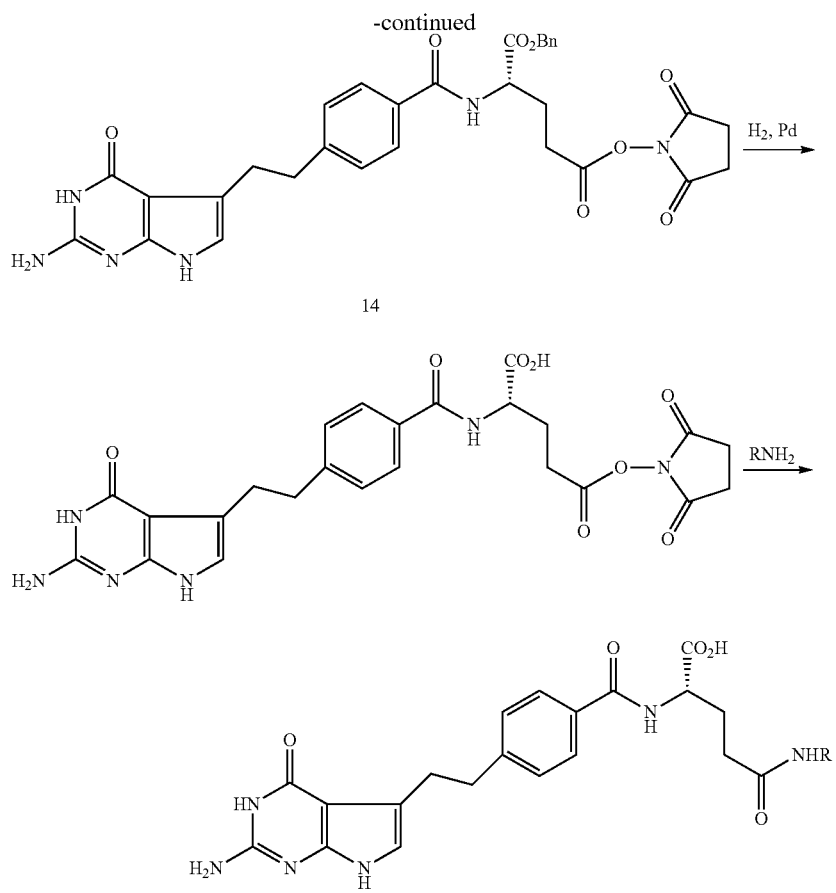

where R = chitosan, PEG, or siRNA (S)-4-(4-(2-(2-amino-4-oxo-4,7-dihydro-3H-pyrrolo[2,3-d]pyrimidin-5-yl)ethyl)benzamido)-5-(benzyloxy)-5-oxopentanoic acid (Compound 13)

To a solution of 4-[2-(2-amino-4,7-dihydro-4-oxo-1H-pyrrolo[2,3-d]-pyrimidin-5-yl)ethyl]benzoic acid (38.4 mg, 0.129 mmol) in 5 mL of DMF was added N-methylmorpholine (40.4 mg, 0.399 mmol), followed by the addition of 2-chloro-4,6-dimethoxy-1,3,5-triazine (22.64 mg, 0.129 mmol). The resulting mixture was stirred for 1.5 hours at 25° C., at which time HPLC showed that the reaction was complete. L-glutamic acid γ-benzyl ester (30.6 mg, 0.129 mmol) was added, and stirring was continued at 25° C. until complete conversion of precursor was determined by HPLC (around two hours). To the reaction mixture was added 10 mL of methylene chloride and 10 ml of deionized water, and the mixture was stirred for 15 minutes. The layers were separated. The aqueous layer was extracted with DCM (10 ml×2). The organic phases were combined. The solution was concentrated on rotary-evaporator under reduced pressure. The resulting residue was subjected to flash chromatography on a Biotage system. Yield: 55 mg, 82%. $^1$HNMR in $d^6$-DMSO, δ ppm: 10.61 (1H, s), 10.20 (1H, s), 8.72 (1H, d, J=10 Hz), 7.78 (2H, d, J=5 Hz), 7.35 (5H, m), 7.30 (2H, m), 6.30 (1H, s), 6.07 (2H, s), 5.14 (2H, s), 3.86 (1H, m), 2.97 (2H, t), 2.84 (2H, t), 2.20 (2H, s), 2.02 (1H, m), 1.95 (1H, m). ESI-MS: 518 [M+H]$^+$.

(S)-1-benzyl 5-(2,5-dioxopyrrolidin-1-yl)2-(4-(2-(2-amino-4-oxo-4,7-dihydro-3H-pyrrolo[2,3-d]pyrimidin-5-yl)ethyl)benzamido)pentanedioate (Compound 15)

A mixture of Compound 13 (55 mg, 0.11 mmol), NHS (15.4 mg, 0.132 mmol) and EDC hydrochloride (27 mg, 0.140 mmol) in anhydrous DMF was stirred at room temperature for two days. TLC showed the disappearance of starting material. Solvent was stripped off under reduced pressure. The resulting residue was dissolved in DCM (50 mL). The solution was washed with diluted phosphoric acid (pH 4) (50 mL×3). The organic phase was dried over anhydrous Na$_2$SO$_4$. The solvent was removed, resulting in 48 mg residue, yield 60%, substitution 80%. $^1$HNMR in $d^6$-DMSO, δ ppm: 10.65 (1H, s), 10.21 (1H, s), 8.77 (1H, d, J=10 Hz), 7.79 (2H, d, J=5 Hz), 7.34 (5H, m), 7.30 (2H, m), 6.30 (1H, s), 6.08 (2H, s), 5.16 (2H, s), 2.97 (2H, t), 2.89 (2H, t), 2.81 (3.2H, s) 236 (2H, m), 2.20 (2H, s). ESI-MS: 615 [M+H]$^+$.

Conjugation to chitosan amine groups, to PEG amines or to aminohexyl siRNAs is carried out in a similar manner to other reactions of amine substituted polymers described herein, e.g., see Examples 1-3. The following example demonstrates the successful attachment of the above synthesized activated targeting moiety to a heterobifunctional 20 kD Conjugation of NH$_2$—PEG-BA 20K and Pemeterxed-NHS Ester NH$_2$—PEG-butric acid 20K (0.25 g, 12.5 µmol) is added to 1 mL of 0.1M boric acid, the solution is adjusted to pH 9 using 1M NaOH. To the solution is added 0.375 mL of a 40 mg/mL pemeterxed-NHS ester (24.4 µmol) dropwise over 25 minutes while maintaining a constant pH of 9. The reaction mixture is allowed to stir at room temperature for two hours. To the solution is added 0.5 g of sodium chloride and adjusted to pH 3 using 1M HCl. The product is extracted using three aliquots of 5 mL of DCM. The collected DCM fractions are combined and the DCM is removed under vacuum. The precipitated product is analyzed by GPC Ultrahydrogel 250 column running 0.01M HEPES buffer at 0.5 mL/min at 75° C. to assess the remaining unreacted amine. A peak at 12.7 minutes corresponds to the product of pemeterxed-PEG-BA, and unreacted NH$_2$-PEG-BA has a retention time of 30.4 minutes. There is no peak at 30.4 minutes confirming that the PEG amine had been fully substituted with the Pemeterxed moiety.

Activation of Pemeterxed-PEG-BA with NHS.

The above dried product is redissolved in 2 mL of DCM, to the solution is added 1.6 mg of NHS (N-hydroxysuccinimide, 14 µmol) and 3.3 mg of DCC (N,N'-dicyclohexylcarbodiimide, 16.2 µmol) and stirred overnight. The product is removed by precipitation through the addition of IPA (2-propanol) and collected by filtration. $^1$H-NMR (CDCl$_3$, 500 MHz): δ (ppm) 2.82 (s, 4H, CO—CH$_2$—CH$_2$—CO on NHS); 2.92 (t, CH$_2$ on β-carbon to NHS ester); 3.64 (s, PEG backbone).

Phospholipids

Following the reaction schematic below, 1,2-dipalmitoyl-glycero-3-phosphorimidazolide was prepared.

1,2-dipalmitoyl-glycero-3-phosphate monosodium salt (MW=670.87, 50 mg, 74.5 µmol) was dissolved in 5 mL chloroform, to the solution was added 76 mg imidazole (1.1 mmol), 230 mg DCC (1.1 mmol), 151 mg N-hydroxybenzotriazole (HOBt, 1.1 mmol), and 50 µL TEA. The solution was stirred at 60° C. overnight. The product was precipitated by addition of acetone and water giving a fine white precipitate. The precipitate was collected by centrifugation at 13,200 rpm for ten minutes. $^1$H-NMR (CDCl3, 500 MHz): δ (ppm) 0.88 (t, 6H, —CH$_3$); 1.25 (bm, —CH$_2$—); 7.75 (d, 1H); 7.93 (d, 1H); 8.15 (d, 1H).

DSPE Targeting Moieties and Their Conjugates

Following the reaction schematic below, a DSPE targeting moiety and its conjugate can be prepared.

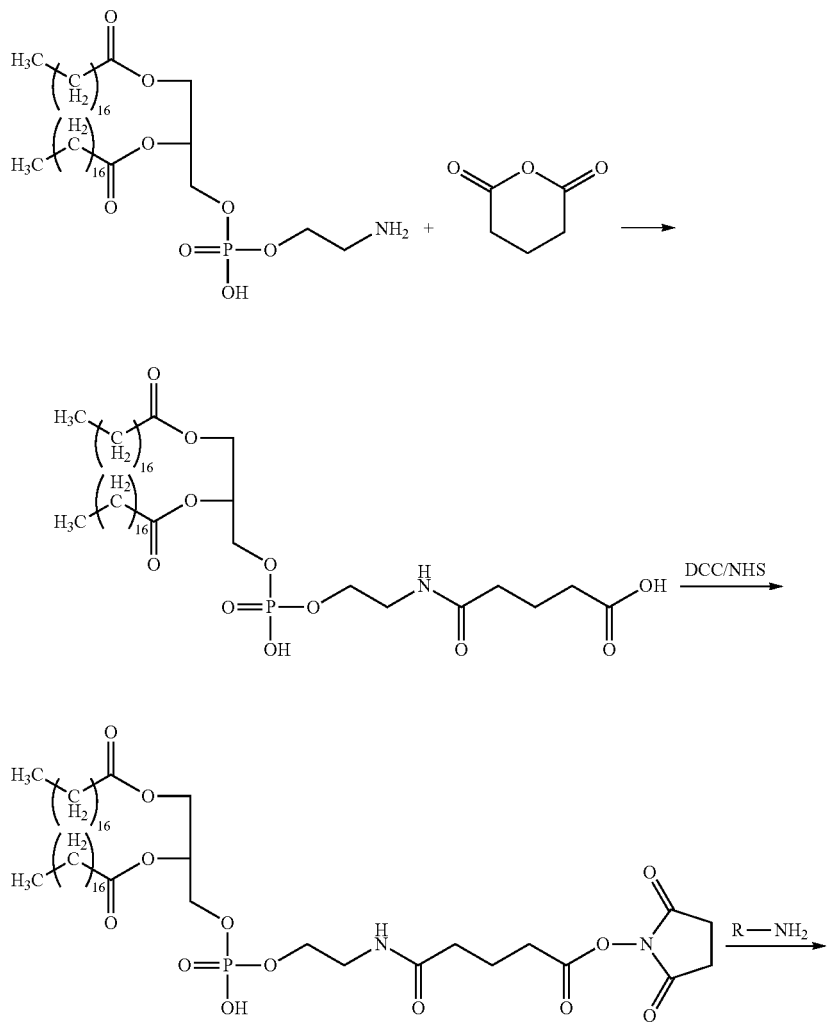

-continued

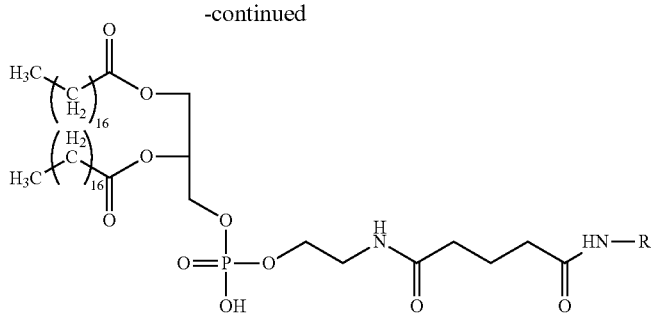

Where R—NH₂ is chitosan, PEG—NH₂ or NH₂-hexyl-siRNA

Preparation of 1,2-distearoyl-N-succinimidyl-glutaryl-phosphatidylethanolamine (DSPE-NHS)

To the solution of 5 mL of chloroform was added 100 mg of 1,2-distearoyl-sn-glyvero-3-phosphoethanolamine (DSPE, 0.133 mmol), 36 mg of 4-dimethylamino pyridine (DMAP, 0.294 mmol), 17 mg of glutaric anhydride (0.147 mmol), and 28 μL of triethylamine (TEA). The reaction mixture was stirred at 60° C. for 4 hours. DSPE was precipitated by the addition of 20 mL of acetone and the product was collected by filtration.

The dried product was redissolved in 1 mL of chloroform and to the solution was added 38 mg of DCC and 18 mg of NHS. The reaction was stirred at room temperature overnight. To the solution was added 10 mL of acetone and then filtered to remove any insoluble material. The acetone/chloroform mixture was removed under vacuum. $^1$H-NMR (CDCl₃, 500 MHz): δ (ppm) 0.88 (t, 6H, —CH₃); 1.25 (s, —CH₂—); 2.07 (m, 2H, —CH₂— γ-carbon on glutaric anhydride); 2.82 (s, 4H, CO—CH₂—CH₂—CO on NHS); 2.92 (t, CH₂ on β-carbon to NHS ester).

Conjugation to chitosan amine groups, to PEG amines or to aminohexyl siRNAs is carried out in a similar manner to other reactions of amine substituted polymers described herein, e.g., see Examples 1-3.

Example 34

Biological Evaluation of Conjugates

Methods. The siRNA sequence is directed against Sjogren syndrome antigen B (SSB) gene.

```
                                        (SEQ ID NO: 191)
Sense:     5'-AmCAmACmAGmACmUUmUAmAUmGUmAA-3'.

(SEQ ID NO: 192)
Antisense: 3'-mUGmUUmGUmCUmGAmAAmUUmACmAUmU-5'.
```

(Lower case 'm' indicates "2'OMe" modification).

Figure 29:
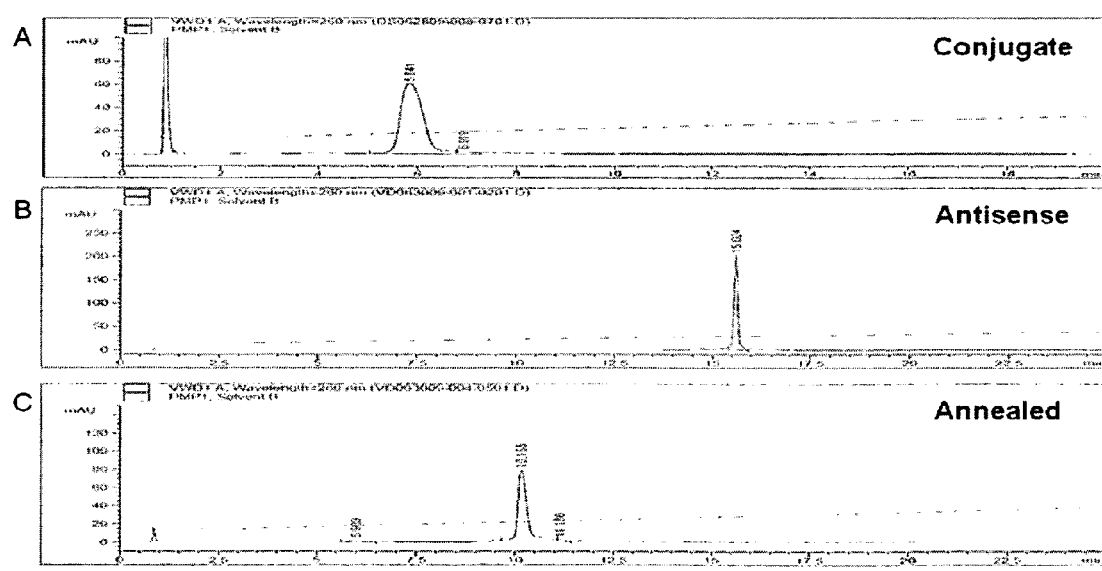
FIG. 29 shows three panels, A, B and C corresponding to conjugate, antisense and annealed, as further described in Example 34.

Annealing conjugates. The antisense strand was re-suspended in siRNA buffer (Thermo Scientific, USA). RNA concentration of the sense-strand-polymer conjugates was determined using RiboGreen (Invitrogen, USA) as per manufacturer's instructions. RNA sense strand-conjugates were mixed with antisense at eqimolar concentrations and heated to 50° C. for five minutes followed by gradual cooling to room temperature. Displayed in FIG. 29 are results of ion exchange chromatography of conjugate CAC-FMOC 20K; 5'NH-sense (panel A), antisense (panel B), conjugate annealed with antisense (panel C).

Cell line and transfection. Human embryonic kidney 293 cells were plated on 12-well plates ($1.5 \times 10^5$ cells per well) in MEMα supplemented with 10% FBS. The following day, medium was changed to reduced serum OPTI-MEM (Gibco, Carlsbad, Calif., USA). Cells were treated with 100 nM annealed conjugate complexed with Lipofectamine 2000 as per manufacturer's instruction. Four hours after treatment, FBS was added to each well to a final concentration of 2%. Cells were harvested 48 hours after conjugate treatment and RNA isolated using Tri-Reagent (Applied Biosystems, CA, USA) as per manufacturer's instructions.

RT-qPCR. RNA yield was determined spectrophotometrically by measuring absorbance at 260 nm and RNA quality was assessed by agarose gel electrophoresis. Equal amounts of RNA (600 μgs) was converted to cDNA using High-Capacity cDNA Reverse transcription Kit (Applied Biosystems, USA) as per manufacturer's instructions. Levels of SSB mRNA in each sample were determined using an ABI7300 Q-PCR instrument and TaqMan assay reagents from Applied Biosystems (SSB assay cat. #4331182, Hs00427601 ml and GAPDH assay cat. #4326317E).

Figure 30:
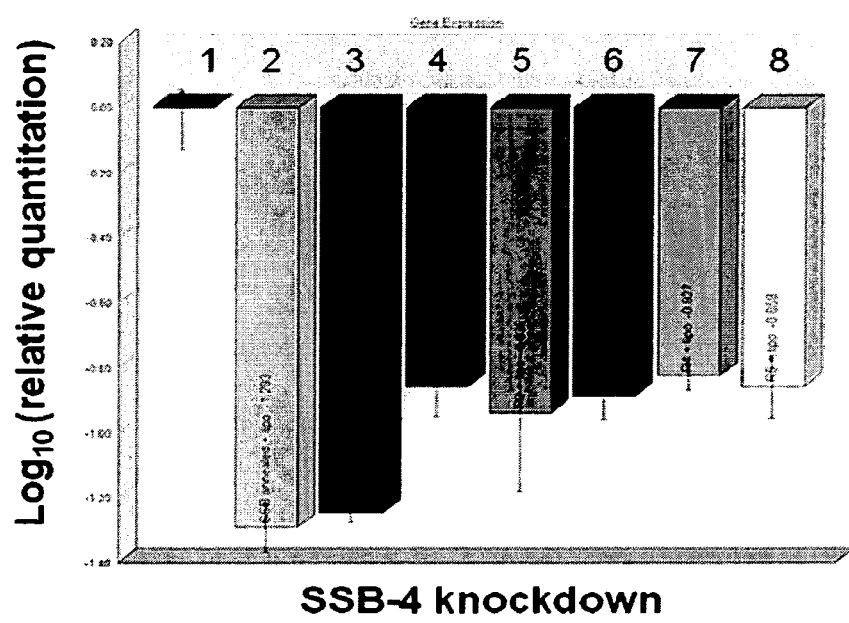
FIG. 30 is a graph as further described in Example 34 and shows the knockdown of SSB RNA expression by conjugates R1 through R5 when transfected using Lipofectamine-2000. SSB gene expression relative to untreated cells (bar1), annealed siRNA (bar2), control SSB siRNA (bar3), conjugates R1 through R5 complexed with Lipofectamine-2000 (bars 4 through 8).
Figure 31:
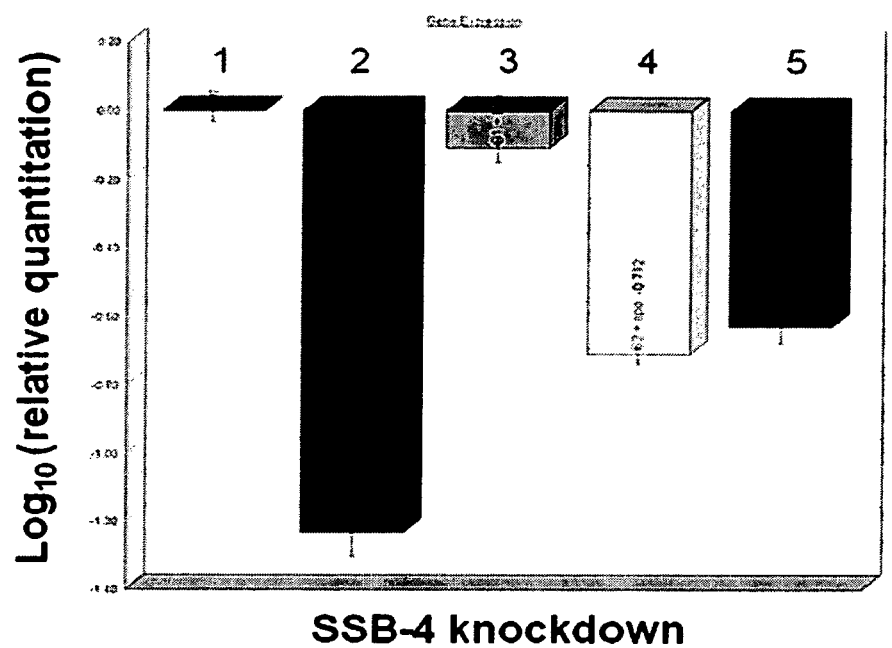
FIG. 31 is a graph as further described in Example 34 and shows the SSB gene expression relative to untreated cells (bar1), control SSB siRNA (bar2), conjugates S1 through S3 complexed with Lipofectamine-2000 (bars 3 through 5).
Figure 32:
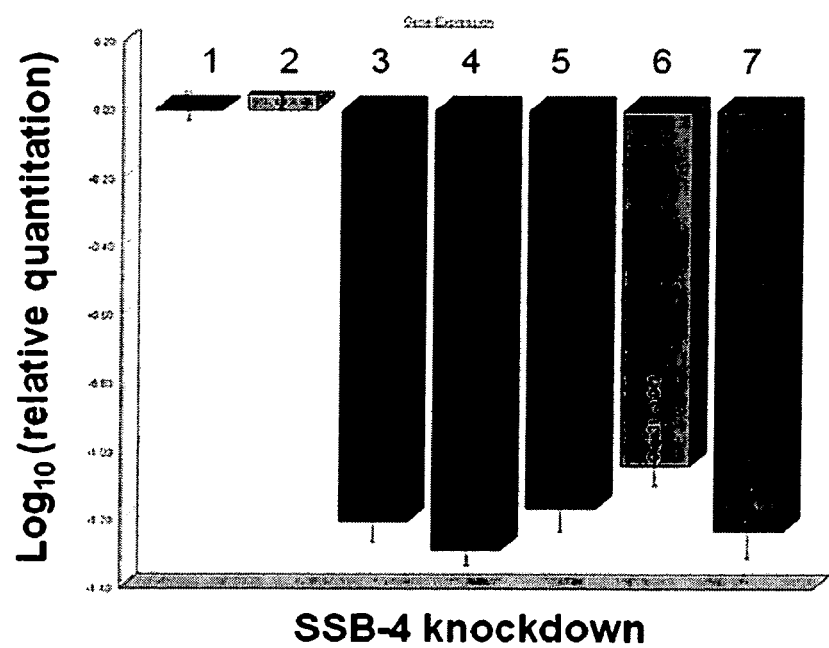
FIG. 32 is a graph as further described in Example 34 and shows the SSB gene expression relative to untreated cells (bar1), cells treated with lipofectamine-2000 (bar2), Oligo3 (SEQ ID NO: 186): 5'(C6-S—SC6)-AmCAmACmAG-mACmUUmUAmAUmGUmAA-3' (bar3), Oligo5 (SEQ ID NO: 187): 5'(C6-NH2)AmCAmACmAGmACmUUmUA-mAUmGUmAA-3'(C6-NH2) (bar4), Oligo28 (SEQ ID NO: 188): 5' mUUmACmAUmUAmAAmGUmCUmGU-mUGmU-3' (C6-NH) (Cy5.5) (bar5), Oligo31 (SEQ ID NO: 189): 5' mUUmACmAUmUAmAAmGUmCUmGU-mUGmU-3' (C6-NH$_2$) (bar6), Oligo34 (SEQ ID NO: 190): 5' mUUmACmAUmUAmAAmGUmCUmGUmUGmU-3' C3-S—S—C3(bar7).

FIG. 30 shows knockdown of SSB RNA expression by conjugates R1 through R5 when transfected using Lipofectamine-2000. SSB gene expression relative to untreated cells (bar1), annealed siRNA (bar2), control SSB siRNA (bar3), conjugates R1 through R5 complexed with Lipofectamine-2000 (bars 4 through 8). FIG. 31 shows knockdown of SSB RNA expression in cells treated with conjugates S1 through S3 transfected using Lipofectamine-2000. FIG. 32 shows SSB RNA expression knockdown by SSB siRNA with various linkers attached prior to polymer conjugation. All constructs shown were annealed prior to use with the same sense or antisense strand sequence.

Example 35

Evaluation of Chitosan-PEG Complexes with siRNAs

PAGE Gel electrophoresis of siRNA/chitosan ionic complexes. The siRNA and chitosan or chitosan/PEG conjugates are mixed together at a given ratio of N:P with a volume of 15 μL, added to this solution is 3 μL of a loading material containing 50% glycerol. Each sample (10 μl) is loaded into a 15% PAGE gel running a TAE buffer (Tris Acetate EDTA) at pH 7.3. The gel is run at 100 volts for two hours, afterwards the gel is removed from the cassette and stained for 10 minutes using 10 mg/mL ethidium bromide solution and washed for a minimum of one hour in DI water. The ethidium bromide stained gel is visualized by UV light.

Complexes of various chitosan/siRNA modifications were evaluated using analysis using PAGE gel. PAGE gel analysis was completed using a 1:1 and a 2:1 ratio (N:P) of a chitosan 3-5 kD/mPEG-butrALD 5 kD and chitosan 10 kD/mPEG-butrALD 5 kD using a running buffer of TBE (pH 8.4), TAE (pH 7.3) and TAE (pH 5.3). No neutralization of the siRNA duplex (SEQ ID NO: 183:SEQ ID NO: 192) was seen with the chitosan 3-5K and some slight tailing seen with the chitosan 10K complexes indicating some neutralization of the siRNA duplex.

Figure 33:
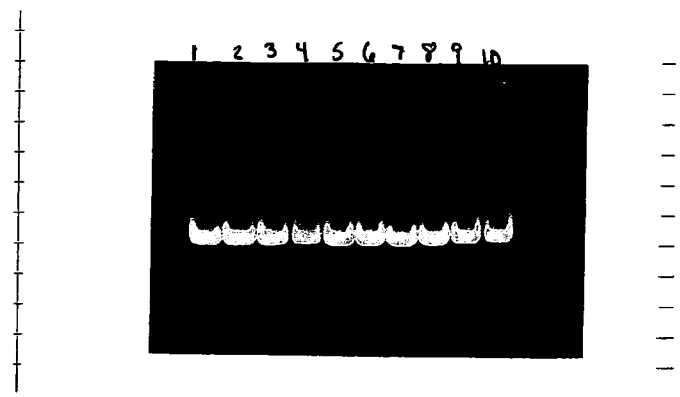
FIG. 33 and FIG. 34 are representations of gels as further described in Example 35.

The gel showing the analysis of chitosan-PEG complexes with siRNA is provided in FIG. 33, wherein lane 1 corresponds to the siRNA duplex, lane 2 corresponds to chitosan 3-5K/ALD 5K and siRNA at 1:1, lane 3 corresponds to chitosan 10K/ALD 5K and siRNA at 1:1, lane 4 corresponds to chitosan 10K/ALD 5K and siRNA at 2:1, lane 5 corresponds to IR 800CW dye labeled chitosan 10K/BTC 5K and siRNA at 1:1, lane 6 corresponds to IR 800CW dye labeled chitosan 10K/BTC 5K and siRNA at 2:1, lane 7 corresponds to siRNA duplex, lane 8 corresponds to chitosan 3-5K/ALD 5K and siRNA at 1:1, lane 9 corresponds to chitosan 10K/ALD 5K and siRNA at 1:1, and lane 10 corresponds to chitosan 10K/ALD 5K and siRNA at 2:1.

Figure 34:
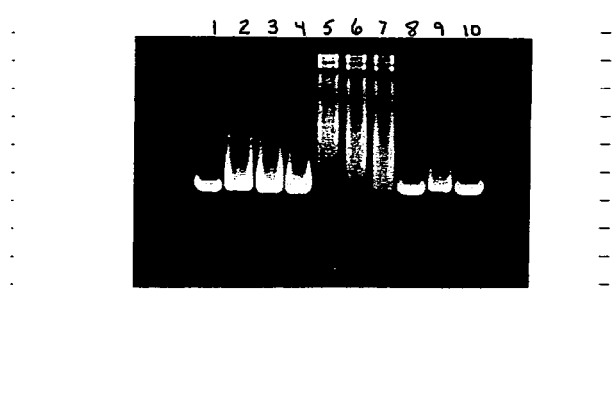

Increasing the nitrogen ratio leads to neutralization of the siRNA duplex. Analysis based on a PAGE gel using TAE buffer at pH 7.3 was performed. The chitosan 10 kD/mPEG-butrALD 5 kD neutralizes the siRNA duplex, as revealed by the PAGE gels. The gel showing the analysis of chitosan-PEG complexes with siRNA, wherein the complexes were formed with increased nitrogen ratios is provided in FIG. 34. In this gel, lane 1 corresponds to siRNA duplex, lane 2 corresponds to chitosan 3-5K/ALD 5K and siRNA at 50:1, lane 3 corresponds to chitosan 3-5K/ALD 5K and siRNA at 20:1, lane 4 corresponds to chitosan 3-5K/ALD 5K and siRNA at 10:1, lane 5 corresponds to chitosan 10K/ALD 5K and siRNA at 50:1, lane 6 corresponds to chitosan 10K/ALD 5K and siRNA at 20:1, lane 7 corresponds to chitosan 10K/ALD 5K and siRNA at 10:1, lane 8 corresponds to siRNA duplex, lane 9 corresponds to IR 800CW dye labeled chitosan 10K/BTC 5K and siRNA at 10:1, and lane 10 corresponds to siRNA duplex.

---

What is claimed is:

1. A conjugate comprising a residue of a siNA having a 5' amino linker with a terminal amino group having the structure

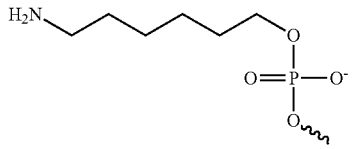

covalently attached at the terminal amino group to a single polymeric reagent having the following structure,

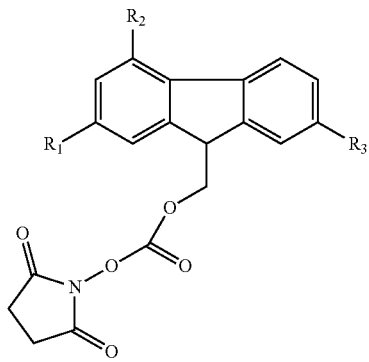

wherein: $R_2$ is H and each of $R_1$ and $R_3$ is

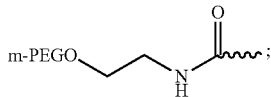

$R_2$ is H and each of $R_1$ and $R_3$ is

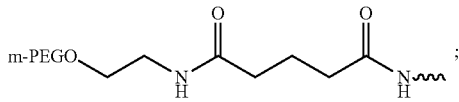

$R_1$ is H, $R_2$ is

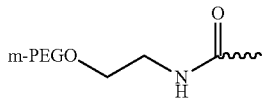

and $R_3$ is

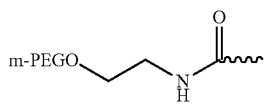

; or $R_1$ is H, $R_2$ is m-PEGO\~\~\~N(H)\~\~C(O)\~\~ and $R_3$ is m-PEGO\~\~\~N(H)\~\~C(O)\~\~, where each m-PEG represents $CH_3O(CH_2CH_2O)_n$—$CH_2CH_2$~ and (n) is defined to provide $CH_3O(CH_2CH_2O)_n$—$CH_2CH_2$~ with a weight-average molecular weight of from 10,000 Daltons to 40,000 Daltons, and wherein the siNA is selected from the group consisting of double stranded siNA that is blunt ended, double stranded siNA that has a 5'overhang, and double stranded siNA that has a 3' overhang.

2. The conjugate of claim 1, wherein the siNA is a siRNA.
3. The conjugate of claim 1, wherein the siNA has a length of from 10 to 30 nucleotides.
4. The conjugate of claim 1, wherein the siNA has a length of from 15 to 25 nucleotides.
5. The conjugate of claim 1, wherein the siNA is double stranded siNA that is blunt ended.
6. The conjugate of claim 1, wherein the siNA is double stranded siNA that has a 5'overhang.
7. The conjugate of claim 6, wherein the 5'overhang is an overhang of a number of nucleotides selected from the group consisting of 1, 2, 3 and 4.
8. The conjugate of claim 1, wherein the siNA is a double stranded siNA that has a 3'overhang.
9. The conjugate of claim 8, wherein the 3'overhang is an overhang of a number of nucleotides selected from the group consisting of 1, 2, 3 and 4.
10. The conjugate of claim 1, wherein the siNA includes one or more modified nucleotides selected from the group consisting of 2'O-methyl nucleotides, 2'F nucleotides, 2'deoxynucleotides, 2'OMOE nucleotides, locked nucleic acids and unlocked nucleic acids.

\* \* \* \* \*